United States Patent
Amberg et al.

(10) Patent No.: US 9,586,945 B2
(45) Date of Patent: Mar. 7, 2017

(54) AMINOCHROMANE, AMINOTHIOCHROMANE AND AMINO-1,2,3,4-TETRAHYDROQUINOLINE DERIVATIVES, PHARMACEUTICAL COMPOSITIONS CONTAINING THEM, AND THEIR USE IN THERAPY

(71) Applicants: AbbVie Deutschland GmbH & Co. KG, Wiesbaden (DE); AbbVie Inc., North Chicago, IL (US)

(72) Inventors: Wilhelm Amberg, Ludwigshafen (DE); Frauke Pohlki, Ludwigshafen (DE); Udo Lange, Ludwigshafen (DE); Ying Wang, Libertyville, IL (US); Jason Brewer, Zion, IL (US); Anil Vasudevan, Union Grove, WI (US); Yanbin Lao, North Chicago, IL (US); Charles Hutchins, Green Oaks, IL (US); Hongyu Zhao, Libertyville, IL (US); Huan-Qiu Li, Wilmette, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 14/517,034

(22) Filed: Oct. 17, 2014

(65) Prior Publication Data
US 2015/0111867 A1    Apr. 23, 2015

Related U.S. Application Data

(60) Provisional application No. 61/892,203, filed on Oct. 17, 2013.

(51) Int. Cl.
| | | |
|---|---|---|
| C07D 405/04 | (2006.01) | |
| C07D 405/14 | (2006.01) | |
| C07D 311/58 | (2006.01) | |
| A61K 31/352 | (2006.01) | |

(52) U.S. Cl.
CPC .......... *C07D 405/14* (2013.01); *C07D 311/58* (2013.01); *C07D 405/04* (2013.01)

(58) Field of Classification Search
CPC ... C07D 405/14; C07D 311/58; C07D 405/04
USPC ........ 514/210.2, 210.19; 544/238; 546/282.7
See application file for complete search history.

(56) References Cited

U.S. PATENT DOCUMENTS

| | | |
|---|---|---|
| 3,867,391 A | 2/1975 | Holland |
| 4,927,838 A | 5/1990 | Guthrie et al. |
| 5,506,246 A | 4/1996 | Junge et al. |
| 5,519,034 A | 5/1996 | Kozlik et al. |
| 5,545,755 A | 8/1996 | Lin et al. |
| 6,057,357 A | 5/2000 | Horwell et al. |
| 6,197,798 B1 | 3/2001 | Fink |
| 6,331,636 B1 | 12/2001 | Romero et al. |
| 6,426,346 B1 | 7/2002 | Pruitt et al. |
| 7,189,850 B2 | 3/2007 | Ceccarelli et al. |
| 7,427,612 B2 | 9/2008 | Alberati-giani et al. |
| 7,462,617 B2 | 12/2008 | Alberati-giani et al. |
| 7,511,013 B2 | 3/2009 | Molino et al. |
| 7,514,068 B2 | 4/2009 | Tung |

(Continued)

FOREIGN PATENT DOCUMENTS

| | | |
|---|---|---|
| DE | 10315570 | 10/2004 |
| EP | 0091241 | 10/1983 |

(Continued)

OTHER PUBLICATIONS

Harada et al. "A novel glycine transporter-1 (GlyT1) inhibitor, ASP2535 (4-[3-isopropyl-5-(6-phenyl-3-pyridyl)-4H-1,2,4-triazol-4-yl]-2,1,3-benzoxadiazole), improves cognition in animal models of cognitive impairment in schizophrenia and Alzheimer's disease" Eur. J. Pharmacol. 2012, 685, 59-69.*
United States Patent Office Notice of Allowance for U.S. Appl. No. 13/468,682 dated Nov. 30, 2015 (5 pages).
United States Patent Office Notice of Allowance for U.S. Appl. No. 13/764,454 dated Jan. 7, 2016 (10 pages).
United States Patent Office Action for U.S. Appl. No. 14/215,533 dated Nov. 6, 2015 (16 pages).
United States Patent Office Action for U.S. Appl. No. 14/216,222 dated Nov. 10, 2015 (16 pages).
Database Registry Chemical Abstracts Service, Columbus, Ohio, Accession No. RN 1394343-08-8, Entered STN: Sep. 17, 2012 (2 pages).

(Continued)

*Primary Examiner* — Michael Barker
*Assistant Examiner* — Amanda L Aguirre
(74) *Attorney, Agent, or Firm* — Neal, Gerber & Eisenberg LLP

(57) ABSTRACT

The present invention relates to aminochromane, aminothiochromane and amino-1,2,3,4-tetrahydroquinoline derivatives of the formula (I)

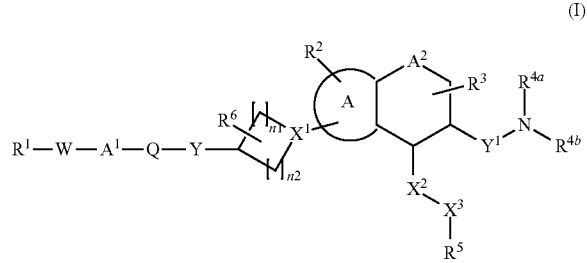

or a physiologically tolerated salt thereof.
The invention relates to pharmaceutical compositions comprising such aminochromane, aminothiochromane and amino-1,2,3,4-tetrahydroquinoline derivatives, and the use of such aminochromane, aminothiochromane and amino-1,2,3,4-tetrahydroquinoline derivatives for therapeutic purposes. The aminochromane, aminothiochromane and amino-1,2,3,4-tetrahydroquinoline derivatives are GlyT1 inhibitors.

21 Claims, No Drawings

(56) References Cited

U.S. PATENT DOCUMENTS

| | | | |
|---|---|---|---|
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 8,420,670 B2 | 4/2013 | Amberg et al. |
| 8,563,617 B2 | 10/2013 | Amberg et al. |
| 8,642,587 B2 | 2/2014 | Lange et al. |
| 8,653,100 B2 | 2/2014 | Amberg et al. |
| 8,846,741 B2 | 9/2014 | Amberg et al. |
| 8,846,743 B2 | 9/2014 | Pohlki et al. |
| 8,853,196 B2 | 10/2014 | Amberg et al. |
| 8,877,937 B2 | 11/2014 | Molt et al. |
| 8,883,839 B2 | 11/2014 | Pohlki et al. |
| 8,957,089 B2 | 2/2015 | Amberg et al. |
| 9,051,280 B2 | 6/2015 | Lange et al. |
| 2002/0169197 A1 | 11/2002 | Egle et al. |
| 2003/0083359 A1 | 5/2003 | Lee et al. |
| 2004/0026364 A1 | 2/2004 | Kihara |
| 2005/0124627 A1 | 6/2005 | Schadt et al. |
| 2005/0153963 A1 | 7/2005 | Dargazanli et al. |
| 2005/0153980 A1 | 7/2005 | Schadt et al. |
| 2005/0159450 A1 | 7/2005 | Dargazanli et al. |
| 2005/0267152 A1 | 12/2005 | Bloomfield et al. |
| 2006/0035925 A1* | 2/2006 | Cai ............... A61K 31/35 514/310 |
| 2006/0074105 A1 | 4/2006 | Ware et al. |
| 2006/0223802 A1 | 10/2006 | Dargazanli et al. |
| 2006/0223861 A1 | 10/2006 | Dargazanli et al. |
| 2006/0223885 A1 | 10/2006 | Dargazanli et al. |
| 2006/0223886 A1 | 10/2006 | Dargazanli et al. |
| 2007/0021408 A1 | 1/2007 | Molino et al. |
| 2007/0155753 A1 | 7/2007 | Ye et al. |
| 2007/0185056 A1 | 8/2007 | Duan et al. |
| 2007/0214087 A1 | 9/2007 | Kawaguchi et al. |
| 2008/0045540 A1 | 2/2008 | Keil et al. |
| 2008/0070941 A1 | 3/2008 | Dargazanli et al. |
| 2008/0119486 A1 | 5/2008 | Jolidon et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2012/0040947 A1 | 2/2012 | Pohlki et al. |
| 2012/0040948 A1 | 2/2012 | Pohlki et al. |
| 2012/0077796 A1 | 3/2012 | Pohlki et al. |
| 2012/0088790 A1 | 4/2012 | Pohlki et al. |
| 2012/0295881 A1 | 11/2012 | Lange et al. |
| 2012/0316153 A1 | 12/2012 | Amberg et al. |
| 2013/0035323 A1 | 2/2013 | Amberg et al. |
| 2013/0131132 A1 | 5/2013 | Amberg et al. |
| 2013/0184238 A1 | 7/2013 | Amberg et al. |
| 2013/0203749 A1 | 8/2013 | Amberg et al. |
| 2013/0210880 A1 | 8/2013 | Amberg et al. |
| 2014/0005247 A1* | 1/2014 | Alarcon Sanchez ... C07D 311/58 514/422 |
| 2014/0031331 A1 | 1/2014 | Amberg et al. |
| 2014/0256701 A1 | 9/2014 | Pohlki et al. |
| 2014/0275086 A1 | 9/2014 | Amberg et al. |
| 2014/0275087 A1 | 9/2014 | Amberg et al. |
| 2014/0309206 A1 | 10/2014 | Pohlki et al. |
| 2015/0111875 A1 | 4/2015 | Amberg et al. |

FOREIGN PATENT DOCUMENTS

| | | |
|---|---|---|
| EP | 0258755 | 3/1988 |
| EP | 0303961 | 2/1989 |
| EP | 0420064 | 4/1991 |
| EP | 1199306 | 4/2002 |
| EP | 1254662 | 11/2002 |
| EP | 1284257 | 2/2003 |
| EP | 2246331 | 11/2010 |
| ES | WO 2012042078 A1 * | 4/2012 ........... C07D 311/58 |
| WO | 81/03491 | 12/1981 |
| WO | 90/15047 | 12/1990 |
| WO | 92/06967 | 4/1992 |
| WO | 92/19234 | 11/1992 |
| WO | 92/22533 | 12/1992 |
| WO | 93/13073 | 7/1993 |
| WO | 95/07271 | 3/1995 |
| WO | 97/10223 | 3/1997 |
| WO | 97/45115 | 12/1997 |
| WO | 98/04521 | 2/1998 |
| WO | 98/56757 | 12/1998 |
| WO | 00/07978 | 2/2000 |
| WO | 00/20376 | 4/2000 |
| WO | 01/09120 | 2/2001 |
| WO | 01/46155 | 6/2001 |
| WO | 02/076979 | 10/2002 |
| WO | WO 02092594 A1 * | 11/2002 ............. A61K 31/35 |
| WO | 03/031435 | 4/2003 |
| WO | 03/045924 | 6/2003 |
| WO | 03/053942 | 7/2003 |
| WO | 03/055478 | 7/2003 |
| WO | 03/068220 | 8/2003 |
| WO | 03/076420 | 9/2003 |
| WO | 03/087086 | 10/2003 |
| WO | 03/089411 | 10/2003 |
| WO | 03/097586 | 11/2003 |
| WO | 2004/007468 | 1/2004 |
| WO | 2004/013100 | 2/2004 |
| WO | 2004/013101 | 2/2004 |
| WO | 2004/022528 | 3/2004 |
| WO | 2004/071445 | 8/2004 |
| WO | 2004/072034 | 8/2004 |
| WO | 2004/080968 | 9/2004 |
| WO | 2004/096761 | 11/2004 |
| WO | 2004/110149 | 12/2004 |
| WO | 2004/112787 | 12/2004 |
| WO | 2004/113280 | 12/2004 |
| WO | 2004/113301 | 12/2004 |
| WO | 2005/009996 | 2/2005 |
| WO | 2005/014563 | 2/2005 |
| WO | 2005/023260 | 3/2005 |
| WO | 2005/037781 | 4/2005 |
| WO | 2005/037782 | 4/2005 |
| WO | 2005/037783 | 4/2005 |
| WO | 2005/037785 | 4/2005 |
| WO | 2005/037792 | 4/2005 |
| WO | 2005/023261 | 5/2005 |
| WO | 2005/040166 | 5/2005 |
| WO | 2005/046601 | 5/2005 |
| WO | 2005/049023 | 6/2005 |
| WO | 2005/058317 | 6/2005 |
| WO | 2005/058882 | 6/2005 |
| WO | 2005/058885 | 6/2005 |
| WO | 2005/099353 | 10/2005 |
| WO | 2005/123681 | 12/2005 |
| WO | 2006/008754 | 1/2006 |
| WO | 2006/034235 | 3/2006 |
| WO | 2006/040177 | 4/2006 |
| WO | 2006/063709 | 6/2006 |
| WO | 2006/082001 | 8/2006 |
| WO | 2006/102760 | 10/2006 |
| WO | 2006/121767 | 11/2006 |
| WO | 2007/143823 | 12/2007 |
| WO | 2008/038053 | 4/2008 |
| WO | 2008/038841 | 4/2008 |
| WO | 2008/148755 | 12/2008 |
| WO | 2009/024011 | 2/2009 |
| WO | 2009/121872 | 10/2009 |
| WO | 2010/020548 | 2/2010 |
| WO | 2010/025856 | 3/2010 |
| WO | 2010/029180 | 8/2010 |
| WO | 2010/092181 | 8/2010 |
| WO | 2010/138901 | 12/2010 |
| WO | 2012/020130 | 2/2012 |

(56) References Cited

FOREIGN PATENT DOCUMENTS

| WO | 2012/020131 | 2/2012 |
|---|---|---|
| WO | 2012/020133 | 2/2012 |
| WO | 2012/020134 | 2/2012 |
| WO | 2012/152915 | 11/2012 |
| WO | 2013/020930 | 2/2013 |
| WO | 2013/072520 | 5/2013 |
| WO | 2013/120835 | 8/2013 |

OTHER PUBLICATIONS

ACS Database Accession No. 1381432-38-7 (Jul. 4, 2012).
ACS Database Accession No. 1394552-70-5 (Sep. 18, 2012).
ACS Database Accession No. 1410185-83-9 (Dec. 3, 2012).
ACS Database Accession No. 1434168-57-6 (Jun. 4, 2013).
ACS Database Accession No. 1434399-98-0 (Jun. 5, 2013).
ACS Database Accession No. 1506112-12-4 (Dec. 29, 2013).
ACS Database Accession No. 1515211-93-4 (Jan. 9, 2014).
ACS Database Accession No. 1521424-46-3 (Jan. 16, 2014).
ACS Database Accession No. 1530956-16-1 (Jan. 27, 2014).
ACS Database Accession No. 1535994-72-9 (Feb. 3, 2014).
Ashby, E.C. et al., "Single electron transfer in reactions of alkyl halides with lithium thiolates," J. Org. Chem. (1985) 50(25):5184-5193.
Barbasiewicz, M. et al., "Intermolecular reactions of chlorohydrine anions: acetalization of carbonyl compounds under basic conditions," Org. Lett. (2006) 8(17):3745-3748.
Baumann, M. et al., "Synthesis of a drug-like focused library of trisubstituted pyrrolidines using integrated flow chemistry and batch methods," ACS Comb. Sci. (2011) 13:405-413.
Belliotti, T.R. et al., "Structure-activity relationships of pregabalin and analogues that target the alpha(2)-delta protein," J. Med. Chem. (2005) 48(7):2294-2307.
Bermejo, A. et al., "Syntheses and antitumor targeting G1 phase of the cell cycle of benzoyldihydroisoquinolines and related 1-substituted isoquinolines," J. Med. Chem. (2002) 45:5058-5068.
Beylot, M. et al., "In vivo studies of intrahepatic metabolic pathways," Diabetes Metabolism (1997) 23(3):251-257.
Bishop, D.C., "Analgetics based on the azetidine ring," Azetidine Analgetics (1968) 11:466-470.
Blagojevic, N. et al., "Role of heavy water in boron neutron capture therapy," Topics in Dosimetry and Treatment Planning for Neutron Capture Theorpy (1994) 125-134.
Blake, M.I. et al., "Studies with deuterated drugs," J. Pharm. Sci. (1975) 64(3):367-391.
Boulay, D. et al., "Characterization of SSR103800, a selective inhibitor of the glycine transporter-1 in models predictive of therapeutic activity in schizophrenia," Pharmacology, Biochemistry and Behavior (2008) 91:47-58.
Brickner, S.J. et al., "Synthesis and antibacterial activity of U-100592 and U-100766, two oxazolidinone antibacterial agents for the potential treatment of multidrug-resistant gram-positive bacterial infections," J. Med. Chem. (1996) 39(3):673-679.
Burn, D., "Alkylation with the vilsmeier reagent," Chem. and Industry (1973) 870-873.
Burns, N.Z. et al., "Total synthesis of haouamine A: the indenotetrahydropyridine core," Tetrahedron (2009) 65(33):6600-6610.
Butte, N.F. et al., "Measurement of milk intake: tracer-to-infant deuterium dilution method," Br. J. Nutrition (1991) 65:3-14.
Cheng, Y. et al., "Relationship between the inhibition constant (KI) and the concentration of inhibitor which causes 50 percent inhibition (I.sub.50) of an enzymatic reaction," Biochem. Pharmacol. (1973) 22:3099-3108.
Cheung, F.K. et al., "The use of a [4+2] cycloadditional reaction for the preparation of a series of 'tethered' Ru(II)-diamine and aminoalcohol complexes," Org. & Biomol. Chem. (2007) 5(7):1093-1103.
Chrzanowska, M. et al., "Asymmetric synthesis of isoquinoline alkaloids," Chem. Rev. (2004) 104(7):3341-3370.

Clayden, J. et al., "2,3-Dihydroisoindolones by cyclisation and rearomatisation of lithiated benzamides," Tetra. Lett. (2003) 44(15):3059-3062.
Clezy, P.S. et al., "Preparation of a deuterated analogue of tetrahydropapaveroline suitable for use as an internal standard for G.C./M.S. analysis of this alkaloid: retro pictet-spengler condensation," Australian J. Chem. (1998) 41:483-491.
Colandrea, V.J. et al., "Synthesis and regioselective alkylation of 1.6- and 1.7-naphthyridines," Tetra. Lett. (2000) 41:8053-8057.
Coward, W.A. et al., "New method for measuring milk intakes in breast-fed babies," The Lancet (1979) 13-14.
Czajka, D.M. et al., "Effect of deuterium oxide on the reproductive potential of mice," Annals of the New York Academy of Sciences (1960) 84:770-779.
Czajka, D.M. et al., "Physiological effects of deuterium on dogs," Am. J. Physiology (1961) 201(2):357-362.
Database Registry Chemical Abstracts Service, Columbus, Ohio, Accession No. RN1057254-23-5 entered STN: Oct. 5, 2008.
Database Registry Chemical Abstracts Service, Columbus, Ohio, Accession No. RN267876-15-3 entered STN: Jun. 2, 2000.
Denkewalter, R.G. et al., Progress of Pharmaceutical Research, Drug Research (1966) 10:223-226.
Di, L. et al., "Optimization of a higher throughput microsomal stability screening assay for profiling drug discovery candidates," J. Biomol. Screening (2003) 8(4):453-462.
Dohi, T. et al., "Glycine transporter inhibitors as a novel drug discovery strategy for neuropathic pain," Pharma. & Therapeutics (2009) 123(1):54-79.
Donohoe et al., Document No. 139:117274 retrieved from CAPLUS, "Product class 14:1H- and 2H-isoindoles" Sci of Synthesis (2001) 10:653-692.
Duan, Z.C. et al., "Highly enantioselective Rh-catalyzed hydrogenation of beta gamma-unsaturated phosphonates with chiral ferrocene-based monophosphoramidite ligands," J. Org. Chem. (2009) 74(23):9191-9194.
Erhunmwunse, M.O. et al., "A novel rearrangement reaction of beta-diaxo-alpha-ketoacetals," Tetra. Lett. (2009) 50:3568-3570.
Estieu, K. et al., "New alkylidenecyclo propane amino acid derivatives for an efficient construction of the 6H-pyrrolo[3,4-b]pyridine skeleton," J. Org. Chem. (1997) 62:8276-8277.
Ferles, M. et al., "Reduction of 1-isoquinolyl-dimethylmethanol and 1-(1-isoquinolyl)cyclohexanon," Collection of Czechoslovak Chem. Comm. (1981) 46(1):262-265.
Fiedler, H.B., "Lexikon der hilfsstoffe fur pharmazie, Kosmetik und angrenzende Gebiete," (1996) 4th Edition, Table of Contents.
Foster, A.B. et al., "Deuterium isotope effects in the metabolism of drugs and xenobiotics: implications for drug design," Advances in Drug Research (1985) 14:2-36.
Fraser, R.R. et al., "Effect of substituents on the chemical shift of benzylic protons. III," Canadian Journal of Chemistry (1971) 49(5):800-802.
Grant & Hackh's Chemical Dictionary, 5th Edition (1987), p. 148.
Green, G.M. et al., "Polystyrene-supported benzenesulfonyl azide: a diazo transfer reagent that is both efficient and safe," J. Org. Chem. (2001) 66(7):2509-2511.
Greene, T.W. et al., in Protective Groups in Organic Synthesis, 2nd Edition, John Wiley & Sons, Inc., (1991) Table of Contents.
Greene, T.W. et al., in Protective Groups in Organic Synthesis, 3rd Edition, John Wiley & Sons, Inc., (1999) Preface, Table of Contents and Abbreviations.
Guillonneau, C. et al., "Synthesis of 9-O-substituted derivatives of 9-hydroxy-5, 6-dimethyl-6H-pyrido[4,3-b]carbazole-1-carboxylic acid (2-(dimethylamino)ethyl)amide and their 10- and 11-methyl analogues with improved antitumor activity," J. Med. Chem. (1999) 42(12):2191-2203.
Gupta, A. et al., "Simple and efficient synthesis of steroidal hybrids of estrogen and vitamin D3," Synthetic Comm. (2009) 39:61-69.
Harsing, L.G. et al., "Glycine transporter Type-1 and its inhibitors," Curr. Med. Chem. (2006) 13:1017-1044.
Hashimoto, K. "Glycerine transport inhibitors for the treatment of schizophrenia," The Open Medicinal Chemistry Journal (2010) 4:10-19.

(56) References Cited

OTHER PUBLICATIONS

Hashimoto, K. et al., "Phencyclidine-induced cognitive deficits in mice are improved by subsequent subchronic administration of the glycine transporter-1 inhibitor NFPS and D-serine," Eurp. Neuropsychopharmacology (2008) 18:414-421.

Hashimoto, K., "Glycine transporter inhibitors as therapeutic agents for schizophrenia," Recent Patents on CNS Drug Discovery (2006) 1:43-53.

Hermanns, H. et al., "Differential effects of spinally applied glycine transporter inhibitors on nociception in a rat model of neuropathic pain," Neurosci Lett. (2008) 445:214-219.

Hillier, M.C. et al., "A one-pot preparation of 1,3-disubstituted azetidines," J. Org. Chem. (2006) 71(20):7885-7887.

Ikunaka, M. et al., "The highly selective equatorial hydride delivery by biocatalysis: chemoenzymatic synthesis of trans-2-(4-propylcyclohexyl)-1,3-propanediol via cis-4-propylcyclohexanol," Organic Process Research and Development (2004) 8(3):389-395.

Ito, N. et al., "A medium-term rat liver bioassay for rapid in vivo detection of carcinogenic potential of chemicals," Cancer Sci. (2003) 94:3-8.

Javitt, D.C., "Glutamate as a therapeutic target in psychiatric disorders," Mol. Psychiatry (2004) 9:984-997.

Jellimann, C. et al., "Synthesis of phenalene and acenaphthene derivatives as new conformationally restricted ligands for melatonin receptors," J. Med. Chem. (2000) 43(22):4051-4062.

Jensen, B.L. et al., "Total synthesis of 4,5,7a,8-tetrahydro-1,2-dimethoxyphenanthro[10,1-bc]-azepin-6(7H)-one: a photochemical approach," J. Heterocyclic Chem. (1986) 23:343-347.

Jetter, M.C. et al., "Heteroaryl beta-tetralin ureas as novel antagonists of human TRPV1," Bioorg. Med. Chem. Lett. (2007) 17(22):6160-6163.

Jutz, C. et al., "The Vilsmeier-Haackarnold acylations. C—C bond-forming reactions of chloromethyleniminium ions," Adv. Org. Chem. (1976) 9(1):225-342.

Kaiser, C. et al., "6,7-dichloro-1-(3,4,5-trimethyoxygenzyl)-1,2,3,4-tetrahydroisoquinoline. A structurally novel beta-adrenergic receptor blocking agent," J. Med. Chem. (1986) 29(11):2381-2384.

Kametani, T. et al., "Studies on the syntheses of heterocyclic compounds. Part DLXXVII. Synthesis of 2,3,4,5-tetrahydro-1H-benzazepine derivatives by phenolic cyclisation," Journal of the Chemical Society, Perkin Trans 1, (1974) 22:2602-2604.

Kato, S. et al., "Synthesis of deuterated mosapride citrate," J. Labelled Compounds and Radiopharmaceuticals (1995) 36(10):927-932.

King, F.D., editor "Bioisosteres, conformational restriction and pro-drugs—case history: an example of a conformational restriction approach," Medical Chemistry: Principles and Practice (1994), Chapter 14, 206-209.

Kinney, G.G. et al., "The glycerine transporter type 1 inhibitor N-[3-(4'-fluorophenyl)-3-(4'-phenylphenoxy)propyl] sarcosine potentiates NMDA receptor-mediated responses in vivo and produces an antipsychotic profile in rodent behavior," The Journal of Neurosci. (2003) 23(20):7586-7591.

Kocienski, P.J., Protective Groups, Georg Thieme Verlag Stuttgart, Germany, Table of Contents (1994).

Kreher, R.P., Hetarene II, Georg Thieme Verlag Stuttgart, Germany (1991) 583-726.

Kuhakarn, C. et al., "Synthesis of alkylated indolizidine alkaloids via pummerer mediated cyclization: synthesis of indolizidine 167B, 5-butylindolizidine and monomorine I," Tetrahedron (2008) 64(8):1663-1670.

Kushner et al., "Pharmacological uses and perspectives of heavy water and deuterated compounds," Canadian J. Physiol. Pharmacol. (1999) 77(2):79-88.

Lindsley, C.W. et al., "Design, synthesis, and in vivo efficacy of glycine transporter-1 (GlyT1) inhibitors derived from a series of [4-phenyl-1-(propylsulfonyl)piperidin-4-yl]methyl benzamides," Chem. Med. Chem. (2006) 1(8):807-811.

Lindsley, C.W. et al., "Progress in the preparation and testing of glycine transporter type-1 (glyT1) inhibitors," Curr. Top. Med. Chem. (2006) 6:1883-1896.

Lindsley, C.W. et al., "Progress towards validating the NMDA receptor hypofunction hypothesis of schizophrenia," Cur. Top. Med. Chem. (2006) 6:771-785.

Lizondo, J. et al., "Linezolid: oxazolindinone antibacterial," Drugs of the Future (1996) 21(11):1116-1123.

Lowe, J. et al., "A novel-nonsubstrate-based series of glycine type 1 transporter inhibitors derived from high-throughput screening," Bioorg. Med. Chem. Lett. (2007) 17(6):1675-1678.

Maclennan, A.H. et al., "Neonatal body water turnover: a putative index of perinatal morbidity," Amer. J. Obstetrics & Gynecology (1981) 139(8):948-952.

Mai, K. et al., "A fast n-substituted alpha-aminonitrile synthesis," Synthetic Commun. (1985) 15(2):157-163.

Mallesham, B. et al., "Highly efficient cul-catalyzed coupline of aryl bromides with oxazolidinones using Buchwald's protocol: a short route to linezolid and toloxatone," Org. Left. (2003) 5(7):963-965.

Matsunaga, S. et al., "Linked-BINOL: an approach towards practical asymmetric multifunctional catalysis," Adv. Synth. Catal. (2002) 344(1):3-15.

McOmie, J.F.W., ed., Protective Groups in Organic Chemistry, Plenum Press (1973) Table of Contents.

Meek, J.S. et al., "Diels-Alder reactions of 9-substituted anthracenes.1 II. 9-cyanoanthracene," J. Amer. Chem. Soc. (1956) 78(20):5413-5416.

Memetzidis, G. et al., "Synthesis of aromatic chloroberbines," Heterocycles (1990) 31(2):341-351.

Mezler, M. et al., "Inhibitors of GlyT1 affect glycine transport via discrete binding sites," Mol. Pharmacol. (2008) 74(6):1705-1715.

Morita, K. et al., "Spinal antiallodynia action of glycine transporter inhibitors in muropathic pain models in mice," J. Pharm. Env. Therap. (2008) 326(2):633-645.

Munson, P.J. et al., "Ligand: a versatile computerized approach for characterization of ligand-binding systems," Anal. Biochem. (1980) 107(1):220-239.

Nunez, E. et al., "Differential effects of the tricyclic antidepressant amoxapine on glycine uptake mediated by the recombinant GLYT1 and CLYT2 glycine transporters," Br. J. Pharm. (2000) 129(1):200-206.

Obach, R.S., "Prediction of human clearance of twenty-nine drugs from hepatic microsomal intrinsic clearance data: an examination of in vitro half-life approach and nonspecific binding to microsomes," Drug Metabolism and Disposition (1999) 27(11):1350-1359.

Obach, R.S., "The prediction of human clearance from hepatic microsomal metabolism data," Curr. Opin. Drug Disc. & Development (2001) 4(1):36-44.

Paal, T.A. et al., "Lipase-catalyzed kinetic and dynamic kinetic resolution of 1,2,3,4-tetrahydroisoquinoline-1-carboxylic acid," Tetrahedron: asymmetry (2007) 18(12):1428-1433.

Papageorgiou, C. et al., "163 synthesis of hydroxy-and methoxy-substituted octahydrobenzo[g]isoquinolines as potential ligands for serotonin receptors," Helvetica Chimica Acta (1989) 72:1463-1470.

Pinard, E. et al., "Selective gly T1 inhibitors: discovery of [4-(3-fluoro-5-trifluoremethylpyridin-2-yl)piperazin-1-yl]-]-[5-methanesulfonyl-2-((S)-2,2,2-trifluoro-1-methylethoxy)phenyl)methanone (RG1678), a promising novel medicine to treat schizophrenia," J. Med. Chem. (2010) 53:4603-4614.

Pisaneschi, F. et al., "Diastereoselective cycloaddition of alkylidenecyclopropane nitrones from palladium(O)-catalyzed nucleophilic substitution of asymmetric 1-alkenylcyclopropyl esters by amino acids," Tetrahedron: Asymmetry (2000) 11:897-909.

Pitts, M.R. et al., "Indium metal as a reducing agent in organic synthesis," J. Chem Soc. Perkin Transactions (2001) 1:955-977.

Pons, G. et al., "Stable isotopes labeling of drugs in pediatric clinical pharmacology," Pediatrics (1999) 104(3-2):633-639.

Poornachandran, M. et al., "Synthesis of pyrrolo[3,4-b]pyrroles and perhydrothiazolo-[3',4'-2,3]pyrrolo[4,5-c]pyrroles," Tetrahedron (2008) 64:6461-6474.

Prout, F.S. et al., "3-Benzyl-3-Methylpentanoic acid," Organic Syntheses, Coll. (1963) 4:93; (1955) 35:6.

(56) References Cited

OTHER PUBLICATIONS

Quirante, J. et al., "Synthesis of diazatricyclic core of magangamines from Cis-perhydroisoquinolines," J. Org. Chem. (2008) 73(7):768-771.
Ranu et al., "Indium (III) chloride-promoted rearrangement of epoxides: a selective synthesis of substituted benzylic aldehydes and ketones," J. Org. Chem. (1998) 8212-8216.
Reddy, K.S. et al., "Synthesis of a 9-fluorenone derived beta-amino alcohol ligand depicting high catalytic activity and pronounced non-linear stereochemical effects," Synthesis (2000) 1:165-176.
Reddy, M.P. et al., "Applications of the Vilsmeier reaction. 13. Vilsmeier approach to polycyclic aromatic hydrocarbons," J. Org. Chem. (1981) 46:5371-5373.
Registry No. 1025812-32-1; entered in STN Jun. 5, 2008, "4-morpholineacetamide, N-[2-[[1-[2,4-dihydroxy-5-(1-methylethyl)benzoyl]-2,3-dihydro-1H-isoindol-5-yl]oxy]ethyl]".
Reimann, E. et al., "A convenient synthesis of 1-benzyl-1,2,3,4-tetrahydroisoquinolines by combined Strecker/Bruylants reaction," Monatshefte fur Chemie/Chemical Monthly (2004) 135(10):1289-1295.
Rodewald, L.E. et al., "Deuterium oxide as a tracer for measurement of compliance in pediatric clinical drug trials," J. Pediatrics (1989) 114(5):885-891.
Schwarcz, H.P., "Use of stable isotopes to determine compliance," Controlled Clinical Trials (1984) 5(Supp 4):573-575.
Schwarz, J.B. et al., "Novel cyclopropyl beta-amino acid analogues of pregabalin and gabapentin that target the alpha2-delta protein," J. Med. Chem. (2005) 48(8):3026-3035.
Sharma, S.D. et al., "Phosphorous oxychloride (POCl3): a key molecule in organic synthesis," Indian J. Chem. (1998) 37B:965-978.
Sur, C. et al., "Glycine transporter 1 inhibitors and modulation of NMDA receptor-mediated excitatory neurotransmission," Curr. Drug Targets (2007) 8:643-649.
Taber, D.F. et al., "Enantioselective ring construction: synthesis of (+)-alpha-cuparenone," J. Amer. Chem. Soc. (1985) 107:196-199.
Tanabe, M. et al., "Glycine transporter inhibitors as a potential therapeutic strategy for chronic pain with memory impairment," Anesth. (2008) 108:929-937.
Tavares, F.X. et al., "Potent, selective, and orally efficacious antagonists of melanin-concentrating hormone receptor 1," J. Med. Chem. (2006) 49(24):7095-7107.
Thompson, H.W. et al., "Stereochemical control of reductions. 9. Haptophilicity studies with 1,1-disubstituted 2-methyleneacenaphthenes," J. Org. Chem. (2002) 67(9):2813-2825.
Thomson, J.F., "Physiological effects of D20 in mammals," Annals of the N.Y. Academy of Sci. (1960) 84:736-744.
Ting, P.C. et al., "The synthesis of substituted bipiperidine amide compounds as CCR3 antagonists," Bioorg. Med. Chem. Lett. (2005) 15(5):1375-1378.
Tsai, G. et al., "Gene knockout of glycine transporter 1: characterization of the behavioral phenotype," PNAS (2004) 101(22):8485-8490.
Ungureanu, I. et al., "The reactivity of N-tosylpheny-laziridine versus N-tosylphenylazetidine in heterocyclization reactions," Tetra. Lett. (2001) 42:6087-6091.
Vogel, S. et al., "Palladium-catalyzed intramolecular allylic alkylation of alpha-sulfinyl carbanions: a new asymmetric route to enantiopure gamma-lactams," Tetra. Lett. (2010) 51(11):1459-1461.
White, J.D. et al., "Catalyzed asymmetric diels-alder reaction of benzoquinone. Total synthesis of (−)-ibogamine," Org. Lett. (2000) 2(15):2373-2376.
Zhao, Z. et al., "Synthesis and SAR of GlyT1 inhibitors derived from a series of N-((4-(morpholine-4-carbonyl)-1-(propylsulfonyl) piperidin-4-yl) methyl) benzamindes," Bioorg. Med. Chem. Lett. (2006) 16(23):5968-5972.
Zhou, D. et al., "Studies toward the discovery of the next generation of antidepressants. Part 5: 3,4-dihydro-2H-benzo[1,4]oxazine derivatives with dual 5-HT1A receptor and serotonin transporter affinity," Bioorg. Med. Chem. Lett. (2006) 16(5):1338-1341.
United States Patent Office Notice of Allowance for U.S. Appl. No. 12/706,326 dated Jun. 11, 2013 (10 pages).
United States Patent Office Notice of Allowance for U.S. Appl. No. 12/706,326 dated Feb. 21, 2013 (9 pages).
United States Patent Office Action for U.S. Appl. No. 12/706,326 dated Sep. 21, 2012 (7 pages).
United States Patent Office Notice of Allowance for U.S. Appl. No. 12/666,629 dated Dec. 11, 2012 (5 pages).
United States Patent Office Action for U.S. Appl. No. 12/666,629 dated Jul. 5, 2012 (11 pages).
United States Patent Office Notice of Allowance for U.S. Appl. No. 12/706,321 dated Sep. 30, 2013 (10 pages).
United States Patent Office Action for U.S. Appl. No. 12/706,321 dated Jul. 19, 2012 (7 pages).
United States Patent Office Action for U.S. Appl. No. 12/706,321 dated Mar. 27, 2012 (11 pages).
United States Patent Office Notice of Allowance for U.S. Appl. No. 12/933,326 dated Jan. 9, 2014 (2 pages).
United Statse Patent Office Notice of Allowance for U.S. Appl. No. 12/933,326 dated Dec. 9, 2013 (4 pages).
United States Patent Office Notice of Allowance for U.S. Appl. No. 12/933,326 dated Oct. 1, 2013 (8 pages).
United States Patent Office Notice of Allowance for U.S. Appl. No. 12/933,326 dated Jan. 11, 2013 (5 pages).
United States Patent Office Action for U.S. Appl. No. 12/933,326 dated Oct. 29, 2012 (6 pages).
United States Patent Office Notice of Allowance for U.S. Appl. No. 13/206,937 dated Feb. 21, 2014 (9 pages).
United States Patent Office Action for U.S. Appl. No. 13/206,937 dated Aug. 28, 2013 (6 pages).
United States Patent Office Notice of Allowance for U.S. Appl. No. 13/206,937 dated May 15, 2014 (9 pages).
United States Patent Office Action for U.S. Appl. No. 13/206,750 dated Feb. 19, 2014 (6 pages).
United States Patent Office Notice of Allowance for U.S. Appl. No. 13/206,750 dated Nov. 7, 2014 (8 pages).
United States Patent Office Notice of Allowance for U.S. Appl. No. 13/207,030 dated Mar. 7, 2014.
United States Patent Office Notice of Allowance for U.S. Appl. No. 13/207,030 dated May 13, 2014 (9 pages).
United States Patent Office Notice of Allowance for U.S. Appl. No. 13/207,160 dated Mar. 17, 2014 (9 pages).
United States Patent Office Notice of Allowance for U.S. Appl. No. 13/207,160 dated Jun. 6, 2014 (9 pages).
United States Patent Office Action for U.S. Appl. No. 13/546,434 dated Apr. 14, 2014 (12 pages).
United States Patent Office Notice of Allowance for U.S. Appl. No. 13/546,434 dated Jan. 16, 2015 (9 pages).
United States Patent Office Action for U.S. Appl. No. 13/566,051 dated Sep. 16, 2013 (15 pages).
United States Patent Office Notice of Allowance for U.S. Appl. No. 13/566,051 dated May 29, 2014 (8 pages).
United States Patent Office Action for U.S. Appl. No. 13/680,488 dated Dec. 5, 2013 (17 pages).
United States Patent Office Action for U.S. Appl. No. 13/680,488 dated Jun. 21, 2013 (43 pages).
United States Patent Office Notice of Allowance for U.S. Appl. No. 13/680,488 dated Apr. 28, 2014 (13 pages).
United States Patent Office Corrected Notice of Allowance for U.S. Appl. No. 13/680,488 dated Jun. 12, 2014 (7 pages).
United States Patent Office Action for U.S. Appl. No. 13/789,967 dated Apr. 1, 2014 (11 pages).
United States Patent Office Action for U.S. Appl. No. 14/317,104 dated Nov. 5, 2014 (11 pages).
United States Patent Office Notice of Allowance for U.S. Appl. No. 14/317,104 dated Apr. 15, 2015 (9 pages).
United States Patent Office Action for U.S. Appl. No. 13/792,105 dated Apr. 16, 2014 (6 pages).
United States Patent Office Notice of Allowance for U.S. Appl. No. 13/792,105 dated Oct. 2, 2014 (10 pages).

(56) References Cited

OTHER PUBLICATIONS

United States Patent Office Action for U.S. Appl. No. 14/031,265 dated Apr. 15, 2014 (14 pages).
United States Patent Office Notice of Allowance for U.S. Appl. No. 14/031,265 dated Jan. 27, 2015 (11 pages).
United States Patent Office Action for U.S. Appl. No. 14/282,712 dated Oct. 3, 2014 (12 pages).
United States Patent Office Notice of Allowance for U.S. Appl. No. 14/282,712 dated Mar. 5, 2015 (9 pages).
United States Patent Office Action for U.S. Appl. No. 13/468,682 dated Sep. 10, 2014 (12 pages).
United States Patent Office Action for U.S. Appl. No. 13/468,682 dated Feb. 24, 2015 (7 pages).
United States Patent Office Action for U.S. Appl. No. 13/764,454 dated Sep. 30, 2014 (11 pages).
United States Patent Office Action for U.S. Appl. No. 13/764,454 dated Mar. 5, 2015 (8 pages).
United States Patent Office Action for U.S. Appl. No. 14/215,533 dated Jan. 2, 2015 (17 pages).
United States Patent Office Action for U.S. Appl. No. 14/216,222 dated Jan. 2, 2015 (17 pages).
International Search Report for Application No. PCT/EP2010/051903, mailed May 26, 2010.
International Search Report for Application No. PCT/EP2008/061007 dated Aug. 10, 2009 (6 pages).
International Search Report for Application No. PCT/EP2009/053800 dated Nov. 20, 2009 (6 pages).
International Search Report for Application No. PCT/EP2012/058760 dated Aug. 27, 2012 (4 pages).
International Search Report for Application No. PCT/EP2012/065294 dated Sep. 21, 2012 (4 pages).
International Search Report and Writeen Opinion for Application No. PCT/EP2014/055159 dated Jun. 16, 2014.
International Search Report and Written Opinion for Application No. PCT/EP2014/072235 dated Dec. 15, 2014.
International Search Report and Written Opinion for Application No. PCT/EP2014/072233 dated Jan. 20, 2015.
Written Opinion for Application No. PCT/EP2010/051903, mailed Aug. 16, 2011.
Written Opinion for Application No. PCT/EP2008/061007 dated Aug. 10, 2009 (7 pages).
Written Opinion for Application No. PCT/EP2009/053800 dated Nov. 20, 2009 (7 pages).
Written Opinion for Application No. PCT/EP2012/058760 dated Aug. 27, 2012 (4 pages).
United States Patent Office Notice of Allowance for U.S. Appl. No. 14/317,104 dated Sep. 3, 2015 (9 pages).
United States Patent Office Notice of Allowance for U.S. Appl. No. 14/282,712 dated Sep. 11, 2015 (9 pages).
Database Registry Chemical Abstracts Service, Columbus, Ohio, Accession No. RN 1381576-56-2, Entered STN: Jul. 5, 2012.
Database Registry Chemical Abstracts Service, Columbus, Ohio, Accession No. RN 1394552-70-5, Entered STN: Sep. 18, 2012.
Damasio, A.R., "Alzheimer's disease and related dementias," Cecil Textbook of Medicine, 20th Edition (1996) 2:1992-1996.
FDA mulls drug to slow late-stage Alzheimer's [online], retrieved on Sep. 23, 2003 from the Internet URL: http://www.cnn.com120031HEALTH/conditions/O91241alzheimers.drug.aplindexhtml.
Layzer, R.B., "Degenerative diseases of the nervous system," Section Five, Cecil Textbook of Medicine, 20th Edition (1996) 2:2050-2057.
United States Patent Office Action for U.S. Appl. No. 13/764,454 dated Jun. 4, 2015 (12 pages).
United States Patent Office Action for U.S. Appl. No. 14/215,533 dated Jul. 7, 2015 (13 pages).
United States Patent Office Action for U.S. Appl. No. 14/216,222 dated Jul. 6, 2015 (13 pages).
United States Patent Office Action for U.S. Appl. No. 13/468,682 dated Jul. 24, 2015 (7 pages).

* cited by examiner

AMINOCHROMANE, AMINOTHIOCHROMANE AND AMINO-1,2,3,4-TETRAHYDROQUINOLINE DERIVATIVES, PHARMACEUTICAL COMPOSITIONS CONTAINING THEM, AND THEIR USE IN THERAPY

CROSS-REFERENCE TO RELATED APPLICATIONS

This claims priority to U.S. Patent Application No. 61/892,203, filed on Oct. 17, 2013, the en-tire contents of which are fully incorporated herein by reference.

BACKGROUND OF THE INVENTION

The present invention relates to aminochromane, aminothiochromane and amino-1,2,3,4-tetrahydroquinoline derivatives, pharmaceutical compositions comprising such aminochromane, aminothiochromane and amino-1,2,3,4-tetrahydroquinoline derivatives, and the use of such aminochromane, aminothiochromane and amino-1,2,3,4-tetrahydroquinoline derivatives for therapeutic purposes. The aminochromane, aminothiochromane and amino-1,2,3,4-tetrahydroquinoline derivatives are GlyT1 inhibitors.

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the WO-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxyl)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

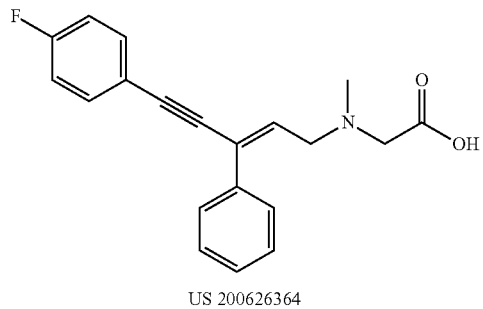

US 200626364

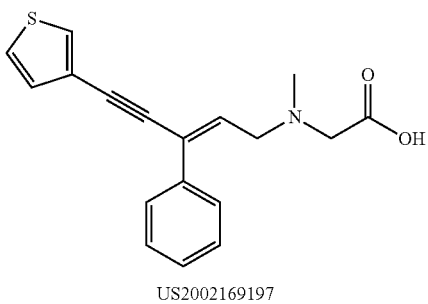

US2002169197

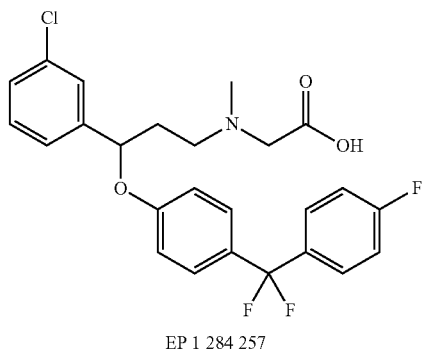

EP 1 284 257

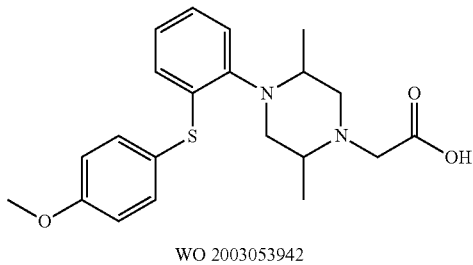

WO 2003053942

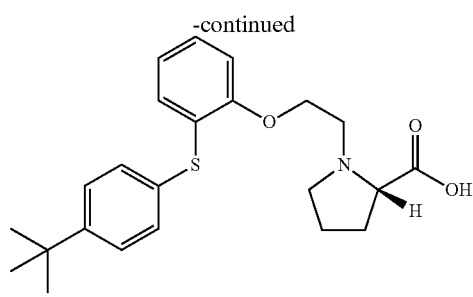
WO 2004096761
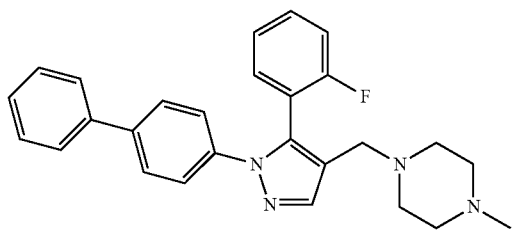
WO 2003031435
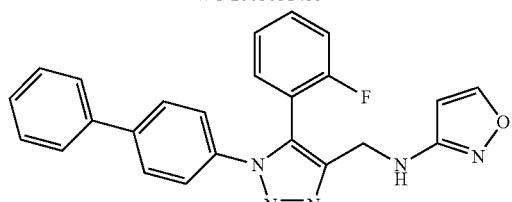
DE 10315570
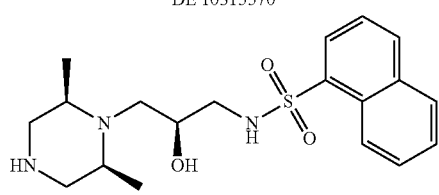
WO 2003055478
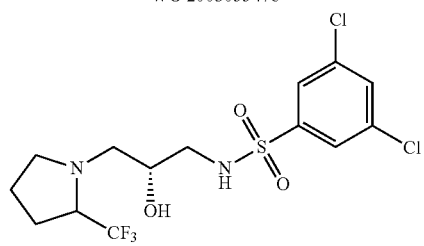
WO 2004113280
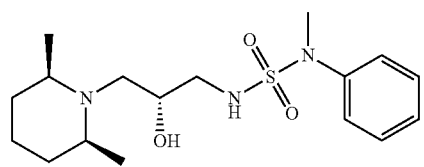
WO 2004112787
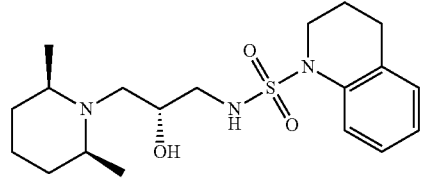
WO 2004113301
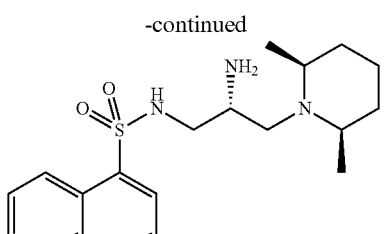
WO 2005049023
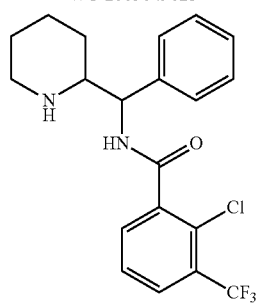
WO 2003089411
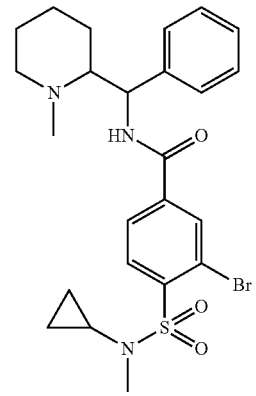
WO 2004013100
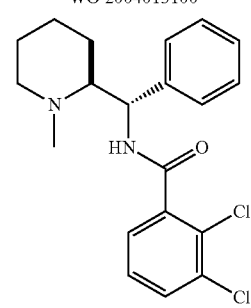
WO 2004013101
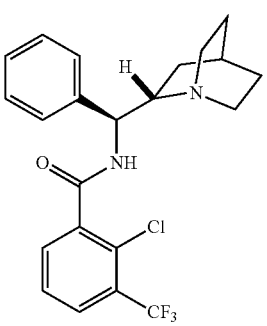
WO 2005037783

-continued
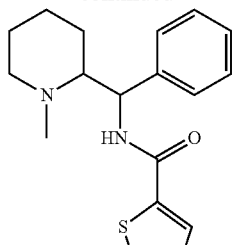
WO 2005037792
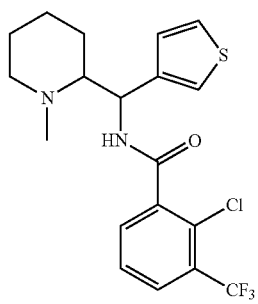
WO 2005037781
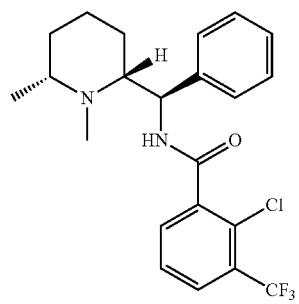
WO 2005037782
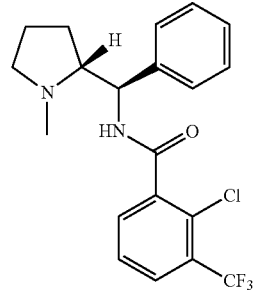
WO 2005037785
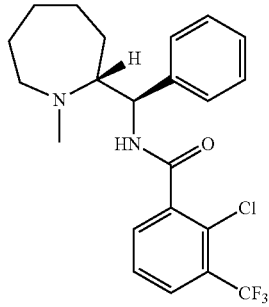
WO 2005037785
-continued
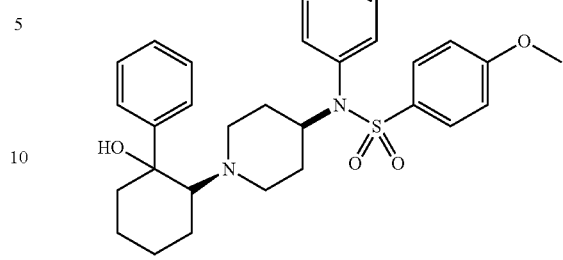
WO 2004072034
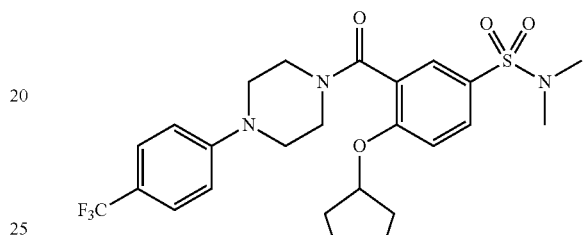
WO 2005014563
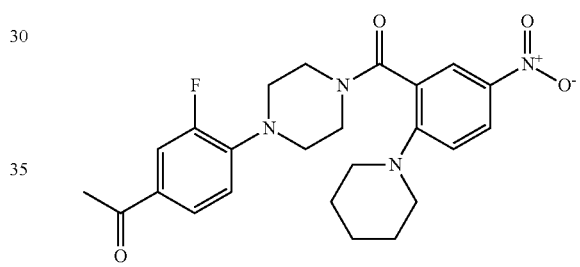
WO 2005023260
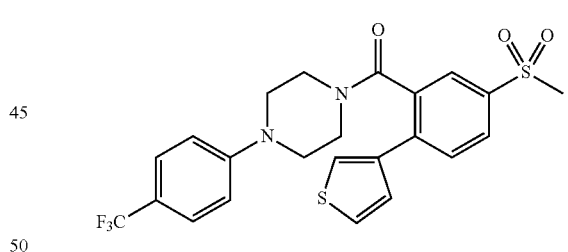
WO 2005023261
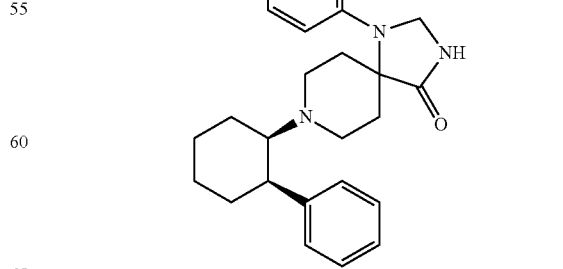
WO 2005040166

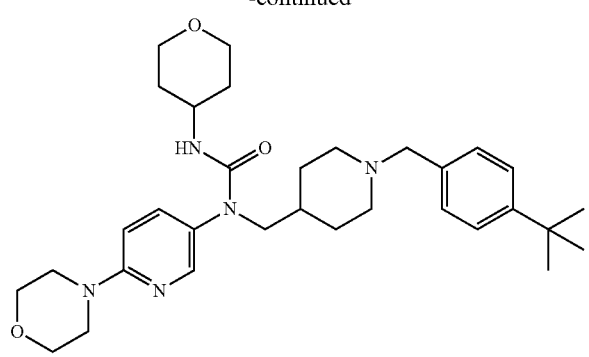

WO 2005058882

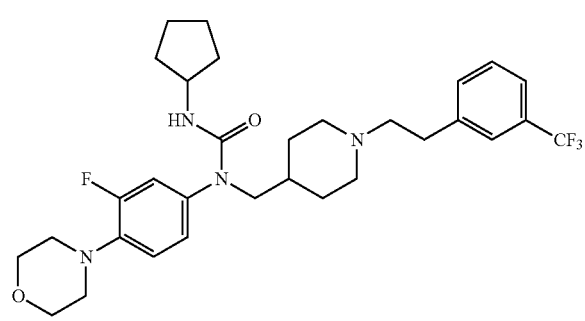

WO 2005058885

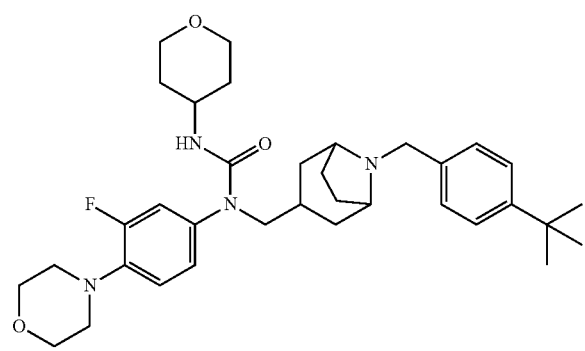

WO 2005058317

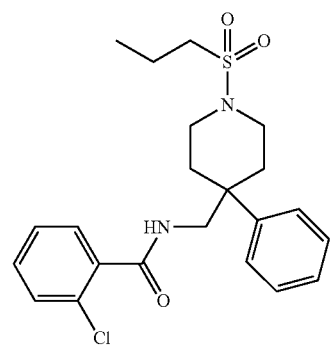

WO 2005046601

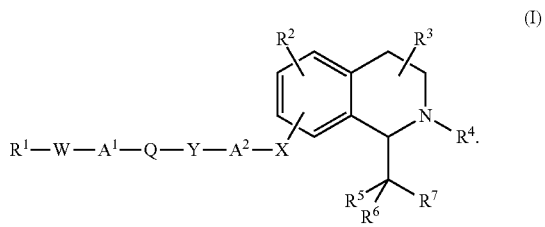

WO 2003087086

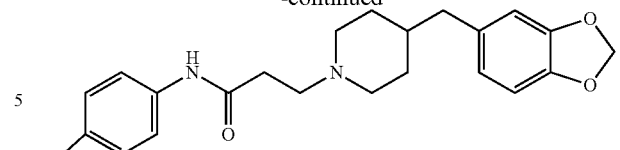

WO2003076420

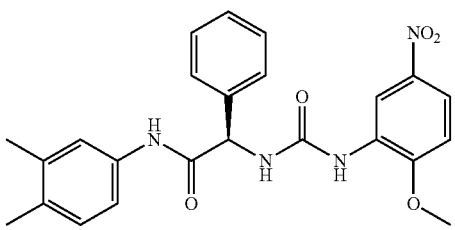

WO2004022528

(see also Hashimoto K., Recent patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

Further glycine transporter inhibitors are known from the following documents.

WO 2009024611 describes 4-benzylaminoquinolines of formula:

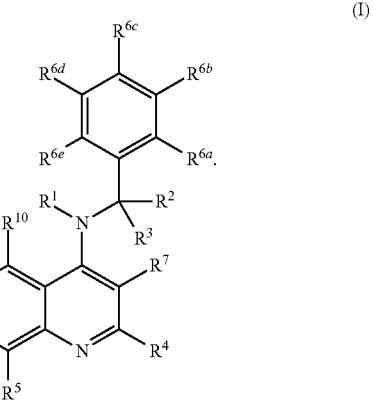

(I)

WO 2009121872 describes tetrahydroisoquinoline of formula:

(I)

R$^1$—W—A$^1$—Q—Y—A$^2$—X

WO 2010092180 describes aminotetraline derivatives of formula:

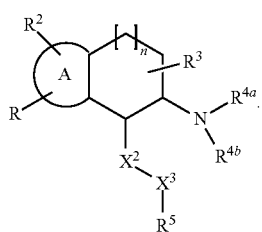
(I)

WO 2010092181 describes heterocyclic compounds of formula:

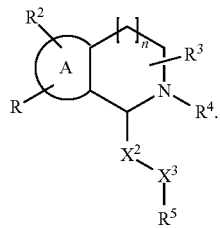
(I)

WO 2012020131 describes aminoindane derivatives of formula:

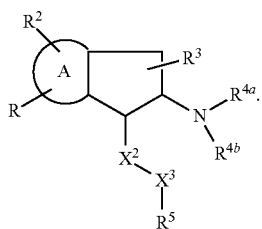
(I)

WO 2012020130 describes phenalkylamine derivatives of formula:

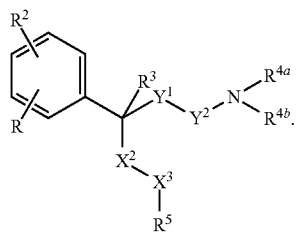
(I)

WO 2012020133 describes tetraline and indane derivatives of formula:

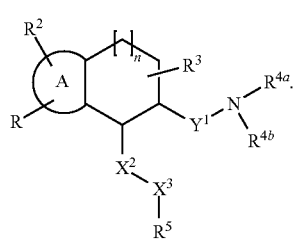
(I)

WO 2012152915 describes benzazepine derivatives of formula:

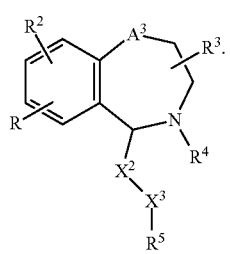
(I)

WO 2012020134 describes phenalkylamine derivatives of formulae:

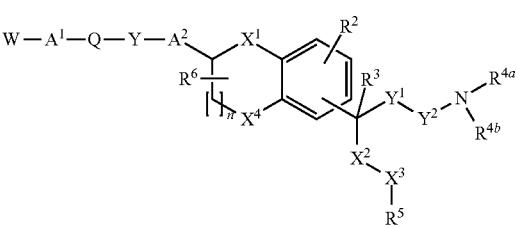
(I)

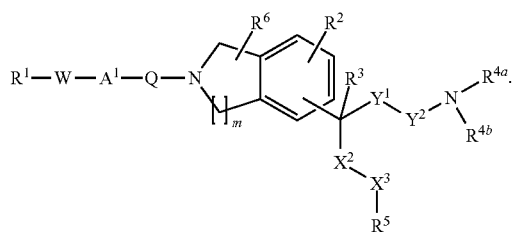
(II)

WO 2013020930 describes aminochromane, aminothiochromane and amino-1,2,3,4-tetrahydroquinoline derivatives of formula:

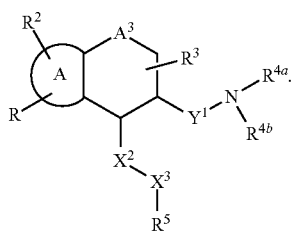
(I)

WO 2013072520 describes N-substituted aminobenzocycloheptene, aminotetraline, aminoindane and phenalkylamine derivatives of formula:

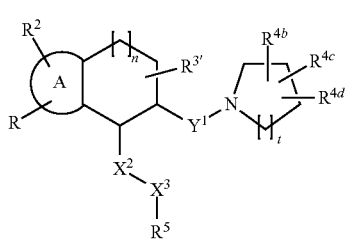
(I)

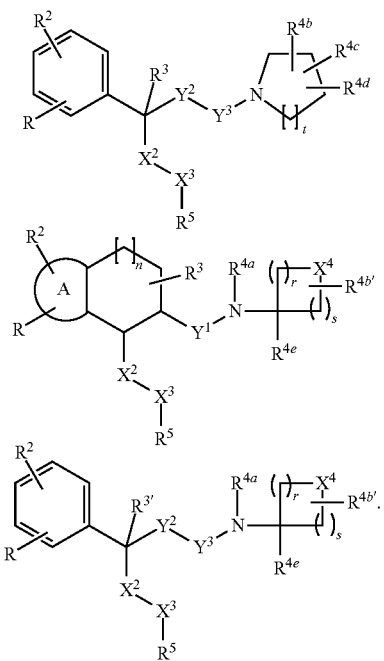

WO 2013120835 describes isoindoline derivatives of formula

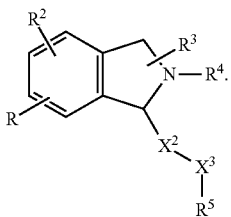

It was one object of the present invention to provide further glycine transporter inhibitors. It was a further object of the present invention to provide glycine transporter inhibitors which combine high stability with high affinity. It was a further object of the present invention to provide glycine transporter inhibitors which show favorable efflux properties. It was a further object of the present invention to provide glycine transporter inhibitors which combine high stability and high affinity with favorable efflux properties.

SUMMARY OF THE INVENTION

The present invention relates to aminochromane, aminothiochromane and amino-1,2,3,4-tetrahydroquinoline derivatives of the formula (I)

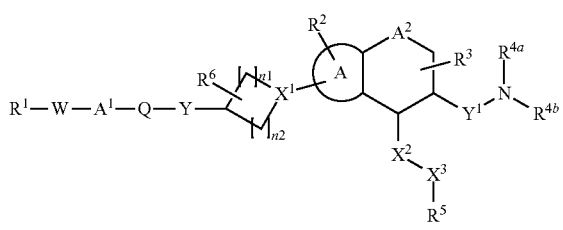

wherein
A is a 5- or 6-membered ring;
$R^1$ is hydrogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl)aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, hydroxyalkoxy, alkoxy-alkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di-(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;
W is —$NR^7$— or a bond;
$A^1$ is optionally substituted alkylene or a bond;
Q is —$S(O)_2$— or —$C(O)$—;
Y is —$NR^8$— or a bond;
n1 is 0, 1, 2, or 3;
n2 is 0, 1, 2, or 3;
$X^1$ is >N— or >CH—;
$R^6$ is hydrogen, halogen, alkyl, halogenated alkyl, —CN, hydroxy, alkoxy or halogenated alkoxy, or two radicals $R^6$ together with the carbon atom to which they are attached form a carbonyl group;
$R^2$ is hydrogen, halogen, alkyl, halogenated alkyl, —CN, alkenyl, alkynyl, optionally substituted aryl, hydroxy, alkoxy, halogenated alkoxy, alkoxycarbonyl, alkenyloxy, arylalkoxy, alkylcarbonyloxy, alkylthio, alkylsulfinyl, alkylsulfonyl, aminosulfonyl, amino, alkylamino, alkenylamino, nitro or optionally substituted heterocyclyl, or two radicals $R^2$ together with the ring atoms of A to which they are bound form a 5- or 6 membered ring;
$A^2$ is —O—, —S— or —$NR^9$—;
$R^3$ is hydrogen, halogen, alkyl or alkoxy, or two radicals $R^3$ together with the carbon atom to which they are attached form a carbonyl group;
$Y^1$ is a bond or optionally substituted alkylene;
$R^{4a}$ is hydrogen, alkyl, cycloalkylalkyl, halogenated alkyl, hydroxyalkyl, alkoxyalkyl, aminoalkyl, —$CH_2CN$, arylalkyl, optionally substituted cycloalkyl, —CHO, alkylcarbonyl, (halogenated alkyl)carbonyl, arylcarbonyl, alkoxycarbonyl, aryloxycarbonyl, alkylaminocarbonyl, alkenyl, —C(=NH)$NH_2$, —C(=NH)NHCN, alkylsulfonyl, arylsulfonyl, amino, —NO or optionally substituted heterocyclyl; or
$R^{4a}$ is optionally substituted alkylene that is bound to a carbon atom in $Y^1$;
$R^{4b}$ is hydrogen, alkyl, halogenated alkyl, hydroxyalkyl, alkoxyalkyl, aminoalkyl, —$CH_2CN$, —CHO, alkylcarbonyl, (halogenated alkyl)carbonyl, arylcarbonyl, alkoxycarbonyl, aryloxycarbonyl, alkylaminocarbonyl, alkenyl, —C(=NH)NH$_2$, —C(=NH)NHCN, alkylsulfonyl, arylsulfonyl, amino, —NO or heterocyclyl; or R$^{4a}$, R$^{4b}$ together are optionally substituted alkylene, wherein one —CH$_2$— of alkylene may be replaced by an oxygen atom or —NR$^{10}$;

X$^2$ is —O—, —NR$^{11a}$—, —S—, >CR$^{12a}$R$^{12b}$ or a bond;
X$^3$ is —O—, —NR$^{11b}$—, —S—, >CR$^{13a}$R$^{13b}$ or a bond;
R$^5$ is optionally substituted aryl, optionally substituted cycloalkyl or optionally substituted heterocyclyl;
R$^7$ is hydrogen or alkyl;
R$^8$ is hydrogen, alkyl, cycloalkyl, aminoalkyl, optionally substituted arylalkyl or heterocyclyl; or
R$^8$, R$^1$
together are alkylene;
R$^9$ is hydrogen, alkyl, cycloalkylalkyl, halogenated alkyl, hydroxyalkyl, alkoxyalkyl, aminoalkyl, CH$_2$CN, arylalkyl, cycloalkyl, —CHO, alkylcarbonyl, (halogenated alkyl)carbonyl, arylcarbonyl, alkoxycarbonyl, aryloxycarbonyl, alkylaminocarbonyl, alkenyl, —C(=NH)NH$_2$, —C(=NH)NHCN, alkylsulfonyl, arylsulfonyl, amino, —NO or heterocyclyl;
R$^{10}$ is hydrogen or alkyl;
R$^{11a}$ is hydrogen or alkyl;
R$^{11b}$ is hydrogen or alkyl;
R$^{12a}$ is hydrogen, optionally substituted alkyl, alkylaminoalkyl, dialkylaminoalkyl, heterocyclylalkyl, optionally substituted aryl or hydroxy;
R$^{12b}$ is hydrogen or alkyl, or
R$^{12a}$, R$^{12b}$
together with the carbon atom to which they are attached form a carbonyl or are optionally substituted alkylene, wherein one —CH$_2$— of alkylene may be replaced by an oxygen atom or —NR$^{14}$—;
R$^{13a}$ is hydrogen, optionally substituted alkyl, alkylaminoalkyl, dialkylaminoalkyl, heterocyclylalkyl, optionally substituted aryl or hydroxy;
R$^{13b}$ is hydrogen or alkyl,
R$^{13a}$, R$^{13b}$
together with the carbon atom to which they are attached form a carbonyl or are optionally substituted alkylene, wherein one —CH$_2$— of alkylene may be replaced by an oxygen atom or —NR$^{15}$—;
R$^{14}$ is hydrogen or alkyl; and
R$^{15}$ is hydrogen or alkyl,
or a physiologically tolerated salt thereof.

Thus, the terms aminochromane, aminothiochromane and amino-1,2,3,4-tetrahydroquinoline derivatives are used herein to denote in particular aminochromanes (A$^2$ is —O—), thiochromanes (A$^2$ is —S—) and 1,2,3,4-tetrahydroquinolines (A$^2$ is —NR$^9$—) as well as fused tetrahydropyranes, tetrahydrothiopyranes and tetrahydropyridines wherein the benzene ring of the chromanes, thiochromanes and 1,2,3,4-tetrahydroquinolines is replaced by a 5- or 6-membered heterocyclic ring.

Said compounds of formula (I), i.e., the aminochromane, aminothiochromane and amino-1,2,3,4-tetrahydroquinoline derivatives of formula (I) and their physiologically tolerated salts, are glycine transporter inhibitors and thus useful as pharmaceuticals. Compounds of formula (I) combine high metabolic stability with high affinity. Compounds of formula (I) show favorable efflux properties which may lead to enhanced oral bioavailability and/or increased brain availability. Compounds of formula (I) combine high metabolic stability and high affinity with favorable efflux properties.

The present invention thus further relates to the compounds of formula (I) for use in therapy.

The present invention also relates to pharmaceutical compositions which comprise a carrier and a compound of formula (I).

In particular, said compounds, i.e., the aminochromane, aminothiochromane and amino-1,2,3,4-tetrahydroquinoline derivatives and their physiologically tolerated salts, are inhibitors of the glycine transporter GlyT1.

The present invention thus further relates to the compounds of formula (I) for use in inhibiting the glycine transporter GlyT1.

The present invention also relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder.

The present invention further relates to the compounds of formula (I) for use in treating pain.

The present invention also relates to the use of the compounds of formula (I) in the manufacture of a medicament for treating a neurologic or psychiatric disorder and corresponding methods of treating said disorders. The present invention also relates to the use of the compounds of formula (I) in the manufacture of a medicament for treating pain and corresponding methods of treating pain.

DETAILED DESCRIPTION OF THE INVENTION

Provided that the aminochromane, aminothiochromane and amino-1,2,3,4-tetrahydroquinoline derivatives of the formula (I) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) and/or of their salts.

According to one embodiment, an enantiomer of the compounds of the present invention has the following formula:

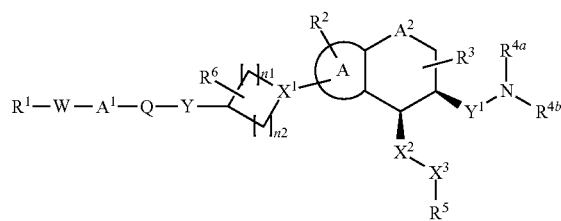

wherein R$^1$, W, A$^1$, Q, Y, R$^6$, n1, n2, X$^1$, A, R$^2$, A$^2$, R$^3$, Y$^1$, R$^{4a}$, R$^{4b}$, X$^2$, X$^3$, R$^5$, are as defined herein.

According to another embodiment, an enantiomer of the compounds of the present invention has the following formula:

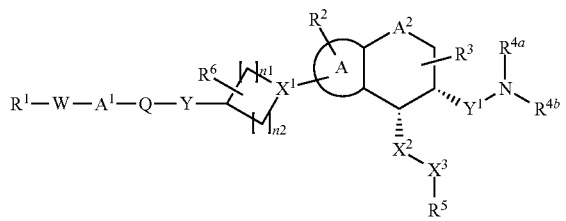

wherein $R^1$, W, $A^1$, Q, Y, $R^6$, n1, n2, $X^1$, A, $R^2$, $A^2$, $R^3$, $Y^1$, $R^{4a}$, $R^{4b}$, $X^2$, $X^3$, $R^5$ are as defined herein.

According to one embodiment, an enantiomer of the compounds of the present invention has the following formula:

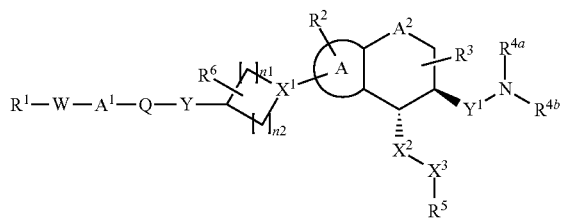

wherein $R^1$, W, $A^1$, Q, Y, $R^6$, n1, n2, $X^1$, A, $R^2$, $A^2$, $R^3$, $Y^1$, $R^{4a}$, $R^{4b}$, $X^2$, $X^3$, $R^5$ are as defined herein.

According to another embodiment, an enantiomer of the compounds of the present invention has the following formula:

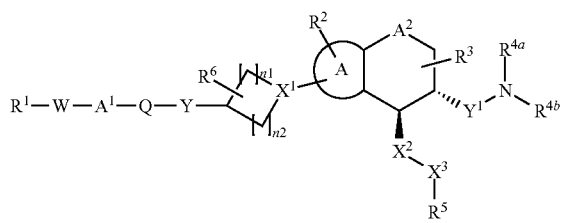

wherein $R^1$, W, $A^1$, Q, Y, $R^6$, n1, n2, $X^1$, A, $R^2$, $A^2$, $R^3$, $Y^1$, $R^{4a}$, $R^{4b}$, $X^2$, $X^3$, $R^5$ are as defined herein.

The physiologically tolerated salts of the aminochromane, aminothiochromane and amino-1,2,3,4-tetrahydroquinoline derivatives of the formula (I) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhauser Verlag, Basel and Stuttgart, 1966. The physiologically tolerated salts of the aminochromane, aminothiochromane and amino-1,2,3,4-tetrahydroquinoline derivatives also include salts of a physiologically tolerated anion with aminochromane, aminothiochromane and amino-1,2,3,4-tetrahydroquinoline derivatives wherein one or more than one nitrogen atom is quaternized, e.g. with an alkyl residue (e.g. methyl or ethyl).

The present invention moreover relates to compounds of formula (I) as defined herein, wherein at least one of the atoms has been replaced by its stable, non-radioactive isotope (e.g., hydrogen by deuterium $^{12}$C by $^{13}$C, $^{14}$N by $^{15}$N, $^{16}$O by $^{18}$O) and preferably wherein at least one hydrogen atom has been replaced by a deuterium atom.

Of course, such compounds contain more of the respective isotope than this naturally occurs and thus is anyway present in the compounds (I).

Stable isotopes (e.g., deuterium, $^{13}$C, $^{15}$N, $^{18}$O) are non-radioactive isotopes which contain one or more additional neutron than the normally abundant isotope of the respective atom. Deuterated compounds have been used in pharmaceutical research to investigate the in vivo metabolic fate of the compounds by evaluation of the mechanism of action and metabolic pathway of the non-deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic Press, London, 1985; Kato et al., J. *Labelled Comp. Radiopharmaceut.*, 36(10): 927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physico-chemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$-$C_m$ indicates in each case the possible number of carbon atoms in the group. The prefix $M_n$-$M_m$ indicates in each case the possible number of ring forming atoms (ring members) in the group.

Unless indicated otherwise, the term "substituted" means that a radical is substituted with 1, 2 or 3, especially 1, substituent which, according to a particular embodiment of the invention, are independently selected from the group consisting of halogen, $C_1$-$C_4$-alkyl, $C_3$-$C_6$-aryl-$C_1$-$C_4$-alkyl, halogenated-$C_1$-$C_4$-alkyl, hydroxy-$C_1$-$C_4$-alkyl, hydroxy-(halogenated $C_1$-$C_4$-alkoxy-$C_1$-$C_4$ alkyl, amino-$C_1$-$C_4$-alkyl, $M_3$-$M_{12}$-heterocyclyl-$C_1$-$C_4$-alkyl, $C_3$-$C_7$-cycloalkyl, $C_2$-$C_4$-alkenyl, —CN, —$CO_2H$, $C_1$-$C_4$-alkoxycarbonyl, aminocarbonyl, $C_1$-$C_4$-alkylaminocarbonyl, (di-$C_1$-$C_4$-alkylamino)carbonyl, $C_6$-$C_{12}$-arylaminocarbonyl, $M_3$-$M_{12}$-heterocyclylaminocarbonyl, $C_6$-$C_{12}$-aryl, oxo (=O), OH, $C_1$-$C_4$-alkoxy, halogenated-$C_1$-$C_4$-alkoxy, $C_3$-$C_7$-cycloalkoxy, carboxy-$C_1$-$C_4$-alkoxy, $C_6$-$C_{12}$-aryl-$C_1$-$C_4$-alkoxy, $C_6$-$C_{12}$-aryloxy, $M_3$-$M_{12}$-heterocyclyl-$C_1$-$C_4$-alkoxy, SH, $C_1$-$C_4$-alkylthio, $C_1$-$C_4$-alkylsulfonyl, $C_1$-$C_4$-alkylaminosulfonyl, di-$C_1$-$C_4$-alkylaminosulfonyl, $C_3$-$C_6$-arylsulfonyl, aminosulfonyl, $C_3$-$C_6$-arylaminosulfonyl, -$M_{12}$-heterocyclylaminosulfonyl, $NH_2$, $C_1$-$C_4$-alkylamino, di-$C_1$-$C_4$-alkylamino, $C_6$-$C_{12}$-aryl-$C_1$-$C_4$-alkylamino, $C_1$-$C_4$-alkylcarbonylamino, $C_6$-$C_{12}$-arylcarbonylamino, $M_3$-$M_{12}$-heterocyclylcarbonylamino, $C_1$-$C_6$-alkylsulfonylamino, $C_6$-$C_{12}$-arylsulfonylamino, $M_3$-$M_{12}$-heterocyclylsulfonylamino and $M_3$-$M_{12}$-heterocyclyl, wherein aryl and heterocyclyl may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or isopropyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3- dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_6$-alkyl is a straight-chain or branched alkyl group having 1 to 6 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_6$ alkyl groups as defined, such as trifluoromethyl.

$C_3$-$C_{12}$-Cycloalkyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a cycloaliphatic radical having from 3 to 12 carbon atoms such as in cyclopropylmethyl, cyclobutylmethyl, cyclopentylmethyl and cyclohexylmethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, iso-butylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, iso-propylaminocarbonylaminomethyl, n-butylaminocarbonylaminomethyl, 2-butylaminocarbonylaminomethyl, iso-butylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonylaminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethyl-sulfonylaminomethyl, n-propylsulfonylaminomethyl, iso-propylsulfonylaminomethyl, n-butylsulfonylaminomethyl, 2-butylsulfonylaminomethyl, iso-butylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$M_3$-$M_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $M_3$-$M_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

$C_1$-$C_6$-Alkylcarbonyl is a radical of the formula R—C(O)—, wherein R is an alkyl radical having from 1 to 6, preferably 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butyloxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl(2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_4$-Alkylene is straight-chain or branched alkylene group having from 1 to 4 carbon atoms. Examples include methylene and ethylene. A further example is propylene.

$C_2$-$C_6$-Alkylene is straight-chain or branched alkylene group having from 2 to 6 carbon atoms. Examples include ethylene. A further example is propylene.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, iso-butoxy(2-methylpropoxy), tert.-butoxy pentyloxy, 1-methylbutoxy, 2-methylbutoxy, 3-methylbutoxy, 2,2-dimethylpropoxy, 1-ethylpropoxy, hex-yloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, iso-propylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, iso-propylcarbonylaminomethoxy, n-butylcarbonylaminomethoxy, 2-butylcarbonylaminomethoxy, iso-butylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(iso-butylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, iso-propoxycarbonylaminomethoxy, n-butoxycarbonylaminomethoxy, 2-butoxycarbonylaminomethoxy, iso-butoxycarbonylaminomethoxy, tert-butoxycarbonylaminomethoxy, 2-(methoxycarbonylamino)ethoxy, 2-(ethoxycarbonyl-amino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(iso-butoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy(2-propen-1-yloxy), 1-propen-1-yloxy, 2-propen-2-yloxy, methallyloxy(2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$M_3$-$M_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $M_3$-$M_{12}$-heterocyclylsulfonylamino group as defined herein. Examples include 2-(pyridin-3-yl-sulfonylamino)ethoxy.

$M_3$-$M_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $M_3$-$M_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$M_3$-$M_{12}$-Heterocyclyloxy is a radical of the formula R—O—, wherein R is a $M_3$-$M_{12}$-heterocyclyl group having from 3 to 12, in particular from 3 to 7 ring forming atoms (ring members) as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$M_3$-$M_{12}$-Heterocyclylsulfonyl is a radical of the formula R—S(O)$_2$—, wherein R is $M_3$-$M_{12}$-heterocyclyl as defined herein.

Aminosulfonyl is $NH_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, iso-propylaminosulfonyl, n-butylaminosulfonyl, 2-butylaminosulfonyl, iso-butylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is $NH_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido(methylcarbonylamino), propionamido, n-butyramido, 2-methylpropionamido(isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino(2-propen-1-ylamino), 1-propen-1-ylamino, 2-propen-2-ylamino, methallylamino(2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, iso-propylsulfonylamino, n-butylsulfonylamino, 2-butylsulfonylamino, iso-butylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$M_3$-$M_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $M_3$-$M_{12}$-heterocyclyl include:

C- or N-bound 3-4-membered, saturated rings, such as 2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyn-ol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3- dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetra-hydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as
2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as
1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl(4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic.

These include quinolinyl, isoquinolinyl, indolyl, indolizinyl, isoindolyl, indazolyl, benzofuryl, benzthienyl, benzo[b]thiazolyl, benzoxazolyl, benzodioxol, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, chromenyl and chromanyl.

$M_3$-$M_{12}$-Heteroarylene is a heteroaryl diradical. Examples include pyrid-2,5-ylene and pyrid-2,4-ylene.

With respect to the compounds' capability of inhibiting glycine transporter 1, the variables $R^1$, W, $A^1$, Q, Y, $R^6$, n1, n2, $X^1$, A, $R^2$, $A^2$, $R^3$, $Y^1$, $R^{4a}$, $R^{4b}$, $X^2$, $X^3$, $R^5$ have in particular the following meanings which, when taken alone or in combination, represent particular embodiments of the compounds of the formula (I) or any other formula disclosed herein.

In said formula (I), there may be one or more than one substituent $R^2$, $R^3$, $R^6$ and one or more than one substituent

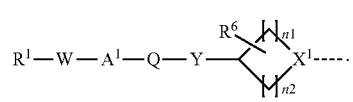

More particularly, there may be up to 3 substituents $R^2$, up to 4 substituents $R^3$, and up to 6 substituents $R^6$. Preferably, there is one substituent

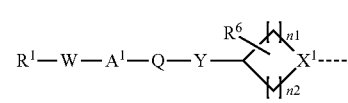

and 1, 2 or 3 substituents $R^2$. Formula (I) may thus be depicted as follows:

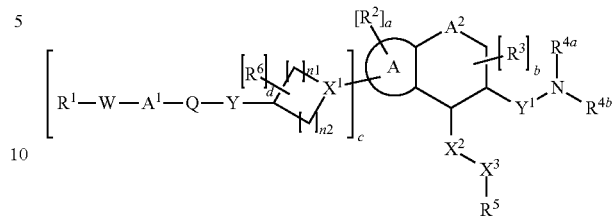

wherein A, $R^1$, W, $A^1$, Q, Y, $R^6$, n1, n2, $X^1$, $R^2$, $A^2$, $R^3$, $Y^1$, $R^{4a}$, $R^{4b}$, $X^2$, $X^3$ and $R^5$ are as defined herein, a is 1, 2 or 3, b is 1, 2, 3 or 4, c is 1 and d is 1, 2, 3, 4, 5 or 6. If there is more than one radical $R^2$, these may be the same or different radicals. If there is more than one radical $R^3$, these may be the same or different radicals. If there is more than one radical $R^6$, these may be the same or different radicals. According to one embodiment, a is 1, b is 1 or 2, c is 1, and d is 1 or 2.

In the following the radical

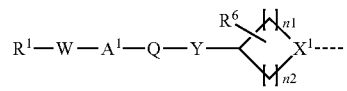

is also referred to as R.

A is a 5- or 6-membered ring which includes two carbon atoms from the tetrahydropyrane, tetrahydrothiopyrane and tetrahydropyridine moiety to which A is fused. A may be a homocyclic or heterocyclic ring. The ring may be saturated, unsaturated non-aromatic or aromatic. According to a particular embodiment, A is a benzene ring. As a heterocyclic ring, A may include 1, 2 or 3 heteroatoms as ring member atoms, which are selected, independently of each other from N, S and O. Preferred heterocyclic rings comprise 1 nitrogen atom as ring member atom and optionally 1 or 2 further heteroatoms as ring members, which are selected, independently of each other from O, S and N. Likewise preferred heterocyclic rings comprise 1 heteroatom as ring member atom, which is selected from O, S and N, and optionally 1 or 2 further nitrogen atoms as ring member atoms. According to a particular embodiment, A is a heterocyclic ring selected from the group consisting of the following 5- or 6-membered heterocyclic rings:

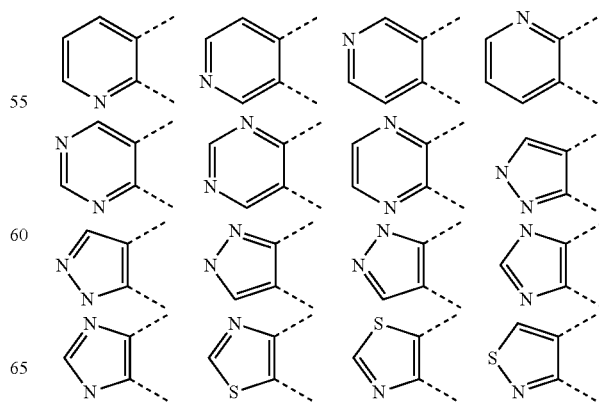

-continued

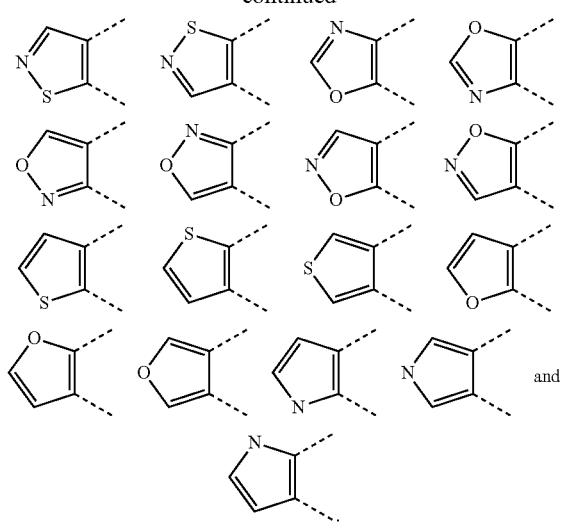

In said formulae, hydrogen atoms are not depicted. This is meant to illustrate that the free valency of a carbon or nitrogen atom may be either bound to a hydrogen atom, to R or to $R^2$. Accordingly, R and $R^2$ may be C- or N-bound at any position of ring A.

The skilled person will appreciate that some of the rings depicted above may be represented with a different structure, e.g. with hydrogen atoms having other positions than those shown above, for instance as given in the following structures:

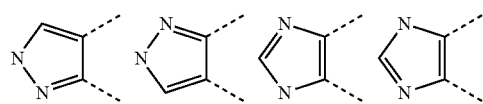

Preferably, A is a heterocyclic ring selected from the group consisting of the following 5- or 6-membered heterocyclic rings:

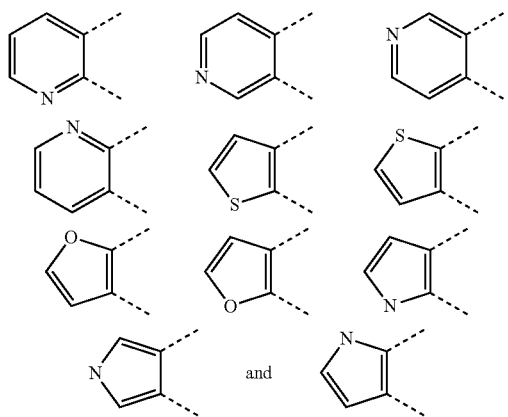

If ring A is a 5-membered heterocyclic ring it is preferred that R is bound to $G^1$ or $G^2$, in particular $G^2$:

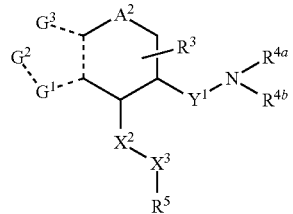

In said formula, $G^1$, $G^2$ and $G^3$ independently are —CH=, —CH$_2$—, —N=, —NH—, S or O, at least one of $G^1$, $G^2$ and $G^3$ is —CH= or —CH$_2$—, the dotted line represents a single or a double bond and $A^2$, $R^3$, $Y^1$, $R^{4a}$, $R^{4b}$, $X^2$, $X^3$, $R^5$ are as defined herein.

If ring A is 6-membered heterocyclic ring it is preferred that R is bound to $G^1$ or $G^2$, in particular $G^2$:

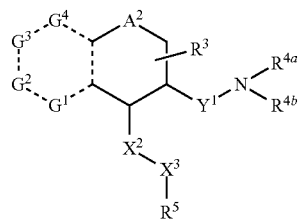

In said formula, $G^1$, $G^2$, $G^3$ and $G^4$ independently are —CH=, —CH$_2$—, —N=, —NH—, S or O, at least one of $G^1$, $G^2$, $G^3$ and $G^4$ is —CH= or —CH$_2$—, the dotted line represents a single or a double bond and $A^2$, $R^3$, $Y^1$, $R^{4a}$, $R^{4b}$, $X^2$, $X^3$, $R^5$ are as defined herein.

Heterocyclic compounds having the following partial structures are preferred:

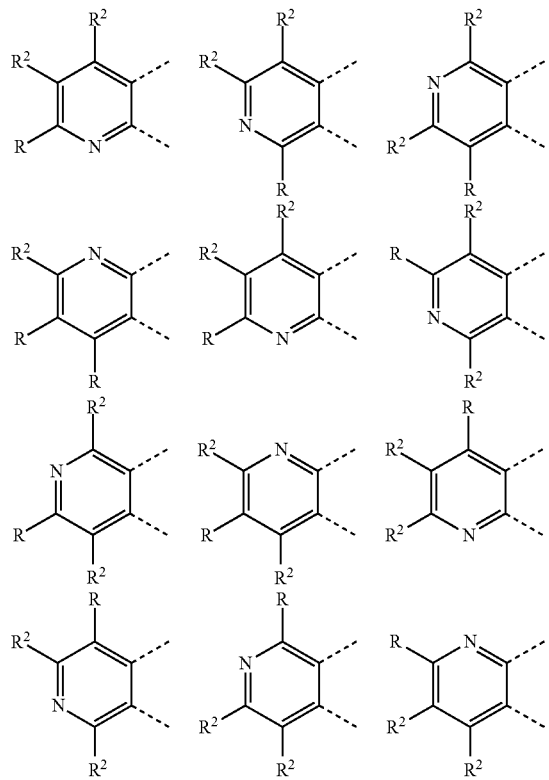

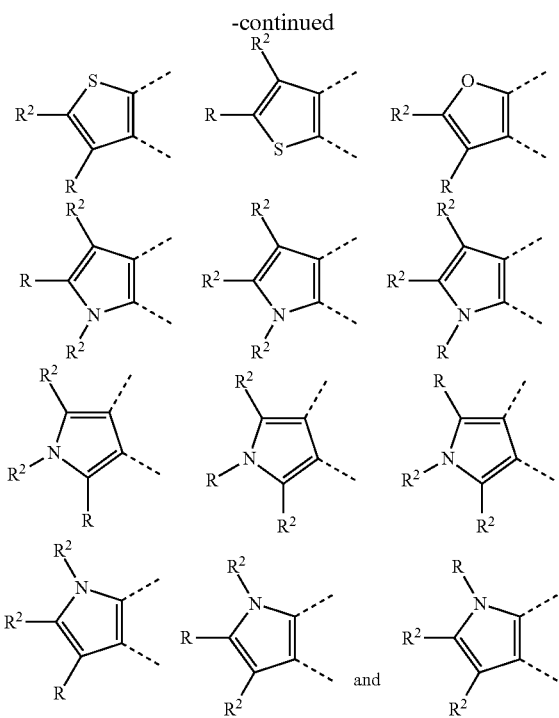

Heterocyclic compounds having the following partial structures are particularly preferred:

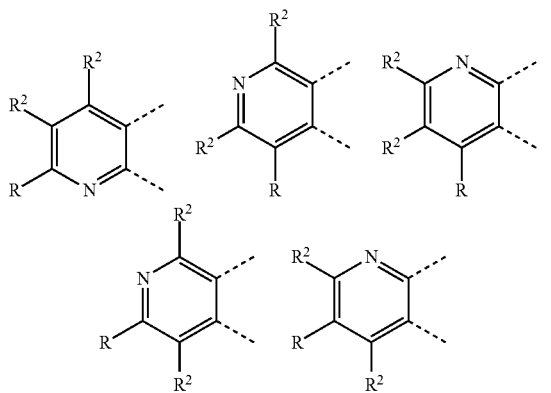

In said formulae, R and $R^2$ are as defined herein. If there is more than one radical $R^2$, these may be the same or different radicals.

$R^1$ is hydrogen, $C_1$-$C_6$-alkyl (e.g. methyl, ethyl, n-propyl, isopropyl, n-butyl, sec-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), hydroxy-$C_1$-$C_4$-alkyl, $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $M_3$-$M_{12}$-heterocyclyl-$C_1$-$C_4$-alkyl, $C_3$-$C_{12}$-cycloalkyl (e.g. cyclopropyl or cyclobutyl), $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl (e.g. prop-1,2-en-1-yl), $C_2$-$C_6$-alkynyl, optionally substituted $C_6$-$C_{12}$-aryl (e.g. phenyl, 2-methylphenyl), hydroxy, $C_1$-$C_6$-alkoxy (e.g. tert-butyloxy), halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $M_3$-$M_{12}$-heterocyclylsulfonylamino-$C_1$-$C_4$-alkoxy, $M_3$-$M_{12}$-heterocyclyl-$C_1$-$C_4$-alkoxy, $C_6$-$C_{12}$-aryloxy, $M_3$-$M_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino (e.g. dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $M_3$-$M_{12}$-heterocyclyl (e.g. 3-pyridyl, 2-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1,3-dimethyl-1,2-diazol-4-yl, 1, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl, 3-pyrrolidinyl, 1-methyl-pyrrol-3-yl, 2-pyridyl, 1-methyl-1,2-diazol-3-yl, 1-methyl-3-trifluoromethyl-1,2-diazol-4-yl, 1,2-dimethyl-1,3-diazol-4-yl, 5-methylisoxazol-3-yl, 1-methyl-1,2,4-triazol-3-yl, 1-methyl-1,2,3-triazol-4-yl, 1-ethyl-1,2,3-triazol-4-yl, furan-3-yl, 5-methyl-furan-2-yl, 2,5-dimethyl-furan-3-yl, 3-methyl-piperidinyl, thiophen-2-yl, 4-methyl-thiophen-2-yl, 5-methyl-thiophen-2-yl, thiophen-3-yl, or morpholin-4-yl).

Preferably, $R^1$ is $C_1$-$C_6$-alkyl (e.g. methyl, ethyl, n-propyl, isopropyl, sec-butyl, n-butyl or n-pentyl), $C_3$-$C_{12}$-cycloalkyl-$C_1$-$C_4$-alkyl (e.g. cyclopropylmethyl, cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), hydroxy, $C_1$-$C_6$-alkylamino, (halogenated $C_1$-$C_6$-alkyl)amino, di-$C_1$-$C_6$-alkylamino or optionally substituted $M_3$-$M_{12}$-heterocyclyl (e.g. 3-pyridyl, 2-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1,3-dimethyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl, 1-methyl-1,2,3-triazol-4-yl, 1-ethyl-1,2,3-triazol-4-yl, 3-pyrrolidinyl, furan-3-yl, 5-methyl-furan-2-yl, 2,5-dimethyl-furan-3-yl, 3-methyl-piperidinyl, thiophen-2-yl, 4-methyl-thiophen-2-yl, 5-methyl-thiophen-2-yl, thiophen-3-yl, or morpholin-4-yl).

More preferably, $R^1$ is $C_1$-$C_6$-alkyl (e.g. ethyl, n-propyl, isopropyl, 2-butyl), $C_3$-$C_{12}$-cycloalkyl-$C_1$-$C_4$-alkyl (e.g. cyclopropylmethyl), $C_3$-$C_{12}$-cycloalkyl (e.g. cyclobutyl), or optionally substituted $M_3$-$M_{12}$-heterocyclyl (e.g. 3-pyridyl, 2-pyridyl, 1-methyl-1,2-diazol-4-yl, 1,3-dimethyl-1,2-diazol-4-yl, 1-ethyl-1,2-diazol-4-yl, 1-methyl-1,3-diazol-4-yl, 1-methyl-1,2,3-triazol-4-yl, 1-ethyl-1,2,3-triazol-4-yl, 3-oxetanyl, 1-methyl-pyrrol-3-yl, furan-3-yl, 5-methyl-furan-2-yl, 2,5-dimethyl-furan-3-yl, 3-methyl-piperidinyl, thiophen-2-yl, 4-methyl-thiophen-2-yl, 5-methyl-thiophen-2-yl, thiophen-3-yl, or morpholin-4-yl).

According to a particular embodiment, $R^1$ is $C_1$-$C_6$-alkyl (e.g. ethyl, n-propyl, isopropyl, 2-butyl), $C_3$-$C_{12}$-cycloalkyl-$C_1$-$C_4$-alkyl (e.g. cyclopropylmethyl), or $C_3$-$C_{12}$-cycloalkyl (e.g. cyclobutyl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholinyl and piperidinyl. The same applies to substituted $C_6$-$C_{12}$-aryl in substituted $C_6$-$C_{12}$-aryl-$C_1$-$C_4$-alkyl.

In connection with $R^1$, substituted $M_3$-$M_{12}$-heterocyclyl in particular includes $M_3$-$M_{12}$-heterocyclyl, such as pyridyl, thienyl, diazolyl, quinolinyl, furanyl, thiophenyl, piperidinyl, piperazinyl or morpholinyl, pyrrolyl, isoxazolyl and triazolyl being further examples of such $M_3$-$M_{12}$-heterocyclyl, substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $M_3$-$M_{12}$-heterocyclyl (e.g., morpholinyl or piperidinyl). The same applies to substituted $M_3$-$M_{12}$-heterocyclyl in substituted $M_3$-$M_{12}$-heterocyclyl-$C_1$-$C_4$-alkyl.

W is —$NR^7$— or a bond. Y is —$NR^8$— or a bond. According to one embodiment, W is —$NR^7$— and Y is a bond. According to an alternative embodiment, W is a bond and Y is —$NR^8$—. According to a further alternative embodiment, W is a bond and Y is a bond, especially if $R^1$ is a nitrogen-bound radical, e.g. nitrogen-bound heterocyclyl such as piperazinyl or morpholinyl.

Q is —$S(O)_2$— or —C(O)—. According to one embodiment, Q is —$S(O)_2$—, especially if Y is —$NR^8$—. According to a preferred embodiment, -Q-Y— is —$S(O)_2$—$NR^8$—.

According to a particular embodiment, —W-$A^1$-Q-Y— is —W-$A^1$-$S(O)_2$—$NR^8$—, —$NR^7$—$S(O)_2$—, -$A^1$-$S(O)_2$— or —$S(O)_2$—. According to a further particular embodiment, —W-$A^1$-Q-Y— is —W-$A^1$-CO—$NR^8$— or —$NR^7$—CO—.

$A^1$ is optionally substituted $C_1$-$C_4$-alkylene or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably $NR^7$—.

According to a particular embodiment, $R^1$—W-$A^1$-Q-Y— is $R^1$—$S(O)_2$—NH—, $R^1$—NH—$S(O)_2$—, $R^1$—C(O)—NH— or $R^1$—NH—C(O)—.

According to a further particular embodiment, W is a bond and $A^1$ is a bond.

The index n1 is 0, 1, 2, or 3. Preferably, n1 is 1, 2 or 3. In particular, n1 is 1 or 2.

The index n2 is 0, 1, 2, or 3. Preferably, n2 is 1, 2 or 3. In particular, n2 is 1 or 2.

According to a particular embodiment, at least one of n1 and n2 is 1, 2, or 3.

The following examples of cyclic moieties illustrate combinations of n1 and n2:

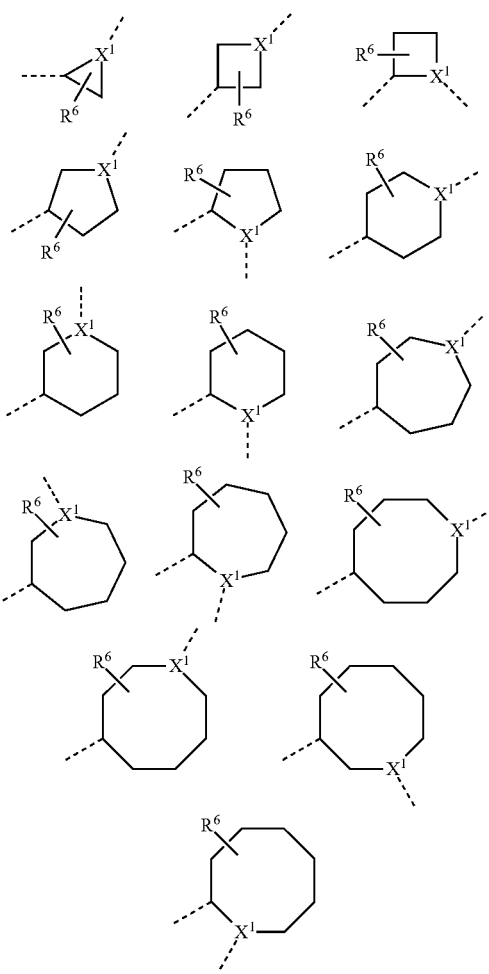

wherein $X^1$ and $R^6$ are as defined herein.

According to a further particular embodiment, the sum of n1 and n2 is 2, 3, or 4.

According to a further particular embodiment, combinations of n1 and n2 include n1=1, n2=1; n1=1, n2=2; n1=2, n2=1; n1=2, n2=2; n1=1, n2=3; or n1=3, n2=1.

According to one embodiment, $X^1$ is >N—. According to an alternative embodiment, $X^1$ is >CH—.

The following examples of cyclic moieties illustrate preferred combinations of n1, n2 and $X^1$:

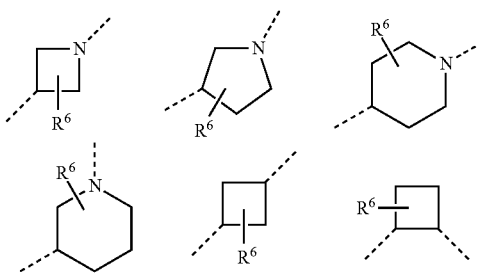

-continued

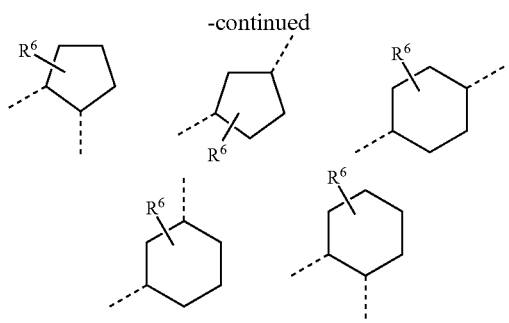

wherein R$^6$ is as defined herein.

More preferred combinations of n1, n2 and X$^1$ include cyclic moieties where n1 is 1, n2 is 1 and X$^1$ is ->N—; n1 is 1, n2 is 1 and X$^1$ is >CH—; n1 is 1, n2 is 2 and X$^1$ is ->N—; n1 is 1, n2 is 2 and X$^1$ is >CH—; n1 is 2, n2 is 1 and X$^1$ is ->N—; n1 is 2, n2 is 1 and X$^1$ is >CH—; n1 is 2, n2 is 2 and X$^1$ is ->N—, n1 is 2, n2 is 2 and X$^1$ is >CH—; n1 is 1, n2 is 3 and X$^1$ is ->N—; n1 is 1, n2 is 3 and X$^1$ is >CH—; n1 is 3, n2 is 1 and X$^1$ is ->N—; or n1 is 3, n2 is 1 and X$^1$ is >CH—.

The cyclic moieties may thus be depicted by the following formulae:

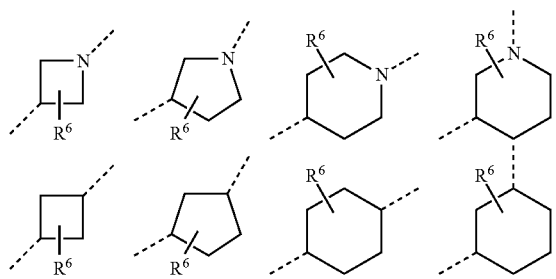

wherein R$^6$ is as defined herein.

Particularly preferred combinations of n1, n2 and X$^1$ include moieties where n1 is 1, n2 is 1 and X$^1$ is ->N— (azetidinyl); or n1 is 1, n2 is 1 and X$^1$ is >CH— (cyclobutyl).

The substituents R$^1$—W-A$^1$-Q-Y— and -A on the cyclic moiety can be cis- or trans-configuration as depicted by the following formula:

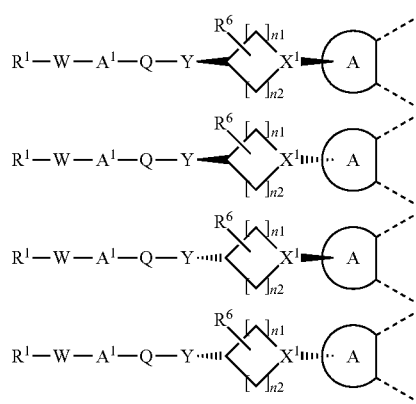

wherein R$^1$, W, A$^1$, Q, Y, R$^6$, n1, n2, X$^1$ and A are as defined herein.

According to a particular embodiment, the substituents R$^1$—W-A$^1$-Q-Y— and -A are in trans-configuration.

In formula (I), there may be one or more than one radical R$^6$. More particularly, there may be up to 6 radicals R$^6$. Preferably, there may be up to 4 radical R$^6$. In particular, there may be one or 2 radicals R$^6$. If there is more than one radical R$^6$, these may be the same or different radicals. The compounds of the invention may therefore be represented by the following formula:

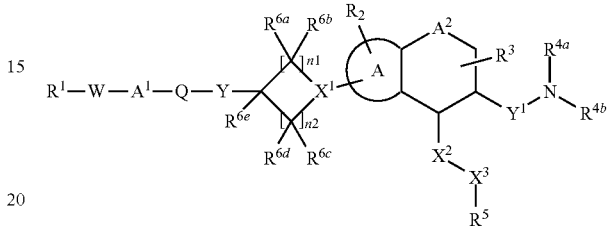

wherein R$^{6a}$, R$^{6b}$, R$^{6c}$, R$^{6d}$, R$^{6e}$ independently have one of the meanings given for R$^6$, and A, R$^1$, W, A$^1$, Q, Y, R$^6$, X$^1$, n1, n2, R$^2$, A$^2$, R$^3$, Y$^1$, R$^{4a}$, R$^{4b}$, X$^2$, X$^3$, R$^5$ are as defined herein (with X$^1$ being >N— or >CR$^{6f}$— and R$^{6f}$ having one of the meanings given for R$^6$).

According to a particular embodiment, the compounds of the invention have the following formula:

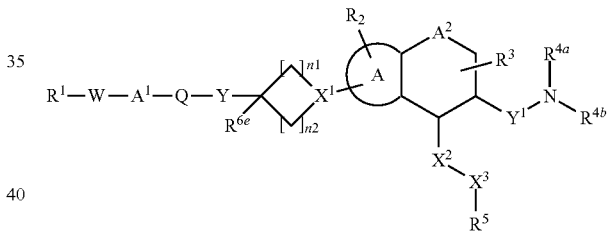

wherein R$^{6e}$ has one of the meanings given for R$^6$, and A, R$^1$, A$^1$, Q, Y, R$^6$, X$^1$, n1, n2, R$^2$, A$^2$, R$^3$, Y$^1$, R$^{4a}$, R$^{4b}$, X$^2$, X$^3$, R$^5$ are as defined herein.

R$^6$ is hydrogen, halogen (e.g. fluorine), C$_1$-C$_4$-alkyl (e.g. methyl or ethyl), halogenated C$_1$-C$_4$-alkyl (e.g. 1,1,1-trifluorometh-1-yl), —CN, hydroxy, C$_1$-C$_6$-alkoxy (e.g. methoxy), or halogenated C$_1$-C$_6$-alkoxy.

According to an alternative embodiment, two R$^6$ together with the carbon atom to which they are bound may form a carbonyl.

The following examples of cyclic moieties illustrate combinations of n1, n2 and R$^6$, wherein two R$^6$ together with the carbon atom to which they are bound form a carbonyl:

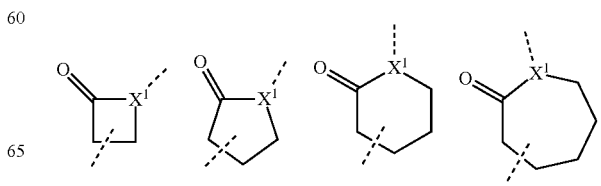

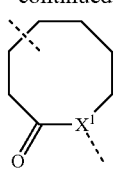

The following examples of cyclic moieties illustrate particular combinations of n1, n2 and $R^6$, wherein two $R^6$ together with the carbon atom to which they are bound form a carbonyl:

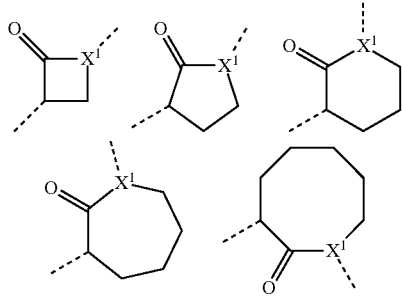

The following examples of cyclic moieties illustrate preferred combinations of n1, n2, $X^1$ and $R^6$, wherein two $R^6$ together with the carbon atom to which they are bound form a carbonyl.

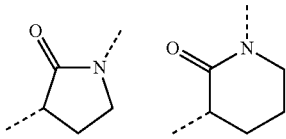

Preferably, $R^6$ is hydrogen or $C_1$-$C_4$-alkyl (e.g. methyl, ethyl). In particular, $R^6$ is hydrogen.

If A is a benzene ring, the radical

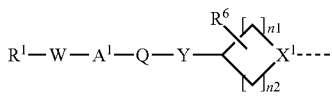

may, in principle, be bound to the 5-, 6-, 7- or 8-position of the skeleton of the compounds of the invention:

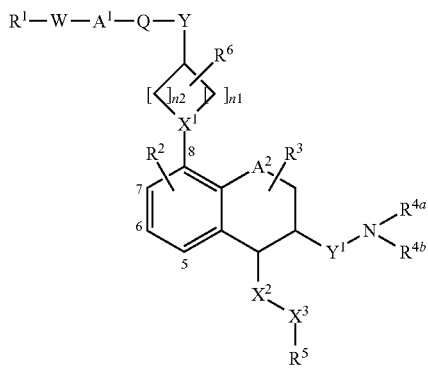

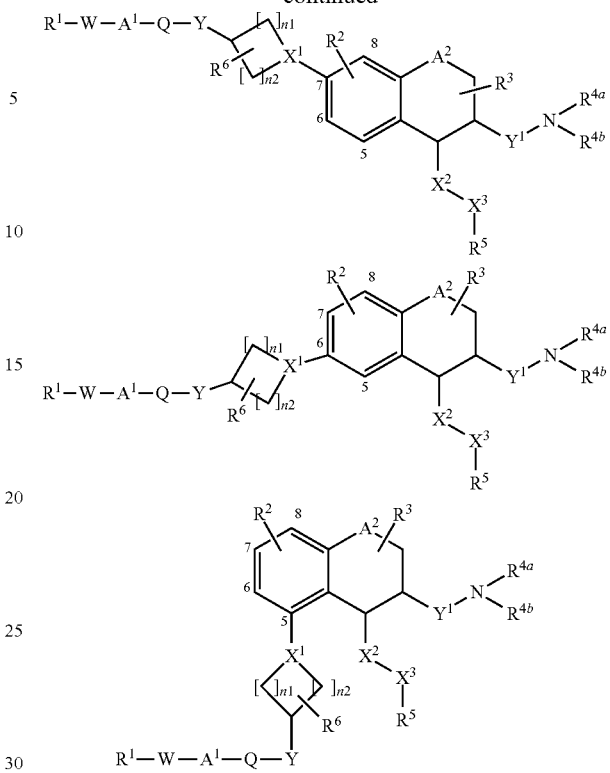

In said formulae, $R^1$, W, $A^1$, Q, Y, $R^6$, $X^1$, n1, n2, $R^2$, $A^2$, $R^3$, $Y^1$, $R^{4a}$, $R^{4b}$, $X^2$, $X^3$, $R^5$ are as defined herein.

Compounds of the invention having the radical

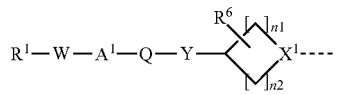

in the 5-, 6-, 7-position are preferred.

Particularly preferred are compounds of the invention having the radical

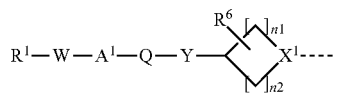

in the 6-position.

In addition to the radical

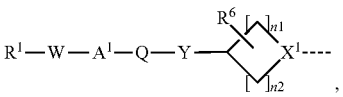

the compounds of the invention may have one or more than one further substituent bound to the ring A. In these positions, the skeleton of the compounds of the invention may thus be substituted with one or more than one radical $R^2$. If there is more than one radical $R^2$, these may be the same or different radicals. In particular, the skeleton of the compounds of the invention may be substituted with one or more than one radical $R^2$ in 5-, 6-, 7- and/or 8-position if A is a benzene ring. The compounds of the invention may therefore be represented by one of the following formulae:

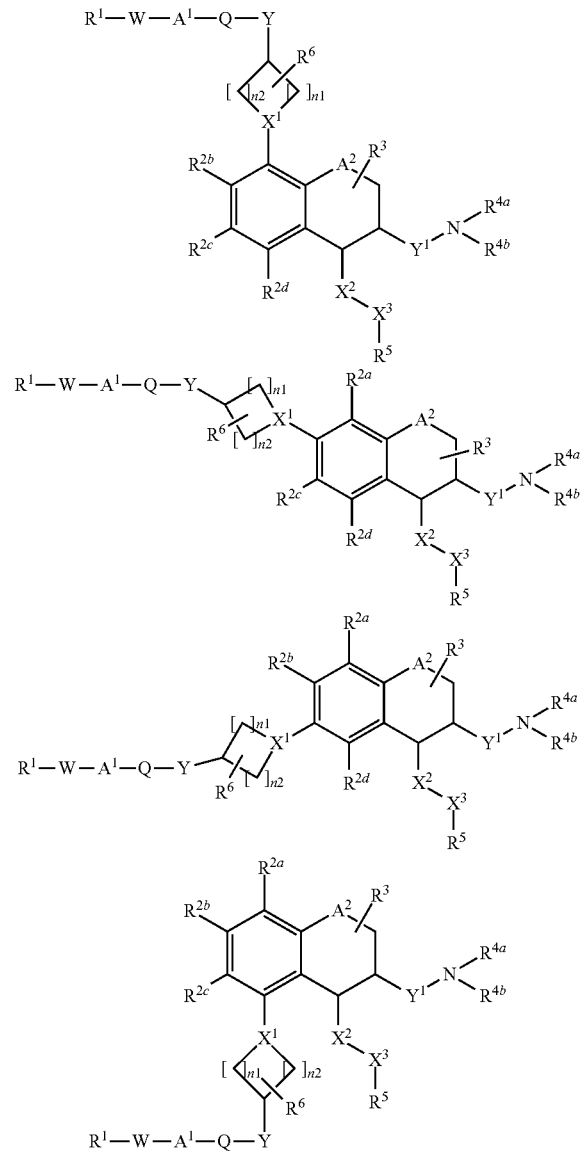

wherein $R^{2a}$, $R^{2b}$, $R^{2c}$, $R^{2d}$ independently have one of the meanings given for $R^2$, and $R^1$, W, $A^1$, Q, Y, $R^6$, $X^1$, n1, n2, $R^2$, $A^2$, $R^3$, $Y^1$, $R^{4a}$, $R^{4b}$, $X^2$, $X^3$, $R^5$ are as defined herein.

$R^2$ is hydrogen, halogen (e.g. fluorine), $C_1$-$C_6$-alkyl, halogenated $C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $M_3$-$M_{12}$-heterocyclyl, or two radicals $R^2$ together with the ring atoms of A to which they are bound form a 5- or 6 membered ring.

An optionally substituted 5- or 6-membered ring that is formed by two radicals $R^2$ together with the ring atoms of A to which they are bound is, for instance, a benzene ring.

In connection with $R^2$, substituted $C_6$-$C_{12}$-aryl in particular includes $C_6$-$C_{12}$-aryl, such as phenyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

In connection with $R^2$, substituted $M_3$-$M_{12}$-heterocyclyl in particular includes $M_3$-$M_{12}$-heterocyclyl, such as morpholinyl, pyrrolidinyl and piperidinyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

Preferably, $R^2$ is hydrogen, halogen (e.g. fluorine), CN or $C_1$-$C_6$-alkoxy. In particular, $R^2$ is hydrogen or halogen (e.g. fluorine).

According to a particular embodiment, the compounds of the invention have one of the following formulae:

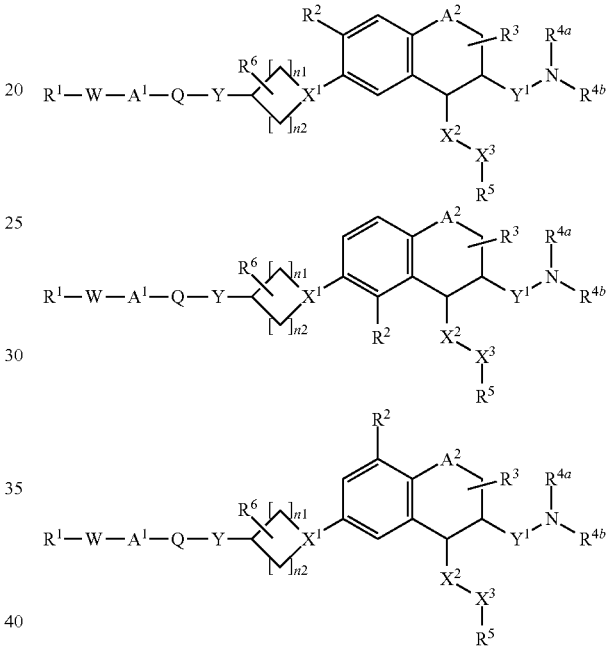

wherein $R^1$, W, $A^1$, Q, Y, $R^6$, n1, n2, $X^1$, $R^2$, $A^2$, $R^3$, $Y^1$, $R^{4a}$, $R^{4b}$, $X^2$, $X^3$ and $R^5$ are as defined herein.

$A^2$ is —O—, —S— or —$NR^9$—. According to a preferred embodiment, $A^2$ is —O—.

In 2-, 3- and/or 4-position, the compounds of the invention may be substituted with one or more than one radical $R^3$. If there is more than one radical $R^3$, these may be the same or different radicals. The compounds of the invention may therefore be represented by the following formula:

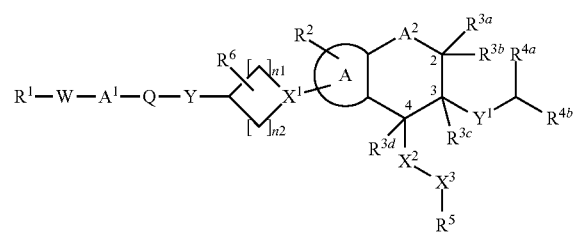

wherein $R^{3a}$, $R^{3b}$, $R^{3a}$, $R^{3d}$ independently have one of the meanings given for $R^3$, and A, $R^1$, W, $A^1$, Q, Y, $R^6$, n1 n2, $X^1$, $R^2$, $A^2$, $R^3$, $Y^1$, $R^{4a}$, $R^{4b}$, $X^2$, $X^3$, $R^5$ are as defined herein.

According to a particular embodiment, the compounds of the invention have one of the following formulae:

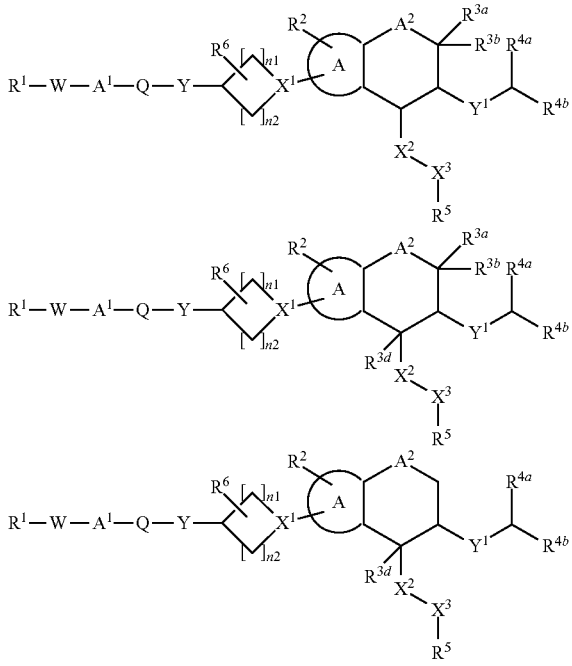

wherein $R^{3a}$, $R^{3b}$, $R^{3d}$ independently have the meaning of $R^3$ and A, $R^1$, W, $A^1$, Q, Y, $R^6$, n1, n2, $X^1$, $R^2$, $A^2$, $R^3$, $Y^1$, $R^{4a}$, $R^{4b}$, $X^2$, $X^3$, $R^5$ are as defined herein.

$R^3$ is hydrogen, halogen, $C_1$-$C_6$-alkyl, $C_1$-$C_6$-alkoxy, or two radicals $R^3$ together with the carbon atom to which they are attached form a carbonyl group.

Preferably, $R^3$ is hydrogen or $C_1$-$C_6$-alkyl (e.g. methyl). In particular, $R^3$ is hydrogen.

$Y^1$ is a bond or optionally substituted $C_1$-$C_4$-alkylene (e.g. methylene or 1,2-ethylene). In connection with $Y^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, $C_3$-$C_{12}$-cycloalkyl and cyano. In particular, $Y^1$ is a bond.

$R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), hydroxy-$C_1$-$C_4$-alkyl, $C_1$-$C_6$-alkoxy-$C_1$-$C_4$-alkyl, amino-$C_1$-$C_4$-alkyl, —$CH_2CN$, $C_6$-$C_{12}$-aryl-$C_1$-$C_4$-alkyl (e.g. benzyl), optionally substituted $C_3$-$C_{12}$-cycloalkyl (e.g. cyclopropyl or cyclobutyl), —CHO, $C_1$-$C_4$-alkylcarbonyl (e.g. methylcarbonyl, ethylcarbonyl or isopropylcarbonyl), (halogenated $C_1$-$C_4$-alkyl)carbonyl (e.g. fluoromethylcarbonyl, difluoromethylcarbonyl, trifluoromethylcarbonyl, 1,1,1-trifluoroeth-2-ylcarbonyl or 1,1,1-trifluoroprop-3-ylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl), $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or optionally substituted $M_3$-$M_{12}$-heterocyclyl (e.g. 3-oxetanyl).

In connection with $R^{4a}$, substituted $C_3$-$C_{12}$-cycloalkyl in particular includes $C_3$-$C_{12}$-cycloalkyl such as cyclopropyl, cyclobutyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $M_3$-$M_{12}$-heterocyclyl.

In connection with $R^{4a}$, substituted $M_3$-$M_{12}$-heterocyclyl in particular includes $M_3$-$M_{12}$-heterocyclyl substituted with 1 or more substituents $R^{4g}$ and/or $R^{4b'}$. The compounds of the invention may therefore be represented by the following formula:

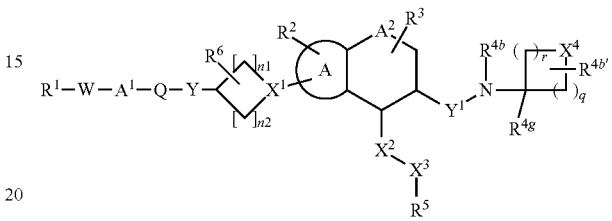

wherein A, $R^1$, W, $A^1$, Q, Y, $R^6$, n1, n2, $X^1$, $R^2$, $A^2$, $R^3$, $Y^1$, $R^{4b}$, $X^2$, $X^3$ and $R^5$ are as defined herein, $R^{4b'}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$ alkylamino $C_1$-$C_4$ alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, cyano; hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl, $R^{4g}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$ alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$ alkylamino $C_1$-$C_4$ alkyl, $C_1$-$C_6$-alkylcarbonylamino-$C_1$-$C_4$-alkyl, $C_1$-$C_6$- alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl, the index q is 1, 2 or 3; and in particular, q is 1 or 2,
the index r is 1, 2 or 3; and in particular, r is 1 or 2,
$X^4$ is —O—, —$NR^{17}$—, —S—, —S(O)—, —S(O)$_2$—, or a bond and preferable, $X^4$ is —O— or a bond, and $R^{17}$ is hydrogen, $C_1$-$C_6$-alkyl or $C_3$-$C_{12}$-cycloalkyl. Preferably, $R^{17}$ is hydrogen.

Particular combinations of q and r include moieties wherein q is 1 and r is 1, or q is 2 and r is 1.

Particular combinations of q, r and $X^4$ include moieties where q is 1, r is 1 and $X^4$ is —O— (oxetanyl); q is 1, r is 1 and $X^4$ is a bond (cyclopropyl); or q is 2, r is 1 and $X^4$ is a bond (cyclobutyl).

According to a preferred embodiment, $R^{4b'}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, $C_6$-$C_{12}$-aryl-$C_1$-$C_4$-alkoxy, $C_3$-$C_{12}$-heterocyclyloxy or optionally substituted $C_3$-$C_{12}$-heterocyclyl.

According to a particular embodiment, $R^{4b'}$ is hydrogen, halogen, $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-aryl-$C_1$-$C_4$-alkyl, optionally substituted $C_6$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy or $C_6$-aryl-$C_1$-$C_4$-alkoxy.

According to a preferred embodiment, $R^{4g}$ is hydrogen, halogen, $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano or optionally substituted $C_3$-$C_{12}$-heterocyclyl.

According to a particular embodiment, $R^{4g}$ is hydrogen, halogen, $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-aryl-$C_1$-$C_4$-alkyl, optionally substituted $C_6$-aryl, cyano or $C_6$-aryl-$C_1$-$C_4$-alkoxy.

It is in particular preferred if $R^{4g}$ is an electron withdrawing group.

In connection with $R^{4a}$ substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $M_3$-$M_{12}$-heterocyclyl (e.g. morpholinyl or piperidinyl).

Preferably, $R^{4a}$ is hydrogen, $C_1$-$C_6$-alkyl (e.g. methyl, ethyl, n-propyl, isopropyl, 2-methyl-but-4-yl, or 2-methyl-prop-3-yl), $C_3$-$C_{12}$-cycloalkyl-$C_1$-$C_4$-alkyl (e.g. cyclopropylmethyl, cyclobutylmethyl, cyclopentylmethyl, 1-cyclopropyl-eth-2-yl, 1-cyclopentyl-eth-2-yl, or cyclohexylmethyl), halogenated $C_1$-$C_4$-alkyl (e.g. 2-fluoroethyl or 2,2,2-trifluoroethyl), amino-$C_1$-$C_4$-alkyl, —$CH_2CN$, $C_6$-$C_{12}$-aryl-$C_1$-$C_4$-alkyl (e.g. benzyl), optionally substituted $C_3$-$C_{12}$-cycloalkyl (e.g. cyclopropyl or cyclobutyl), $C_1$-$C_4$-alkylcarbonyl (e.g. methylcarbonyl or isopropylcarbonyl), (halogenated $C_1$-$C_4$-alkyl)carbonyl (e.g. fluoromethylcarbonyl, difluoromethylcarbonyl or trifluoromethylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl), —C(=NH)$NH_2$, —C(=NH)NHCN, $C_1$-$C_6$-alkylsulfonyl, amino, —NO or optionally substituted $M_3$-$M_{12}$-heterocyclyl (e.g. 3-oxetanyl).

More preferably, $R^{4a}$ is hydrogen, $C_1$-$C_6$-alkyl (e.g. methyl, ethyl, n-propyl, isopropyl, 2-methyl-but-4-yl, or 2-methyl-prop-3-yl), optionally substituted $C_3$-$C_{12}$-cycloalkyl (e.g. cyclopropyl or cyclobutyl), $C_3$-$C_{12}$-cycloalkyl-$C_1$-$C_4$-alkyl (e.g. cyclopropylmethyl, cyclobutylmethyl, cyclopentylmethyl, 1-cyclopropyl-eth-2-yl, 1-cyclopentyl-eth-2-yl, or cyclohexylmethyl), or $M_3$-$M_{12}$-heterocyclyl (e.g. 3-oxetanyl).

In particular, $R^{4a}$ is hydrogen, $C_1$-$C_6$-alkyl (e.g. methyl, ethyl, n-propyl, isopropyl, 2-methyl-but-4-yl, or 2-methyl-prop-3-yl), $C_3$-$C_{12}$-cycloalkyl-$C_1$-$C_4$-alkyl (e.g. cyclopropylmethyl, cyclobutylmethyl, cyclopentylmethyl, 1-cyclopropyl-eth-2-yl, 1-cyclopentyl-eth-2-yl, or cyclohexylmethyl), or optionally substituted $C_3$-$C_{12}$-cycloalkyl (e.g. cyclopropyl or cyclobutyl).

Alternatively, $R^{4a}$ is optionally substituted $C_1$-$C_4$-alkylene (e.g. methylene, 1,2-ethylene, or 1,3-propylene) that is bound to a carbon atom in $Y^1$. In connection with $R^{4a}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, hydroxy and $C_1$-$C_4$-alkoxy. In particular, $R^{4a}$ is $C_1$-$C_4$-alkylene (e.g. methylene or 1,2-ethylene) that is bound to a carbon atom in $Y^1$ with $Y^1$ being optionally substituted $C_1$-$C_4$-alkylene (e.g. 1,2-ethylene or 1,3-propylene) so that $R^{4a}$ and at least part of $Y^1$ together with the nitrogen atom to which $R^{4a}$ and $Y^1$ are bound form an N-containing heterocyclic ring having, in particular, 4, 5 or 6 ring member atoms (including the nitrogen atom). A derivative of the invention having such a ring may be represented by the following partial structure:

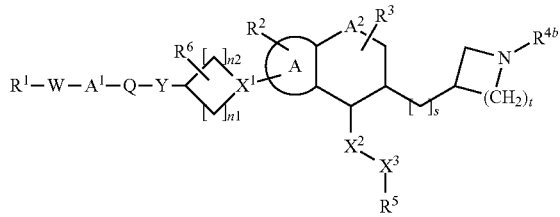

wherein A, $R^1$, W, $A^1$, Q, Y, $R^6$, n1, n2, $X^1$, $R^2$, $A^2$, $R^3$, $R^{4b}$, $X^3$, $R^5$ are as defined herein, s is 0, 1 or 2, and t is 0, 1, 2, or 3. Particular combinations of s and t include s=1, t=1; s=0, t=1; s=1, t=2; and s=0, t=2.

$R^{4b}$ is hydrogen, $C_1$-$C_6$-alkyl (e.g. methyl, ethyl), halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, —$CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino, —NO or $M_3$-$M_{12}$-heterocyclyl.

Preferably, $R^{4b}$ is hydrogen or $C_1$-$C_6$-alkyl (e.g. methyl or ethyl). In particular, $R^{4b}$ is hydrogen.

Alternatively, $R^{4a}$, $R^{4b}$ together are optionally substituted $C_2$-$C_6$-alkylene (e.g. 1,4-butylene, 1,3-propylene, 2-fluorobut-1,4-ylene, 1-oxo-but-1,4-ylene, 2-methyl-1,3-propylene, 2,2-dimethyl-1,3-propylene, or 2-methyl-2-hydroxy-1,3-propylene), wherein one —$CH_2$— of $C_2$-$C_6$-alkylene may be replaced by an oxygen atom (e.g. —$CH_2$—$CH_2$—O—$CH_2$—$CH_2$—) or —$NR^{10}$.

In connection with $R^{4a}$ and $R^{4b}$, substituted $C_2$-$C_6$-alkylene in particular includes $C_2$-$C_6$-alkylene substituted with 1 or more substituents $R^{4c}$, $R^{4d}$ and/or $R^{4e}$.

The compounds of the invention may therefore be represented by the following formula:

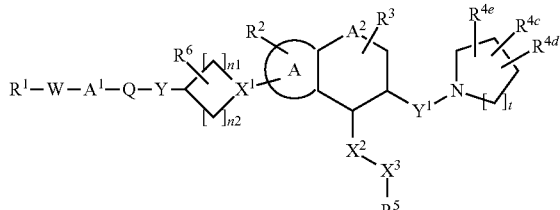

wherein A, $R^1$, W, $A^1$, Q, Y, $R^6$, n1, n2, $X^1$, $R^2$, $A^2$, $R^3$, $Y^1$, $X^2$, $X^3$ and $R^5$ are as defined herein, $R^{4c}$ and $R^{4d}$ are hydrogen, or $R^{4c}$, $R^{4d}$ together are $C_1$-$C_5$-alkylene optionally substituted with 1, 2 or 3 substituents $R^{4f}$, wherein one —$CH_2$— of $C_1$-$C_5$-alkylene may be replaced by an oxygen atom or —$NR^{18}$—, $R^{4e}$ is hydrogen, halogen, $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy or $C_6$-$C_{12}$-aryl-$C_1$-$C_4$-alkoxy; and in particular, $R^{4e}$ is hydrogen, t is 0, 1, 2 or 3; and according to a particular embodiment, t is 1, and $R^{18}$ is hydrogen, $C_1$-$C_6$-alkyl or $C_3$-$C_{12}$-cycloalkyl. Preferably, $R^{18}$ is hydrogen.

In connection with $R^{4a}$ and $R^{4e}$ substituted $C_6$-$C_{12}$-aryl in particular includes $C_6$-$C_{12}$-aryl, such as phenyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy. The same applies to substituted $C_6$-$C_{12}$-aryl in substituted $C_6$-$C_{12}$-aryl-$C_1$-$C_4$-alkyl.

According to a particular embodiment $R^{4c}$, $R^{4d}$ together are $C_1$-$C_5$-alkylene optionally substituted with 1, 2 or 3 substituents $R^{4f}$, wherein one —$CH_2$— of $C_1$-$C_5$-alkylene may be replaced by an oxygen atom or —$NR^{18}$—.

In connection with $R^{4c}$, $R^{4d}$, substituted $C_1$-$C_5$-alkylene in particular includes $C_1$-$C_5$-alkylene optionally substituted with 1, 2 or 3 substituents ($R^{4f}$) selected from the group consisting of hydrogen, halogen, $C_1$-$C_6$-alkyl, $C_3$-$C_{12}$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_6$-$C_{12}$-aryl-$C_1$-$C_4$-alkyl, $C_2$-$C_6$-alkenyl, $C_2$-$C_6$-alkynyl, optionally substituted $C_6$-$C_{12}$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, $C_6$-$C_{12}$-aryl-$C_1$-$C_4$-alkoxy, $M_3$-$M_{12}$-heterocyclyloxy or optionally substituted $M_3$-$M_{12}$-heterocyclyl, and more preferably hydrogen, halogen; $C_1$-$C_6$-alkyl, $C_3$-$C_6$-cycloalkyl-$C_1$-$C_4$-alkyl, halogenated $C_1$-$C_6$-alkyl, hydroxy-$C_1$-$C_4$-alkyl, $C_1$-$C_6$-alkoxy-$C_1$-$C_4$-alkyl, optionally substituted $C_1$-$C_6$-aryl-$C_1$-$C_4$-alkyl, optionally substituted $C_1$-$C_6$-aryl, cyano, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy or $C_1$-$C_6$-aryl-$C_1$-$C_4$-alkoxy.

According to a further particular embodiment, $R^{4c}$, $R^{4d}$ together with the carbon atom or the carbon atoms to which they are bound form a 3-, 4-, 5- or 6-membered ring, for example a ring comprised by the formula:

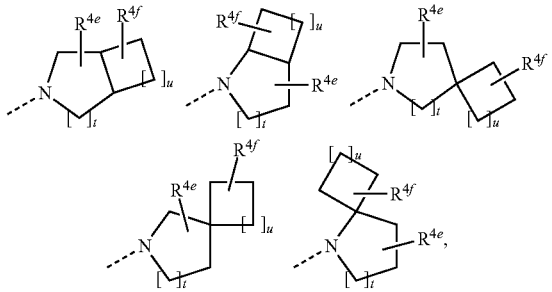

wherein t is defined as herein and u is 0, 1, 2, or 3, and $R^{4e}$ and $R^{4f}$ are as defined herein. Particular combinations of u and t include t=1 and u=0.

In said formulae, there may be one or more than one radical $R^{4e}$ and/or $R^{4f}$. More particularly, there may be up to 3 radicals $R^{4e}$ and/or up to 3 radicals $R^{4f}$. Preferably there is one radical $R^{4e}$ and/or one radical $R^{4f}$. Said formulae may thus also be depicted as follows:

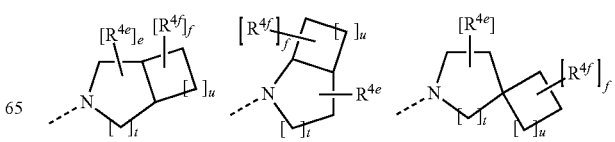

-continued

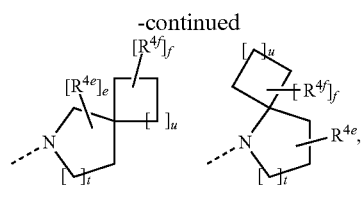

In said formulae, e is 1, 2 or 3 and f is 1, 2, or 3, with $R^{4e}$, $R^{4f}$, t and u being as defined herein. If there is more than one radical $R^{4e}$, these may be the same or different radicals. If there is more than one radical $R^{4f}$, these may be the same or different radicals.

The following examples of bicyclic moieties illustrate particular combinations of t, u and $R^{4e}$, $R^{4f}$ in the compounds of the present invention:

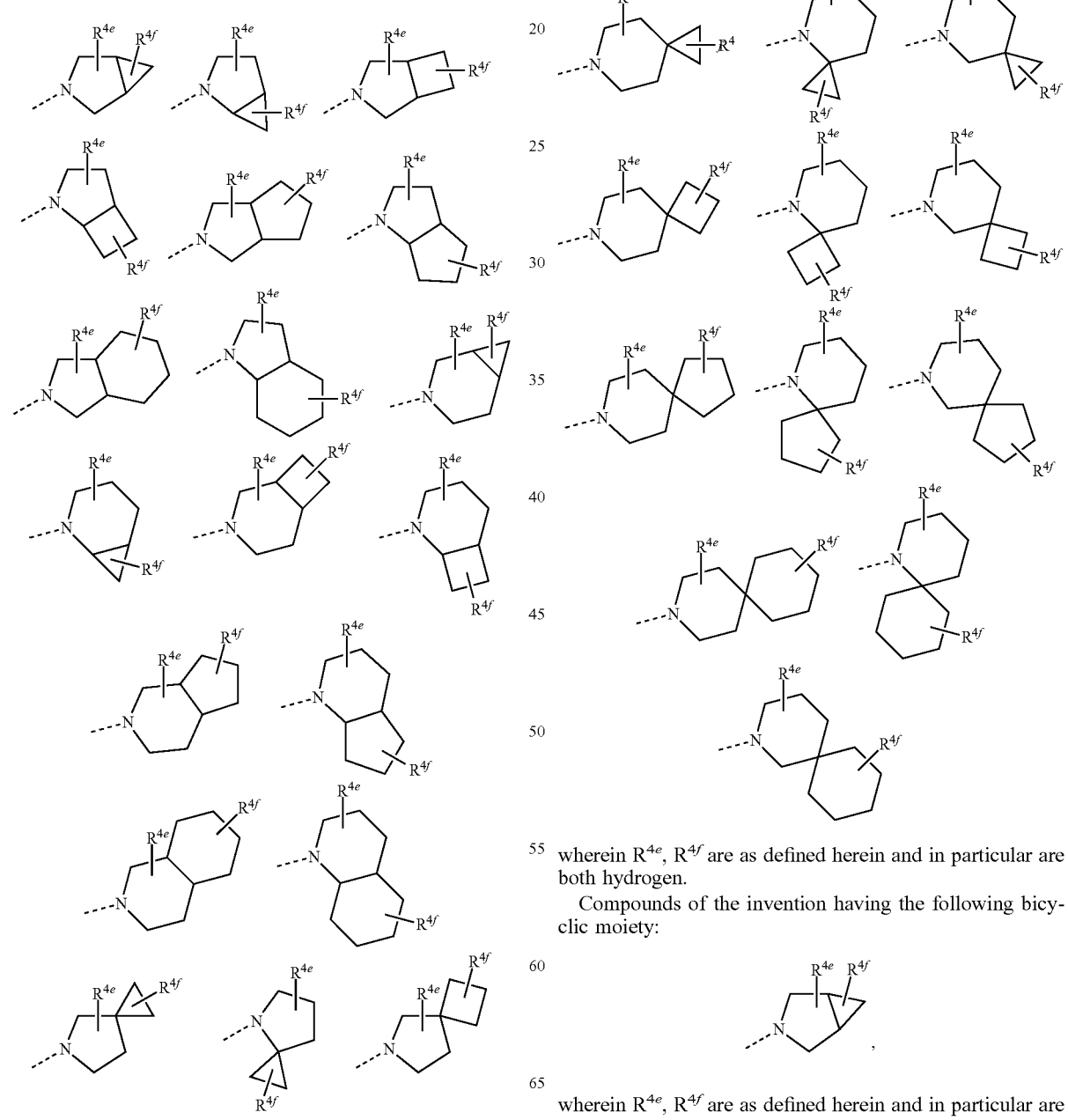

wherein $R^{4e}$, $R^{4f}$ are as defined herein and in particular are both hydrogen.

Compounds of the invention having the following bicyclic moiety:

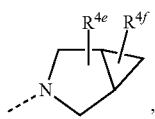

wherein $R^{4e}$, $R^{4f}$ are as defined herein and in particular are both hydrogen, are particularly preferred.

$X^2$ is —O—, —$NR^{11a}$—, >$CR^{12a}R^{12b}$ or a bond. In particular, $X^2$ is not a bond. Preferably, $X^2$ is >$CR^{12a}R^{12b}$.

$X^3$ is —O—, —$NR^{11b}$—, —S—, >$CR^{13a}R^{13b}$ or a bond. Preferably, $X^3$ is a bond.

Thus, it is preferred if $X^2$ is >$CR^{12a}R^{12b}$ and $X^3$ is a bond.

$R^{12a}$ is hydrogen, optionally substituted $C_1$-$C_6$-alkyl, $C_1$-$C_6$-alkylamino-$C_1$-$C_4$-alkyl, $M_3$-$M_{12}$-heterocyclyl-$C_1$-$C_6$-alkyl, optionally substituted $C_6$-$C_{12}$-aryl or hydroxy. Preferably, $R^{12a}$ is hydrogen or $C_1$-$C_6$-alkyl.

$R^{13a}$ is hydrogen, optionally substituted $C_1$-$C_6$-alkyl, $C_1$-$C_6$-alkylamino-$C_1$-$C_4$-alkyl, alkylamino $C_1$-$C_4$ alkyl, $M_3$-$M_{12}$-heterocyclyl-$C_1$-$C_6$-alkyl, optionally substituted $C_6$-$C_{12}$-aryl or hydroxy. Preferably, $R^{13a}$ is hydrogen or $C_1$-$C_6$-alkyl.

In connection with $R^{12a}$ and $R^{13a}$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino In connection with $R^{12a}$ and $R^{13a}$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

$R^{12b}$ is hydrogen or $C_1$-$C_6$-alkyl. According to a particular embodiment, $R^{12b}$ is hydrogen.

$R^{13b}$ is hydrogen or $C_1$-$C_6$-alkyl. According to a particular embodiment, $R^{13b}$ is hydrogen.

Alternatively, $R^{12a}$ and $R^{12b}$, or $R^{13a}$ and $R^{13b}$, together with the carbon atom to which they are attached form a carbonyl or, preferably, are optionally substituted $C_2$-$C_4$-alkylene (e.g. 1,3-propylene), wherein one —$CH_2$— of $C_2$-$C_4$-alkylene may be replaced by an oxygen atom or —$NR^{14}$—.

In connection with $R^{12a}$ and $R^{12b}$, or $R^{13a}$ and $R^{13b}$, substituted $C_2$-$C_4$-alkylene in particular includes $C_2$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

According to a particular embodiment, $R^{12a}$ is hydrogen or $C_1$-$C_6$-alkyl and $R^{12b}$ is hydrogen or $C_1$-$C_6$-alkyl, or $R^{13a}$ is hydrogen or $C_1$-$C_6$-alkyl and $R^{13b}$ is hydrogen or $C_1$-$C_6$-alkyl.

According to a further particular embodiment, $R^{12a}$ is hydrogen and $R^{12b}$ is hydrogen, or $R^{13a}$ is hydrogen and $R^{13b}$ is hydrogen.

According to a further particular embodiment, $R^{12a}$ and $R^{12b}$ together are optionally substituted 1,3-propylene, or $R^{13a}$ and $R^{13b}$ together are optionally substituted 1,3-propylene.

$R^5$ is optionally substituted $C_6$-$C_{12}$-aryl (e.g. phenyl, 2-fluorophenyl, 2-chlorophenyl, 3-fluorophenyl, 3-chlorophenyl; 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 2,4-dichlorophenyl or 3,4-dichlorophenyl), optionally substituted $C_3$-$C_{12}$-cycloalkyl (e.g. cyclohexyl) or optionally substituted $M_3$-$M_{12}$-heterocyclyl.

In connection with $R^5$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $M_3$-$M_{12}$-heterocyclyl.

In connection with $R^5$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), halogenated $C_1$-$C_6$-alkoxy, amino, $C_1$-$C_6$-alkylamino, di-$C_1$-$C_6$-alkylamino and $M_3$-$M_{12}$-heterocyclyl.

In connection with $R^5$, substituted $M_3$-$M_{12}$-heterocyclyl in particular includes $M_3$-$M_{12}$-heterocyclyl substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $M_3$-$M_{12}$-heterocyclyl.

In connection with $R^5$, $M_3$-$M_{12}$-heterocyclyl in particular is $M_3$-$M_{12}$-heteroaryl.

Preferably, $R^5$ is optionally substituted $C_6$-$C_{12}$-aryl, in particular as in the compounds of the formula:

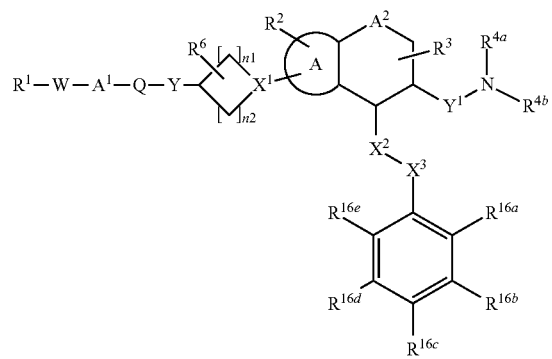

wherein A, $R^1$, W, $A^1$, Q, Y, $R^6$, n1, n2, $X^1$, $R^2$, $A^2$, $R^3$, $Y^1$, $R^{4a}$, $R^{4b}$, $X^2$, $X^3$ are as defined herein, and
$R^{16a}$, $R^{16b}$, $R^{16c}$, $R^{16d}$, $R^{16e}$ independently are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $M_3$-$M_{12}$-heterocyclyl. Preferably, $R^{16a}$, $R^{16b}$, $R^{16c}$, $R^{16d}$, $R^{16e}$ independently are hydrogen, halogen (e.g. F, Cl or Br), or halogenated $C_1$-$C_6$-alkyl (e.g. trifluoromethyl).

It is also preferred if $R^5$ is optionally substituted $M_6$-$M_{12}$-heteroaryl, in particular as in the compounds of the formula:

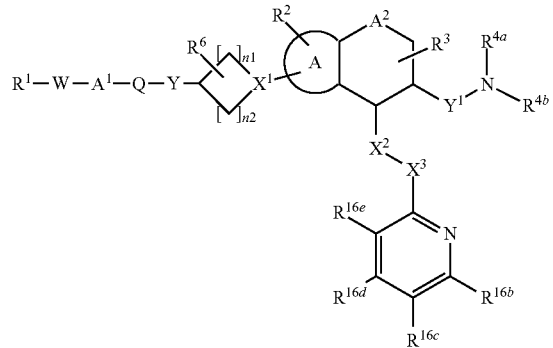

wherein A, $R^1$, W, $A^1$, Q, Y, $R^6$, n1, n2, $X^1$, $R^2$, $A^2$, $R^3$, $Y^1$, $R^{4a}$, $R^{4b}$, $X^2$, $X^3$ are as defined herein, and
$R^{16b}$, $R^{16c}$, $R^{16d}$, $R^{16e}$ independently are hydrogen, halogen (e.g. F, Cl or Br), optionally substituted $C_1$-$C_6$-alkyl (e.g.

methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $M_3$-$M_{12}$-heterocyclyl. Preferably, $R^{16b}$, $R^{16c}$, $R^{16d}$, $R^{16e}$ independently are hydrogen, halogen (e.g. F, Cl or Br), or halogenated $C_1$-$C_6$-alkyl (e.g. trifluoromethyl).

According to a particular embodiment, the invention relates to compounds of the formula:

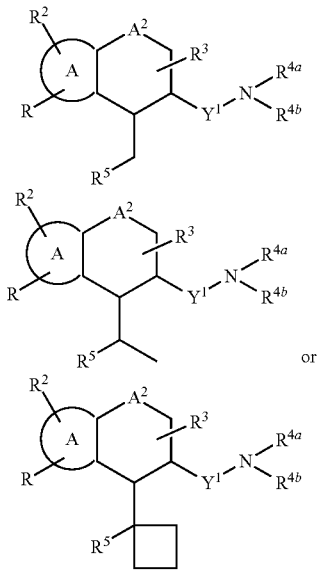

wherein A, R, $R^2$, $A^2$, $R^3$, $Y^1$, $R^{4a}$, $R^{4b}$, $R^5$ are as defined herein, $R^5$ preferably being optionally substituted aryl and in particular optionally substituted phenyl or optionally substituted heteroaryl and in particular optionally substituted pyridinyl as disclosed herein.

In connection with $R^5$ or $R^{16a}$, $R^{16b}$, $R^{16c}$, $R^{16d}$, $R^{16e}$, substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $M_3$-$M_{12}$-heterocyclyl (e.g. morpholinyl or piperidinyl).

According to a particular embodiment, $R^{16a}$, $R^{16b}$, $R^{16d}$, $R^{16e}$ are hydrogen and $R^{16c}$ is different from hydrogen (para-mono-substitution).

According to a further particular embodiment, $R^{16a}$, $R^{16c}$, $R^{16d}$, $R^{16e}$ are hydrogen and $R^{16b}$ is different from hydrogen (meta-mono-substitution).

In connection with $R^{16a}$, $R^{16b}$, $R^{16c}$, $R^{16d}$, $R^{16e}$, $M_3$-$M_{12}$-heterocyclyl in particular includes morpholinyl, imidazolyl and pyrazolyl.

$R^7$ is hydrogen or $C_1$-$C_6$-alkyl. Preferably, $R^7$ is hydrogen.

$R^8$ is hydrogen, $C_1$-$C_6$-alkyl (e.g. methyl or ethyl), $C_3$-$C_{12}$-cycloalkyl (e.g. cyclopropyl), amino-$C_1$-$C_6$-alkyl, optionally substituted $C_6$-$C_{12}$-aryl-$C_1$-$C_4$-alkyl or $M_3$-$M_{12}$-heterocyclyl (e.g. 3-azetidinyl). Preferably, $R^8$ is hydrogen or $C_1$-$C_6$-alkyl (e.g. methyl or ethyl). In particular, $R^8$ is hydrogen.

According to a particular embodiment, $R^8$ and $R^1$ together are $C_1$-$C_4$-alkylene (e.g. 1,2-ethylene or 1,3-propylene) so as that $R^8$ and $R^1$ together with the atom in Q to which $R^1$ is bound and the nitrogen atom to which $R^8$ is bound form an heterocyclic ring having, in particular, 4, 5 or 6 ring member atoms (including the nitrogen atom and Q). With W and $A^1$ both being a bond, such a ring may be represented by the following partial structure:

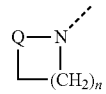

wherein Q, is as defined herein (e.g. $S(O)_2$) and n is 0, 1, 2, 3 or 4.

$R^9$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, —$CH_2CN$, $C_6$-$C_{12}$-aryl-$C_1$-$C_4$-alkyl, $C_3$-$C_{12}$-cycloalkyl, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $M_3$-$M_{12}$-heterocyclyl. Preferably, $R^9$ is hydrogen or $C_1$-$C_6$-alkyl. In particular, $R^9$ is hydrogen.

$R^{10}$ is hydrogen or $C_1$-$C_6$-alkyl. Preferably, $R^{10}$ is hydrogen.

$R^{11a}$ is hydrogen or $C_1$-$C_6$-alkyl. Preferably, $R^{11a}$ is hydrogen.

$R^{11b}$ is hydrogen or $C_1$-$C_6$-alkyl. Preferably, $R^{11b}$ is hydrogen.

$R^{14}$ is hydrogen or $C_1$-$C_6$-alkyl. Preferably, $R^{14}$ is hydrogen.

$R^{15}$ is hydrogen or $C_1$-$C_6$-alkyl. Preferably, $R^{15}$ is hydrogen.

$R^{17}$ is hydrogen, $C_1$-$C_6$-alkyl or $C_3$-$C_{12}$-cycloalkyl. Preferably, $R^{18}$ is hydrogen.

$R^{18}$ is hydrogen, $C_1$-$C_6$-alkyl or $C_3$-$C_{12}$-cycloalkyl. Preferably, $R^{18}$ is hydrogen.

Particular embodiments of compounds of the invention result if
A is a benzene ring
$R^1$ is $C_1$-$C_6$-alkyl (e.g. methyl, ethyl, n-propyl, isopropyl, n-butyl, sec-butyl, n-pentyl), $C_3$-$C_{12}$-cycloalkyl-$C_1$-$C_4$-alkyl (e.g. cyclopropylmethyl, cyclobutylmethyl, cyclopentylmethyl, cyclohexylmethyl, cyclopropylethyl), halogenated $C_1$-$C_6$-alkyl (e.g. 3-fluoroprop-1-yl, 3-chloroprop-1-yl or 3,3,3-trifluoroprop-1-yl), tri-($C_1$-$C_4$-alkyl)-silyl-$C_1$-$C_4$-alkyl (e.g. trimethylsilylethyl), $C_1$-$C_6$-alkoxy-$C_1$-$C_4$-alkyl (e.g. ethoxyethyl), $C_3$-$C_{12}$-cycloalkyl (e.g. cyclopropyl, cyclobutyl, cyclohexyl), $C_2$-$C_6$-alkenyl (e.g. prop-1,2-en-1-yl), optionally substituted $C_6$-$C_{12}$-aryl (e.g. phenyl, 3-methylphenyl), or optionally substituted $M_3$-$M_{12}$-heterocyclyl (e.g. 2-pyridyl, 3-pyridyl, 2-F-pyridin-3-yl, 5-F-pyridin-3yl, pyridazin-3-yl, 1-methyl-pyrrol-3yl, 2-thienyl, 3-thienyl, 4-methyl-2-thienyl, 5-methyl-2-thienyl, 5-chloro-2-thienyl, 2,5-dimethyl-3-thienyl, 3-furanyl, 5-methyl-2-furanyl, 2,5-dimethyl-3-furanyl, 1,2-diazol-4-yl, 1-methyl-1,2-diazol-4-yl, 1,3-dimethyl-1,2-diazol-4-yl, 1-ethyl-1,2-diazol-4-yl, 1-difluoromethyl-1,2-diazol-4-yl, 1-methyl-3-trifluoromethyl-1,2-diazol-4-yl, 1-methyl-1,3-diazol-4-yl, 2-methyl-1,3-diazol-4-yl, 1,2-dimethyl-1,3-diazol-4-yl, 2-methyl-1,3-thiazol-5-yl, 2,4-dimethyl-1,3-thiazol-5-yl, 5-methylisoxazol-3-yl, 1-methyl-1,2,3-triazol-4-yl, 1-ethyl-1,2,3-triazol-4-yl, 1-methyl-1,2,4-triazol-3-yl, 3-pyrrolidinyl, 3-oxenatyl, 3-methyl-piperidinyl, 4-morpholinyl, 2,2-difluoro-1,3-benzodioxol-5-yl);
W is a bond or $NR^7$;
$A^1$ is a bond;
Q is —$S(O)_2$— or —$C(O)$—;
Y is $NR^8$ or a bond;
n1 is 1 or 2;

n2 is 1 or 2;

$R^6$ is hydrogen, $C_1$-$C_6$-alkyl (e.g. methyl), or two radicals $R^6$ together with the carbon atom to which they are attached form a carbonyl group;

$X^1$ is >N— or >CH—;

$R^2$ is hydrogen, halogen (e.g. fluorine), or —CN;

$A^2$ is —O—;

$R^3$ is hydrogen or $C_1$-$C_6$-alkyl (e.g. methyl);

$Y^1$ is a bond or substituted $C_1$-$C_4$-alkylene (e.g. methylene, 1,2-ethylene);

$R^{4a}$ is hydrogen, $C_1$-$C_6$-alkyl (e.g. methyl, ethyl, n-propyl, isopropyl, 2-methyl-but-4-yl, 2-methyl-prop-3-yl), $C_3$-$C_{12}$-cycloalkyl-$C_1$-$C_4$-alkyl (e.g. cyclopropylmethyl, cyclobutylmethyl, cyclopentylmethyl, 1-cyclopropyleth-2-yl, 1-cyclopentyleth-2-yl, cyclohexylmethyl), halogenated $C_1$-$C_4$-alkyl (e.g. 2-fluoroethyl, 2,2,2-trifluoroethyl), $C_3$-$C_{12}$-cycloalkyl (e.g. cyclopropyl, cyclobutyl), —CHO, $C_1$-$C_4$-alkylcarbonyl (e.g. methylcarbonyl, ethylcarbonyl, isopropylcarbonyl), (halogenated $C_1$-$C_4$-alkyl)carbonyl (e.g. fluoromethylcarbonyl, difluoromethylcarbonyl, trifluoromethylcarbonyl, 1,1,1-trifluoroeth-2-ylcarbonyl, 1,1,1-trifluoroprop-3-ylcarbonyl), $C_6$-$C_{12}$-arylcarbonyl (e.g. phenylcarbonyl), $C_1$-$C_4$-alkoxycarbonyl (e.g. ethoxycarbonyl, tert-butyloxycarbonyl), $C_6$-$C_{12}$-aryloxycarbonyl (e.g. phenoxycarbonyl) or optionally substituted $M_3$-$M_{12}$-heterocyclyl (e.g. 3-oxetanyl, 3-cyano-3-oxetanyl); or $R^{4a}$ is optionally substituted $C_1$-$C_4$-alkylene that is bound to a carbon atom in $Y^1$ (e.g. methylene, 1,2-ethylene, 1,3-propylene);

$R^{4b}$ is hydrogen or $C_1$-$C_6$-alkyl (e.g. methyl, ethyl); or $R^{4a}$, $R^{4b}$ together are optionally substituted $C_2$-$C_6$-alkylene (e.g. 1,3-propylene, 1,4-butylene, 2-methyl-1,3-propylene, 2,2-dimethyl-1,3-propylene, 2-methyl-2-hydroxy-1,3-propylene, 2-fluoro-but-1,4-ylene, 1-oxo-but-1,4-ylene, —CH$_2$-cycloprop-1,2-ylene-CH$_2$—) wherein one —CH$_2$— of $C_2$-$C_6$-alkylene may be replaced by an oxygen atom (e.g. —CH$_2$—CH$_2$—O—CH$_2$—CH$_2$—);

$X^2$ is >CR$^{12a}$R$^{12b}$ $X^3$ is a bond;

$R^5$ is optionally substituted phenyl (e.g. phenyl, 2-fluorophenyl, 2-chlorophenyl, 3-fluorophenyl, 3-chlorophenyl, 3-trifluoromethylphenyl, 3-cyanophenyl, 3-methylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 3,4-dichlorophenyl, 2,4-dichlorophenyl) or optionally substituted $C_3$-$C_{12}$-cycloalkyl (e.g. cyclohexyl);

$R^7$ is hydrogen or $C_1$-$C_6$-alkyl (e.g. methyl);

$R^8$ is hydrogen, $C_1$-$C_6$-alkyl (e.g. methyl or ethyl), or $C_3$-$C_{12}$-cycloalkyl (e.g. cyclopropyl); or $R^8$, $R^1$ together are $C_1$-$C_4$-alkylene (e.g. 1,3-propylene);

$R^{12a}$ is hydrogen, $C_1$-$C_6$-alkyl (e.g. methyl or ethyl);

$R^{12b}$ is hydrogen;

$R^{12a}$, $R^{12b}$ together are optionally substituted $C_2$-$C_4$-alkylene (e.g. 1,3-propylene).

Further particular embodiments of compounds of the invention result if

A is a benzene ring $R^1$ is $C_1$-$C_6$-alkyl (e.g. ethyl, n-propyl), $C_3$-$C_{12}$-cycloalkyl-$C_1$-$C_4$-alkyl (e.g. cyclopropylmethyl), or optionally substituted $M_3$-$M_{12}$-heterocyclyl (e.g. 3 e.g. 1-methyl-1,2-diazol-4-yl, 1-methyl-1,3-diazol-4-yl, 1-methyl-1,2,3-triazol-4-yl, 1-ethyl-1,2,3-triazol-4-yl, 2-F-pyridin-3-yl, 5-F-pyridin-3yl, pyridazin-3-yl);

W is a bond;

$A^1$ is a bond;

Q is —S(O)$_2$—;

Y is NR$^8$;

n1 is 1;

n2 is 1;

$R^6$ is hydrogen;

$X^1$ is >N— or —CH—;

$R^2$ is hydrogen or halogen (e.g. fluorine);

$A^2$ is —O—;

$R^3$ is hydrogen;

$Y^1$ is a bond;

$R^{4a}$ is hydrogen, $C_1$-$C_6$-alkyl (e.g. methyl, ethyl, n-propyl), $C_3$-$C_{12}$-cycloalkyl-$C_1$-$C_4$-alkyl (e.g. cyclopropylmethyl) or $C_3$-$C_{12}$-cycloalkyl (e.g. cyclobutyl);

$R^{4b}$ is hydrogen or $C_1$-$C_6$-alkyl (e.g. ethyl); or $R^{4a}$, $R^{4b}$ together are $C_2$-$C_6$-alkylene (e.g. 1,3-propylene);

$X^2$ is >CR$^{12a}$R$^{12b}$ $X^3$ is a bond;

$R^5$ is optionally substituted phenyl (e.g. phenyl);

$R^8$ is hydrogen, or $R^{12a}$ is hydrogen;

$R^{12b}$ is hydrogen.

Further particular compounds of the present invention are the individual aminochromane, aminothiochromane and amino-1,2,3,4-tetrahydroquinoline derivatives of the formula (Id) as listed in the following tables 1 to 24 and physiologically tolerated salts thereof:

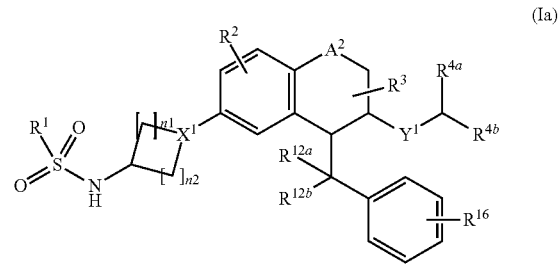

(Ia)

Table 1

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is hydrogen, $R^3$ is as defined herein and in particular represents hydrogen, $R^{16}$ is hydrogen and the combination of $R^1$, —$X^1$—, n1, n2, >CR$^{12a}$R$^{12b}$, $R^{4a}$, $R^{4b}$ for a compound in each case corresponds to one line of Table A (A-1 to A-88).

Table 2

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is hydrogen, $R^3$ is as defined herein and in particular represents hydrogen, $R^{16}$ is 3-F and the combination of $R^1$, —$X^1$—, n1, n2, >CR$^{12a}$R$^{12b}$, $R^{4a}$, $R^{4b}$ for a compound in each case corresponds to one line of Table A (A-1 to A-88).

Table 3

Compounds of the formula (Ia) wherein $R^6$ is as defined herein and in particular represents H, -$A^2$- is as defined herein and in particular represents —O—, —$Y^1$— is as defined herein and in particular represents a bond, $R^2$ is hydrogen, $R^3$ is as defined herein and in particular represents hydrogen, $R^{16}$ is 3-Cl and the combination of $R^1$, —$X^1$—, n1, n2, $R^{4a}$, $R^{4b}$ for a compound in each case corresponds to one line of Table A (A-1 to A-88).

Table 4

Compounds of the formula (Ia) wherein $R^6$ is as defined herein and in particular represents H, -$A^2$- is as defined herein and in particular represents —O—, —$Y^1$— is as defined herein and in particular represents a bond, $R^2$ is hydrogen, $R^3$ is as defined herein and in particular represents hydrogen, $R^{16}$ is 3-$CF_3$ and the combination of $R^1$, —$X^1$—, $R^{4a}$, $R^{4b}$ for a compound in each case corresponds to one line of Table A (A-1 to A-88).

Table 5

Compounds of the formula (Ia) wherein $R^6$ is as defined herein and in particular represents H, -$A^2$- is as defined herein and in particular represents —O—, —$Y^1$— is as defined herein and in particular represents a bond, $R^2$ is hydrogen, $R^3$ is as defined herein and in particular represents hydrogen, $R^{16}$ is 4-F and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 6

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is hydrogen, $R^3$ is as defined herein and in particular represents hydrogen, $R^{16}$ is 4-Cl and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 7

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 5-F, $R^3$ is as defined herein and in particular represents hydrogen, $R^{16}$ is hydrogen and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 8

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 5-F, $R^3$ is as defined herein and in particular represents hydrogen, $R^{16}$ is 3-F and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 9

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 5-F, $R^3$ is as defined herein and in particular represents hydrogen, $R^{16}$ is 3-$CF_3$ and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 10

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 5-F, $R^3$ is as defined herein and in particular represents hydrogen, $R^{16}$ is 3-$CF_3$ and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 11

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 5-F, $R^3$ is as defined herein and in particular represents hydrogen, $R^{16}$ is 4-F and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 12

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 5-F, $R^3$ is as defined herein and in particular represents hydrogen, $R^{16}$ is 4-Cl and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 13

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 7-F, $R^3$ is as defined herein and in particular represents hydrogen, $R^{16}$ is hydrogen and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 14

Compounds of the formula (Ia) wherein $R^6$ is as defined herein and in particular represents H, -$A^2$- is as defined herein and in particular represents —O—, —$Y^{1-}$ is as defined herein and in particular represents a bond $R^2$ is 7-F, $R^3$ is as defined herein and in particular represents hydrogen, $R^{16}$ is 3-F and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 15

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 7-F, $R^3$ is as defined herein and in particular represents hydrogen, $R^{16}$ is 3-Cl and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 16

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 7-F, $R^3$ is as defined herein and in particular represents hydrogen, $R^{16}$ is 3-$CF_3$ and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 17

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 7-F, $R^3$ is as defined herein and in particular represents hydrogen, $R^{16}$ is 4-F and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 18

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 7-F, $R^3$ is as defined herein and in particular represents hydrogen, $R^{16}$ is 4-Cl and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 19

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 8-F, $R^3$ is as defined herein and in particular represents hydrogen, $R^{16}$ is hydrogen and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 20

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 8-F, $R^3$ is as defined herein and in particular represents hydrogen, $R^{16}$ is 3-F and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 21

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 8-F, $R^3$ is as defined herein and in particular represents hydrogen, $R^{16}$ is 3-Cl and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 22

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 8-F, $R^3$ is as defined herein and in particular represents hydrogen, $R^{16}$ is 3-$CF_3$ and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 23

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 8-F, $R^3$ is as defined herein and in particular represents hydrogen, $R^{16}$ is 4-F and the combination of $R^1$, —$X^1$—, n1, n2, >$CR^{12a}R^{12b}$, $R^{4a}$, $R^{4b}$ for a compound in each case corresponds to one line of Table A (A-1 to A-88).

Table 24

Compounds of the formula (Ia) wherein $R^6$ is as defined herein and in particular represents H, -$A^2$- is as defined herein and in particular represents —O—, —$Y^{1-}$ is as defined herein and in particular represents a bond, $R^2$ is 8-F, $R^3$ is as defined herein and in particular represents hydrogen, $R^{16}$ is 4-Cl and the combination of $R^1$, —$X^1$—, n1, n2, >$CR^{12a}R^{12b}$, $R^{4a}$, $R^{4b}$ for a compound in each case corresponds to one line of Table A (A-1 to A-88).

| | R1 | —$X^1$— | n1 | n2 | >$CR^{12a}R^{12b}$ | $R^{4a}$, $R^{4b}$ |
|---|---|---|---|---|---|---|
| A-1. | cyclopropylmethyl | >N— | 1 | 1 | —$CH_2$— | H, H |
| A-2. | cyclobutyl | >N— | 1 | 1 | —$CH_2$— | H, H |
| A-3. | isopropyl | >N— | 1 | 1 | —$CH_2$— | H, H |
| A-4. | ethyl | >N— | 1 | 1 | —$CH_2$— | H, H |
| A-5. | n-butyl | >N— | 1 | 1 | —$CH_2$— | H, H |
| A-6. | pyridin-3-yl | >N— | 1 | 1 | —$CH_2$— | H, H |
| A-7. | 1-methyl-imidazol-5-yl | >N— | 1 | 1 | —$CH_2$— | H, H |
| A-8. | 1-methyl-pyrazol-4-yl | >N— | 1 | 1 | —$CH_2$— | H, H |
| A-9. | 1-methyl-pyrrol-3-yl | >N— | 1 | 1 | —$CH_2$— | H, H |
| A-10. | 1-methyl-1,2,3-triazol-4-yl | >N— | 1 | 1 | —$CH_2$— | H, H |

-continued

| | R1 | —X¹— | n1 | n2 | >CR$^{12a}$R$^{12b}$ | R$^{4a}$, R$^{4b}$ |
|---|---|---|---|---|---|---|
| A-11. | (1-ethyl-1H-1,2,3-triazol-4-yl) | >N— | 1 | 1 | —CH$_2$— | H, H |
| A-12. | (cyclopropylmethyl) | >CH— | 1 | 1 | —CH$_2$— | H, H |
| A-13. | (cyclobutyl) | >CH— | 1 | 1 | —CH$_2$— | H, H |
| A-14. | (ethyl) | >CH— | 1 | 1 | —CH$_2$— | H, H |
| A-15. | (propyl) | >CH— | 1 | 1 | —CH$_2$— | H, H |
| A-16. | (butyl) | >CH— | 1 | 1 | —CH$_2$— | H, H |
| A-17. | (pyridin-3-yl) | >CH— | 1 | 1 | —CH$_2$— | H, H |
| A-18. | (1-methyl-1H-imidazol-5-yl) | >CH— | 1 | 1 | —CH$_2$— | H, H |
| A-19. | (1-methyl-1H-pyrazol-4-yl) | >CH— | 1 | 1 | —CH$_2$— | H, H |
| A-20. | (1-methyl-1H-pyrrol-3-yl) | >CH— | 1 | 1 | —CH$_2$— | —H, H |
| A-21. | (1-methyl-1H-1,2,3-triazol-4-yl) | >CH— | 1 | 1 | —CH$_2$— | H, H |
| A-22. | (1-ethyl-1H-1,2,3-triazol-4-yl) | >CH— | 1 | 1 | —CH$_2$— | H, H |
| A-23. | (cyclopropylmethyl) | >N— | 1 | 1 | —CH$_2$— | —CH$_3$, H |
| A-24. | (cyclobutyl) | >N— | 1 | 1 | —CH$_2$— | —CH$_3$, H |
| A-25. | (ethyl) | >N— | 1 | 1 | —CH$_2$— | —CH$_3$, H |
| A-26. | (propyl) | >N— | 1 | 1 | —CH$_2$— | —CH$_3$, H |
| A-27. | (butyl) | >N— | 1 | 1 | —CH$_2$— | —CH$_3$, H |
| A-28. | (pyridin-3-yl) | >N— | 1 | 1 | —CH$_2$— | —CH$_3$, H |
| A-29. | (1-methyl-1H-imidazol-5-yl) | >N— | 1 | 1 | —CH$_2$— | —CH$_3$, H |
| A-30. | (1-methyl-1H-pyrazol-4-yl) | >N— | 1 | 1 | —CH$_2$— | —CH$_3$, H |

-continued

| | R1 | —X¹— | n1 | n2 | >CR$^{12a}$R$^{12b}$ | R$^{4a}$, R$^{4b}$ |
|---|---|---|---|---|---|---|
| A-31. | N-methylpyrrol-3-yl | >N— | 1 | 1 | —CH$_2$— | —CH$_3$, H |
| A-32. | 1-methyl-1,2,3-triazol-4-yl | >N— | 1 | 1 | —CH$_2$— | —CH$_3$, H |
| A-33. | 1-ethyl-1,2,3-triazol-4-yl | >N— | 1 | 1 | —CH$_2$— | —CH$_3$, H |
| A-34. | cyclopropylmethyl | >CH— | 1 | 1 | —CH$_2$— | —CH$_3$, H |
| A-35. | cyclobutyl | >CH— | 1 | 1 | —CH$_2$— | —CH$_3$, H |
| A-36. | isopropyl | >CH— | 1 | 1 | —CH$_2$— | —CH$_3$, H |
| A-37. | sec-butyl | >CH— | 1 | 1 | —CH$_2$— | —CH$_3$, H |
| A-38. | pentan-3-yl | >CH— | 1 | 1 | —CH$_2$— | —CH$_3$, H |
| A-39. | pyridin-3-yl | >CH— | 1 | 1 | —CH$_2$— | —CH$_3$, H |
| A-40. | 1-methylimidazol-5-yl | >CH— | 1 | 1 | —CH$_2$— | —CH$_3$, H |
| A-41. | 1-methylpyrazol-4-yl | >CH— | 1 | 1 | —CH$_2$— | —CH$_3$, H |
| A-42. | N-methylpyrrol-3-yl | >CH— | 1 | 1 | —CH$_2$— | —CH$_3$, H |
| A-43. | 1-methyl-1,2,3-triazol-4-yl | >CH— | 1 | 1 | —CH$_2$— | —CH$_3$, H |
| A-44. | 1-ethyl-1,2,3-triazol-4-yl | >CH— | 1 | 1 | —CH$_2$— | —CH$_3$, H |
| A-45. | cyclopropylmethyl | >N— | 1 | 1 | —CH$_2$— | —(CH$_2$)$_3$— |
| A-46. | cyclobutyl | >N— | 1 | 1 | —CH$_2$— | —(CH$_2$)$_3$— |
| A-47. | isopropyl | >N— | 1 | 1 | —CH$_2$— | —(CH$_2$)$_3$— |
| A-48. | sec-butyl | >N— | 1 | 1 | —CH$_2$— | —(CH$_2$)$_3$— |
| A-49. | pentan-3-yl | >N— | 1 | 1 | —CH$_2$— | —(CH$_2$)$_3$— |
| A-50. | pyridin-3-yl | >N— | 1 | 1 | —CH$_2$— | —(CH$_2$)$_3$— |

-continued

| | R1 | —X¹— | n1 | n2 | >CR$^{12a}$R$^{12b}$ | R$^{4a}$, R$^{4b}$ |
|---|---|---|---|---|---|---|
| A-51. | (1-methyl-imidazol-4-yl) | >N— | 1 | 1 | —CH$_2$— | —(CH$_2$)$_3$— |
| A-52. | (1-methyl-pyrazol-4-yl) | >N— | 1 | 1 | —CH$_2$— | —(CH$_2$)$_3$— |
| A-53. | (1-methyl-pyrrol-3-yl) | >N— | 1 | 1 | —CH$_2$— | —(CH$_2$)$_3$— |
| A-54. | (1-methyl-1,2,3-triazol-4-yl) | >N— | 1 | 1 | —CH$_2$— | —(CH$_2$)$_3$— |
| A-55. | (1-ethyl-1,2,3-triazol-4-yl) | >N— | 1 | 1 | —CH$_2$— | —(CH$_2$)$_3$— |
| A-56. | cyclopropylmethyl | >CH— | 1 | 1 | —CH$_2$— | —(CH$_2$)$_3$— |
| A-57. | cyclobutyl | >CH— | 1 | 1 | —CH$_2$— | —(CH$_2$)$_3$— |
| A-58. | isopropyl | >CH— | 1 | 1 | —CH$_2$— | —(CH$_2$)$_3$— |
| A-59. | sec-butyl | >CH— | 1 | 1 | —CH$_2$— | —(CH$_2$)$_3$— |
| A-60. | pentan-2-yl | >CH— | 1 | 1 | —CH$_2$— | —(CH$_2$)$_3$— |
| A-61. | (pyridin-3-yl) | >CH— | 1 | 1 | —CH$_2$— | —(CH$_2$)$_3$— |
| A-62. | (1-methyl-imidazol-4-yl) | >CH— | 1 | 1 | —CH$_2$— | —(CH$_2$)$_3$— |
| A-63. | (1-methyl-pyrazol-4-yl) | >CH— | 1 | 1 | —CH$_2$— | —(CH$_2$)$_3$— |
| A-64. | (1-methyl-pyrrol-3-yl) | >CH— | 1 | 1 | —CH$_2$— | —(CH$_2$)$_3$— |
| A-65. | (1-methyl-1,2,3-triazol-4-yl) | >CH— | 1 | 1 | —CH$_2$— | —(CH$_2$)$_3$— |
| A-66. | (1-ethyl-1,2,3-triazol-4-yl) | >CH— | 1 | 1 | —CH$_2$— | —(CH$_2$)$_3$— |
| A-67. | cyclopropylmethyl | >N— | 1 | 1 | —CH$_2$— | —(CH$_2$)$_4$— |
| A-68. | cyclobutyl | >N— | 1 | 1 | —CH$_2$— | —(CH$_2$)$_4$— |

| | R1 | —X¹— | n1 | n2 | >CR¹²ᵃR¹²ᵇ | R⁴ᵃ, R⁴ᵇ |
|---|---|---|---|---|---|---|
| A-69. |  | >N— | 1 | 1 | —CH₂— | —(CH₂)₄— |
| A-70. |  | >N— | 1 | 1 | —CH₂— | —(CH₂)₄— |
| A-71. | 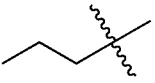 [SMILES: *CCC] | >N— | 1 | 1 | —CH₂— | —(CH₂)₄— |
| A-72. | 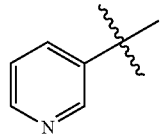 [SMILES: *c1cccnc1] | >N— | 1 | 1 | —CH₂— | —(CH₂)₄— |
| A-73. | 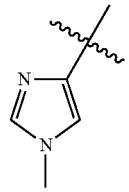 [SMILES: *c1cn(C)cn1] | >N— | 1 | 1 | —CH₂— | —(CH₂)₄— |
| A-74. | 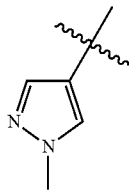 [SMILES: *c1cnn(C)c1] | >N— | 1 | 1 | —CH₂— | —(CH₂)₄— |
| A-75. | 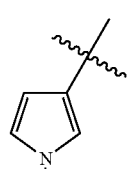 | >N— | 1 | 1 | —CH₂— | —(CH₂)₄— |
| A-76. | 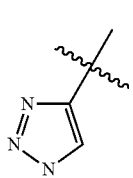 | >N— | 1 | 1 | —CH₂— | —(CH₂)₄— |
| A-77. | 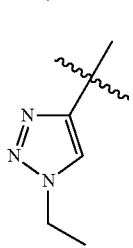 | >N— | 1 | 1 | —CH₂— | —(CH₂)₄— |
| A-78. | 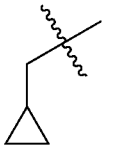 [SMILES: *CC1CC1] | >CH— | 1 | 1 | —CH₂— | —(CH₂)₄— |
| A-79. | 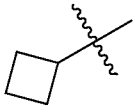 [SMILES: *C1CCC1] | >CH— | 1 | 1 | —CH₂— | —(CH₂)₄— |
| A-80. | 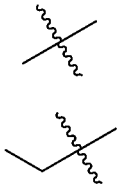 | >CH— | 1 | 1 | —CH₂— | —(CH₂)₄— |
| A-81. | 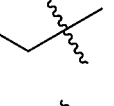 | >CH— | 1 | 1 | —CH₂— | —(CH₂)₄— |
| A-82. |  | >CH— | 1 | 1 | —CH₂— | —(CH₂)₄— |
| A-83. | 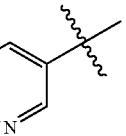 | >CH— | 1 | 1 | —CH₂— | —(CH₂)₄— |
| A-84. | 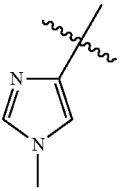 [SMILES: *c1cn(C)cn1] | >CH— | 1 | 1 | —CH₂— | —(CH₂)₄— |
| A-85. | 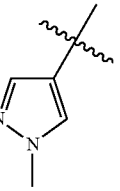 | >CH— | 1 | 1 | —CH₂— | —(CH₂)₄— |
| A-86. | 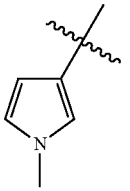 [SMILES: *c1ccn(C)c1] | >CH— | 1 | 1 | —CH₂— | —(CH₂)₄— |
| A-87. | 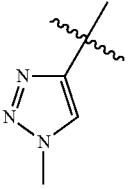 [SMILES: *c1cn(C)nn1] | >CH— | 1 | 1 | —CH₂— | —(CH₂)₄— |

-continued

| | R1 | —X¹— | n1 | n2 | >CR¹²ᵃR¹²ᵇ | R⁴ᵃ, R⁴ᵇ |
|---|---|---|---|---|---|---|
| A-88. | 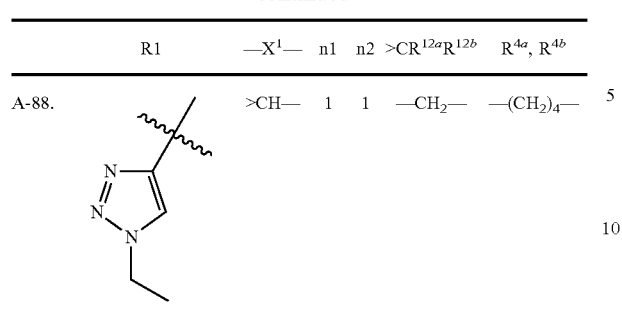 | >CH— | 1 | 1 | —CH₂— | —(CH₂)₄— |

Still further particular compounds of the present invention are the compounds disclosed in preparation examples and physiologically tolerated salts thereof. These include for each preparation example the exemplified compound as well as the corresponding free base and any other physiologically tolerated salts of the free base (if the exemplified compound is a salt), or any physiologically tolerated salt of the free base (if the exemplified compound is a free base). These further include enantiomers, diastereomers, tautomers and any other isomeric forms of said compounds, be they explicitly or implicitly disclosed.

The compounds of the formula (I) can be prepared by analogy to methods which are well known in the art. Suitable methods for the preparation of compounds of formula (I) are outlined in the schemes.

The process depicted in scheme 1 is useful for obtaining aminochromanes of general formula 5, wherein X⁴ is —O—.

Scheme 1:

As shown in scheme 1, the compound of general formula 1 can be transferred into the corresponding hydroxylamine 2 (e.g. in presence of NH₂OH HCl). The hydroxyl group can be converted to a leaving group (e.g. tosyl or mesyl) to yield compounds of the general formula 3. Compounds 3 readily undergo Neber rearrangement in the presence of a base (e.g. NaOEt, J. Med. Chem. 1988, 31, 2178) followed by protection with a suitable protecting group L² (e.g. L²=COOEt) to give the compound of general formula 5.

In scheme 1, the variables R² and R³ are as defined herein and L¹ is a suitable protecting group (e.g. L¹=Me).

Compounds of the general formula 1 are also readily accessible from common bulk chemicals as described in scheme 2. The process depicted in scheme 2 is useful for obtaining aminochromanes of general formula 1, wherein X⁴ is —O— and L¹ is a suitable protecting group (e.g. L¹=Me).

Scheme 2:

Phenols of the general formula 1-1 can be reacted with 3-halogenated carboxylic acids like 1-2 in presence of a base as described in the literature (e.g. potassium hydroxide, sodium hydrogencarbonate, J. Med. Chem. 1982, 25, 393) to give compounds of the general formula 1-3. In presence of an acid these compounds undergo acylation reactions to form compounds of the general formula 1 (e.g. polyphosphoric acid, J. Med. Chem. 1982, 25, 393).

The process depicted in scheme 3 is useful for obtaining aminochromanes, wherein $X^1$ is >N—, $X^4$ is —O—, Y is —$NR^8$—, and Q is —$S(O)_2$—.

Scheme 3:

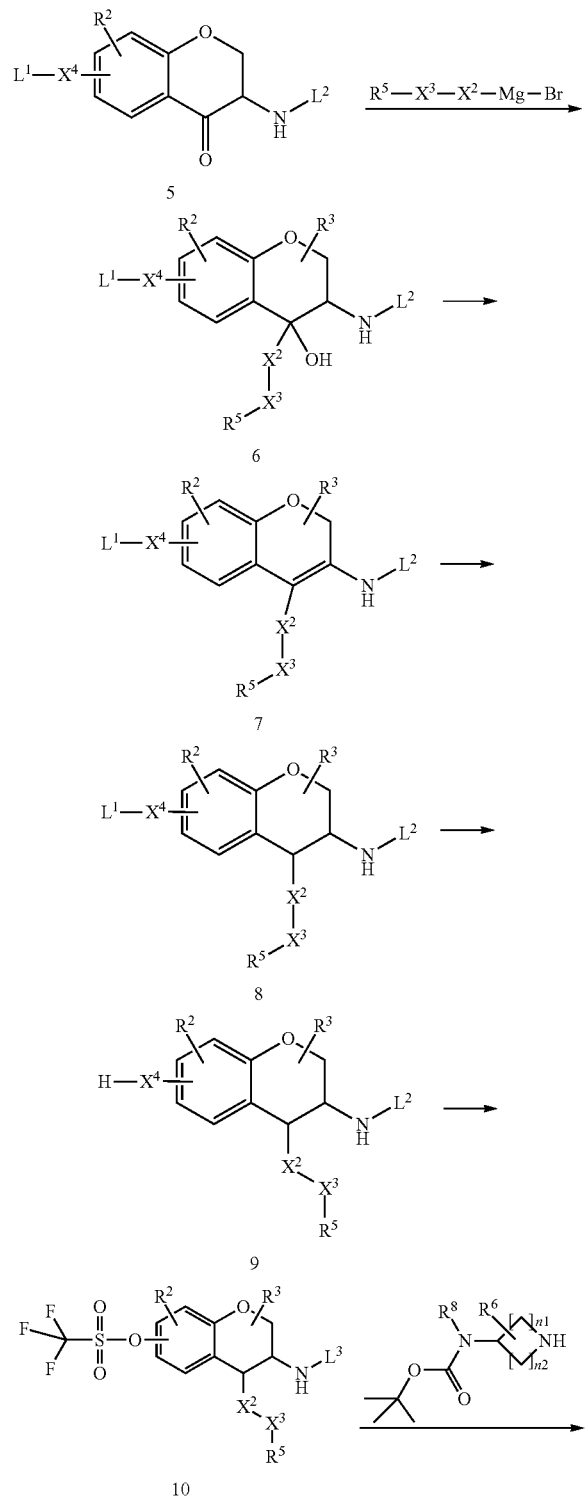

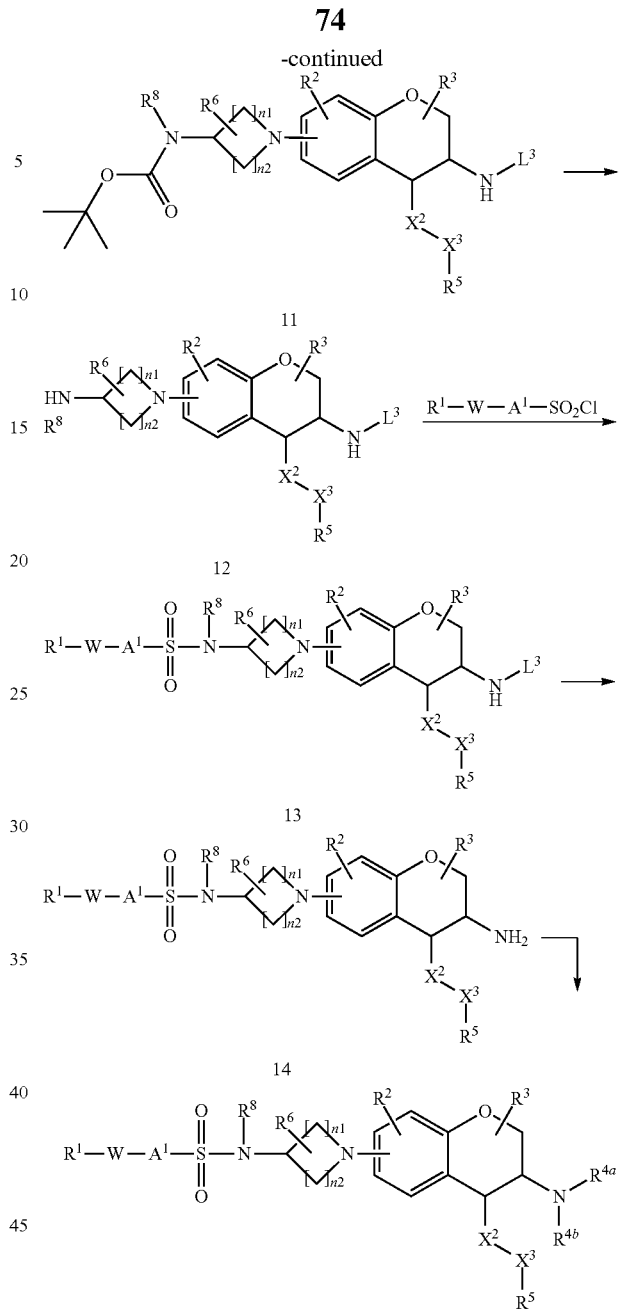

Aminochromanes of the general formula 5 can be reacted with a Grignard reagent to give the alcohols of the general formula 6. In presence of an acid (e.g. aqueous hydrochloric acid) these alcohols undergo elimination to the corresponding alkenes of general formula 7. Reduction of compounds of type 7 (e.g. by hydrogenation with $H_2$ and Pd/C in presence of an acid (e g ammonium formiate)) leads to aminochromanes of the general formula 8. The free phenols 9 can be accessed via removal of the protecting group $L^1$ (e.g. for $L^1$=Me by treating compounds 8 with boron tribromide). The phenols of general formula 9 can be transferred into the triflates 10 in presence of trifluoromethanesulfonic anhydride or 2-[N,N-Bis(trifluoromethylsulfonyl) amino]-5-chloropyridine. As described in the literature (e.g. Chem. Sci. 2011, 2, 27-50) triflate 10 can undergo a Buchwald-Hartwig amination with a cyclic amine in the presence of a palladium source (e.g. Pd(II) acetate), a ligand (e.g. dicyclohexyl(2',4',6'-triisopropyl-[1,1'-biphenyl]-2-yl)phosphine) and a base (e.g. cesium carbonate) to yield compounds of the general formula 11. Alternatively to the triflates 10 the corresponding nonaflates or bromides can be used to prepare compound 11. Deprotection of the Boc-group in presence of an acid (e.g. trifluoroacetic acid or formic acid) leads to the compounds of the general formula 12. Treatment with sulfonyl chlorides in presence of a base (e.g. N,N-dimethylaminopyridine or pyridine) yields compound 13. Deprotection of the protecting group $L^2$ (for $L^2$=ethylcarbamate e.g. ethanolic potassium hydroxide) will lead to the free amine of the general formula 14. Reductive amination using the corresponding ketones or aldehydes in presence of a reduction reagent (e.g. sodiumcyanoborohydride and glacial acetic acid) or amide formation followed by subsequent reduction yields the corresponding higher alkylated amines of the general formula 15. Reduction of the ethylcarbamte ($L^3$) of compound 13 (e.g. using lithium aluminum hydride) leads directly to compounds of the general formula 15 with $R^{4a}$=methyl and $R^{4b}$=hydrogen or vice versa.

In scheme 3, the variables $R^1$, W, $A^1$, $R^2$, $R^3$, $R^{4a}$, $R^{4b}$, $R^5$, $R^6$, $R^8$, $X^2$, $X^3$, n1 and n2 are as defined herein, and $L^1$ and $L^2$ are suitable protecting groups (e.g. $L^1$=Me, and $L^2$=COOEt).

The process depicted in scheme 4 is useful for obtaining aminochromanes, wherein $X^1$ is —CH—, Y is —$NR^8$—, and Q is —$S(O)_2$—.

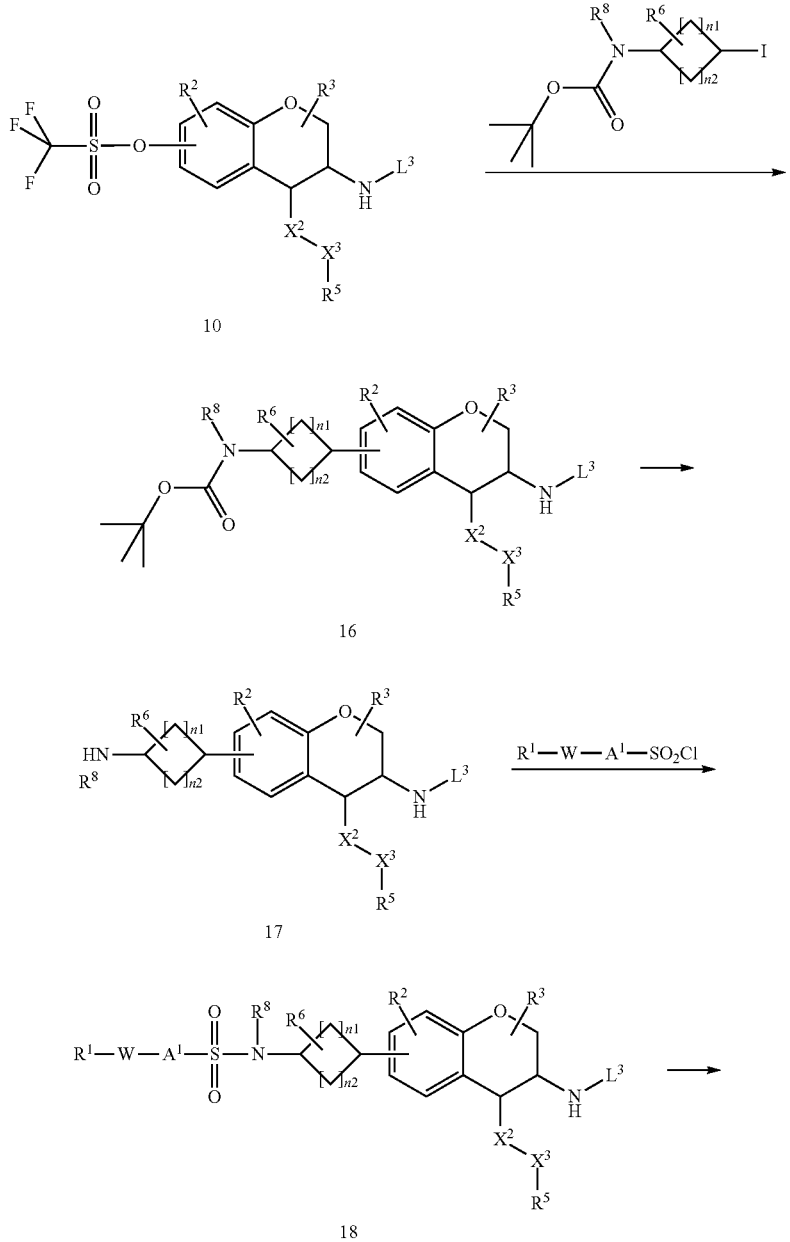

Scheme 4:

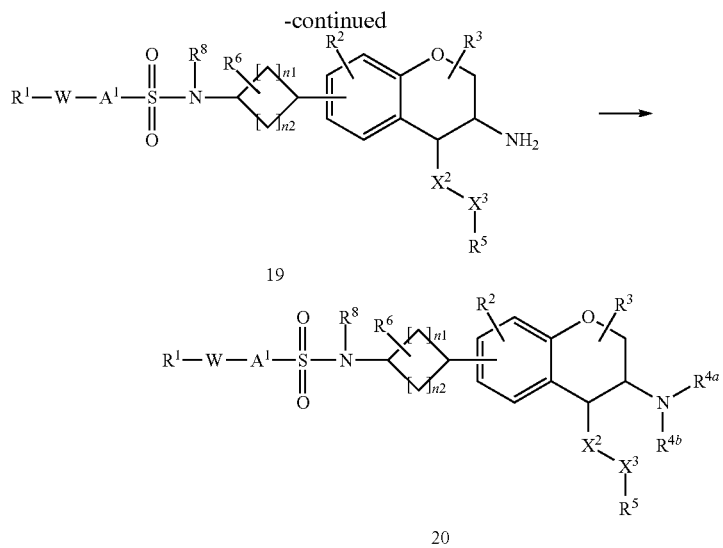

19

20

Triflates of the general formula 10 can be reacted with the corresponding alkyliodides in the presence of zink and palladium (e.g. zink, TMSCl, 1,2-dibromoethane, Pd(dba)2, and dppf) to undergoe a Negishi-coupling (Austr. J. Chem. 2004, 57, 107) and lead to compounds of the general formula 16. Alternatively, a Suzuki-coupling of the triflates 10 with the corresponding boron reagents (boronic acid, ester or trifluoroborates) in presence of a palladium source (e.g. palladiumdibenzylidine acetone), a ligand (e.g. 2-dicyclo-hexyl-phosphino-2',6'-diisopropoxybiphenyl) and a base (e.g. cesium carbonate) leads to the compounds of the general formula 16. Deprotection of the Boc-group in presence of an acid (e.g. trifluoroacetic acid or formic acid) leads to the compounds of the general formula 17. Treatment with sulfonyl chlorides in presence of a base (e.g. N,N-dimethylaminopyridine or pyridine) yields compound 18. Deprotection of the protecting group $L^3$ (for $L^3$=ethylcarbamate e.g. ethanolic potassium hydroxide) will lead to the free amine of the general formula 19. Reductive amination using the corresponding ketones or aldehydes in presence of a reduction reagent (e.g. sodiumcyanoborohydride and glacial acetic acid) or amide formation followed by subsequent reduction yields the corresponding higher alkylated amines of the general formula 20. Reduction of the ethylcarbamte ($L^3$) of compound 18 (e.g. using lithium aluminum hydride) leads directly to compounds of the general formula 20 with $R^{4a}$=methyl and $R^{4b}$=hydrogen or vice versa.

In scheme 4, the variables $R^1$, W, $A^1$, $R^2$, $R^3$, $R^{4a}$, $R^{4b}$, $R^5$, $R^6$, $R^8$, $X^2$, $X^3$, n1 and n2 are as defined herein, and $L^3$ is a suitable protecting groups (e.g. $L^3$=COOEt).

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IC_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}$<1 µMol, more preferably at a level of $IC_{50}$<0.5 µMol, particularly preferably at a level of $IC_{50}$<0.2 µMol and most preferably at a level of $IC_{50}$<0.1 µMol.

Compounds of formula (I) combine high affinity with high metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in therapeutic treatment. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

Amongst the compounds of the formula (I) those are particularly preferred which display good to moderate metabolic stability towards human liver microsomes. In particular, compounds of the formula (I) are preferred which display a microsomal clearance at a level of mClint,u<500 L/h/kg, more preferably at a level of mClint,u<100 L/h/kg, particularly preferably at a level of mClint,u<50 L/h/kg, and most preferably at a level of mClint,u<5 L/h/kg.

Further, compounds of formula (I) exhibit favorable efflux properties which may lead to enhanced oral bioavailability and/or increased brain availability. According to a particular embodiment, compounds of the invention combine high affinity and high metabolic stability with favorable efflux properties.

The efflux properties of a compound can be measured in well-known assays (e.g. Caco-2, MDCK assay).

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders. Further, glycine A receptors play a role in a variety of diseases in humans or other species. Increasing extracellular glycine concentrations by inhibiting glycine transport may enhance the activity of glycine A receptors. Glycine transport inhibitors and in particular inhibitors of the glycine transporter GlyT1 are thus useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including sub-stance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supra-nuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neuro-physiological processes and therefore tend to respond to different types of treatments. Acute pain can be somatic or visceral in nature. Somatic pain tends to be a well localised, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not ellicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive sub-optimal pain control rather than suffer these distressing side-effects. Furthermore, these side-effects often result in patients requiring extended hospitalisation. Opioids are highly addictive and are scheduled drugs in many territories.

The compounds of formula (I) are particularly useful in the treatment of schizophrenia, bipolar disorder, depression including unipolar depression, seasonal depression and post-partum depression, premenstrual syndrome (PMS) and pre-menstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of of the formula (I) include in particular a cognitive disorder such as dementia, cognitive impairment, attention deficit hyperactivity disorder.

Particular psychiatric disorders that can be treated with the compounds of of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being.

Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Cantor-Verlag, 1996.

The compounds of formula (I) may also be suitable for combination with other therapeutic agents.

Thus, the present invention also provides:
i) a combination comprising a compound of formula (I) with one or more further therapeutic agents;
ii) a pharmaceutical composition comprising a combination product as defined in i) above and at least one carrier, diluent or excipient;
iii) the use of a combination as defined in i) above in the manufacture of a medicament for treating or preventing a disorder, disease or condition as defined herein;
iv) a combination as defined in i) above for use in treating or preventing a disorder, disease or condition as defined herein;
v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration,
vi) a combination as defined in i) above for use in therapy;
vii) a method of treatment or prevention of a disorder, disease or condition as defined herein comprising administering an effective amount of a combination as defined in i) above;
viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) and at least one further therapeutic agent are within the scope of the current invention. In one embodiment of adjunctive therapeutic administration as described herein, a patient is typically stabilised on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I) to a patient receiving therapeutic administration of at least one antipsychotic agent. In a further aspect, the invention provides the use of compounds of formula (I) in the manufacture of a medicament for adjunctive therapeutic administration for the treatment of a psychotic disorder in a patient receiving therapeutic administration of at least one antipsychotic agent. The invention further provides compounds of formula (I) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I).

In a further aspect, the invention provides a method of treatment of a psychotic disorder by simultaneous therapeutic administration of compounds of formula (I) in combination with at least one antipsychotic agent. The invention further provides the use of a combination of compounds of formula (I) and at least one antipsychotic agent in the manufacture of a medicament for simultaneous therapeutic administration in the treatment of a psychotic disorder. The invention further provides a combination of compounds of formula (I) and at least one antipsychotic agent for simultaneous therapeutic administration in the treatment of a psychotic disorder. The invention further provides the use of compounds of formula (I) in the manufacture of a medicament for simultaneous therapeutic administration with at least one antipsychotic agent in the treatment of a psychotic disorder. The invention further provides compounds of formula (I) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) in the treatment of a psychotic disorder. The invention further provides at least one antipsychotic agent for simultaneous therapeutic administration with compounds of formula (I) in the treatment of a psychotic disorder.

In further aspects, the invention provides a method of treatment of a psychotic disorder by simultaneous therapeutic administration of a pharmaceutical composition comprising compounds of formula (I) and at least one mood stabilising or antimanic agent, a pharmaceutical composition comprising compounds of formula (I) and at least one mood stabilising or antimanic agent, the use of a pharmaceutical composition comprising compounds of formula (I) and at least one mood stabilising or antimanic agent in the manufacture of a medicament for the treatment of a psychotic disorder, and a pharmaceutical composition comprising compounds of formula (I) and at least one mood stabilising or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazinc, and acetophenazine; thioxanthenes, such as thiothixene and chlorprothixene; thienobenzodiazepines; dibenzodiazepines; benzisoxazoles; dibenzothiazepines; imidazolidinones; benzisothiazolyl-piperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE(D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRI N®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I) to a patient receiving therapeutic administration of at least one agent suitable for the treatment of a neurodegenerative disorder such as Alzheimer Disease. In a further aspect, the invention provides the use of compounds of formula (I) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I). The invention further provides at least one agent suitable for the treatment of a neurodegenerative disorder such as Alzheimer Disease for adjunctive therapeutic administration for the treatment of a neurodegenerative disorder such as Alzheimer Disease in a patient receiving therapeutic administration of compounds of formula (I).

In a further aspect, the invention provides a method of treatment of a neurodegenerative disorder such as Alzheimer Disease by simultaneous therapeutic administration of compounds of formula (I) in combination with at least one agent suitable for the treatment of a neurodegenerative disorder such as Alzheimer Disease. The invention further provides the use of a combination of compounds of formula (I) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I) and at least one agent suitable for the treatment of a neurodegenerative disorder such as Alzheimer Disease for simultaneous therapeutic administration in the treatment of a neurodegenerative disorder such as Alzheimer Disease. The invention further provides the use of compounds of formula (I) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acethylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipo-protein E variant 4 (ApoE4), disease-associated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1b antagonists.

In a further aspect therefore, the invention provides a method of treatment of pain by adjunctive therapeutic administration of compounds of formula (I) to a patient receiving therapeutic administration of at least one agent suitable for the treatment of pain. In a further aspect, the invention provides the use of compounds of formula (I) in the manufacture of a medicament for adjunctive therapeutic administration for the treatment of pain in a patient receiving therapeutic administration of at least one agent suitable for the treatment of pain. The invention further provides compounds of formula (I) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I). In a further aspect, the invention provides the use of at least one agent suitable for the treatment of pain in the manufacture of a medicament for adjunctive therapeutic administration for the treatment of pain in a patient receiving therapeutic administration of compounds of formula (I). The invention further provides at least one agent suitable for the treatment of pain for adjunctive therapeutic administration for the treatment of pain in a patient receiving therapeutic administration of compounds of formula (I).

In a further aspect, the invention provides a method of treatment of pain by simultaneous therapeutic administration of compounds of formula (I) in combination with at least one agent suitable for the treatment of pain. The invention further provides the use of a combination of compounds of formula (I) and at least one agent suitable for the treatment of pain in the manufacture of a medicament for simultaneous therapeutic administration in the treatment of pain. The invention further provides a combination of compounds of formula (I) and at least one agent suitable for the treatment of pain for simultaneous therapeutic administration in the treatment of pain. The invention further provides the use of compounds of formula (I) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I) in the treatment of pain. The invention further provides at least one agent suitable for the treatment of pain for simultaneous therapeutic administration with compounds of formula (I) in the treatment of pain.

Examples of agents suitable for the treatment of pain that are useful in the present invention include, but are not limited to: NSAIDs (Nonsteroidal Antiinflammatory Drugs), anticonvulsant drugs such as carbamazepine and gabapentin, sodium channel blockers, antidepressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1 B antagonists, 5HT1 D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

The following examples serve to explain the invention without limiting it.

The compounds were characterized by mass spectrometry, generally recorded via HPLC-MS in a fast gradient on C18-material (electrospray-ionisation (ESI) mode).

PREPARATION EXAMPLES

Example 1

N-[1-[3-(azetidin-1-yl)-4-benzyl-chroman-6-yl]azetidin-3-yl]-1-methyl-imidazole-4-sulfonamide

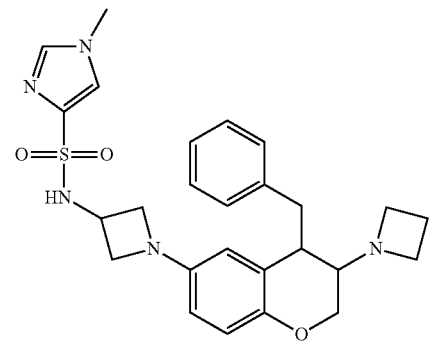 [SMILES: Cn1cnc(S(=O)(=O)NC2CN(c3ccc4c(c3)C(Cc3ccccc3)C(N3CCC3)CO4)C2)c1]

1.1 6-Methoxychroman-4-one oxime

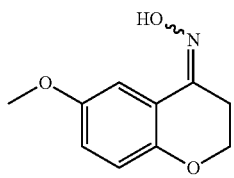

5.2 g (29.2 mmol) of 6-methoxychroman-4-one were dissolved in ethanol and 2.53 g (36.5 mmol) hydroxylamine hydrochloride and 2.99 g (36.5 mmol) sodium acetate dissolved in 10 ml of water were added. The mixture was stirred at 65° C. for 1.5 hours. The mixture was allowed to cool to room temperature and concentrated. The residue was dissolved in methyl-tert-butylether. The organic phase was washed with water, dried over MgSO$_4$ and concentrated to give 5.6 g (29.4 mmol, quant.) of crude product, which was directly used in the next step.

ESI-MS [M+H$^+$]=194 Calculated for C$_{10}$H$_{11}$NO$_3$=193.

1.2 6-Methoxychroman-4-one O-tosyl oxime

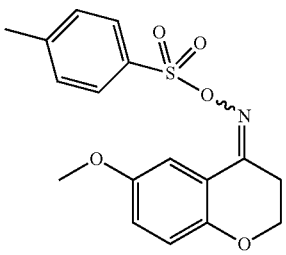 [SMILES: COc1ccc2c(c1)C(=NOS(=O)(=O)c1ccc(C)cc1)CCO2]

5.68 g (29.4 mmol) of 6-methoxychroman-4-one oxime were dissolved under argon atmosphere in 30 ml of dry pyridine. At 0° C. 6.05 g (31.8 mmol) of 4-methylbenzene-1-sulfonyl chloride were added in small portions over 40 min. The mixture was stirred at 0° C. for an additional hour and then warmed to room temperature and stirred over night. The mixture was poured into 260 ml ice water, stirred, and the suspension was filtered. The solid residue was washed with a small amount of cold water (2×) and cold ethanol (1×), and dried to yield 8.96 g (25.8 mmol, 88%) of desired product.

ESI-MS [M+H$^+$]=348 Calculated for C$_{17}$H$_{17}$NO$_5$S=347.

1.3 3-Amino-6-methoxychroman-4-one hydrochloride

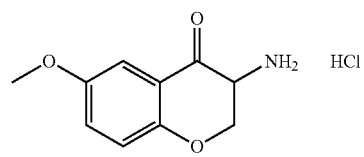

To a solution of sodium ethoxide (10.5 ml, 28.1 mmol, 21% in ethanol) under nitrogen atmosphere at 0° C. was added a suspension of 8.96 g (25.8 mmol) of (Z)-6-methoxy-chroman-4-one O-tosyl oxime in toluene. The mixture was stirred over night and slowly warmed to room temperature. The suspension was filtered and rinsed with ether. 95 ml (190 mmol) of an aqueous solution of hydrogen chloride (2 N) was added to the filtrate and stirred at room temperature for 2 h. The suspension was diluted with 150 ml of water and phases were separated. The organic phase was extracted with aqueous hydrogen chloride solution (2×, 20-30 ml, 1 N) and water (1×, 30 ml). The combined aqueous layers were washed with ether (1×). The aqueous phase was stirred with a small amount of activated charcoal, filtered, and concentrated to a ⅕ of its volume until a crystalline precipitation was observed. The mixture was cooled to 0° C. and the crystalline material was filtered off, washed with a small amount of cold ethanol, and dried in vacuo. The filtrate was also concentrated in vacuo. 3.67 g (15.98 mmol, 62%) of combined crude desired product was obtained. ESI-MS [M+H$^+$]=194 Calculated for C$_{10}$H$_{11}$NO$_3$=193.

1.4 Ethyl 6-methoxy-4-oxochroman-3-ylcarbamate

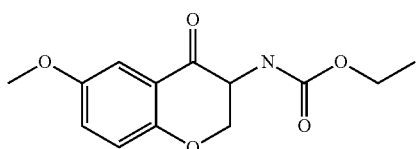

2.82 g (12.3 mmol) of 6-methoxy-4-oxochroman-3-aminium chloride were dissolved in tetrahydrofuran under nitrogen atmosphere and cooled to 0° C. with an ice bath. Diisopropylethylamine and ethyl carbononochloridate were added. The mixture was allowed to warm to room temperature and stirred for 30 min. The mixture was diluted with ethyl acetate and washed with saturated ammonium chloride solution (2×) and water (1×). The organic phase was washed, dried over MgSO$_4$, and concentrated in vacuo to give 3.5 g (13.2 mmol, quant.) of crude material.

ESI-MS [M+H$^+$]=265 Calculated for C$_{13}$H$_{15}$NO$_5$=266.

1.5 Ethyl 4-benzyl-4-hydroxy-6-methoxychroman-3-ylcarbamate

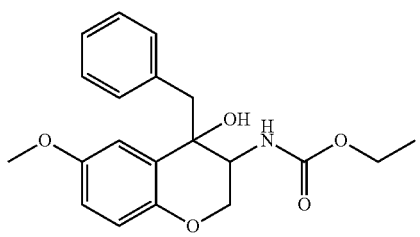 [SMILES: CCOC(=O)NC1COc2ccc(OC)cc2C1(O)Cc1ccccc1]

26.4 ml (52.8 mmol) of benzylmagnesium chloride under nitrogen atmosphere were cooled to 0° C. with an ice bath and 3.5 g (13.2 mmol) ethyl 6-methoxy-4-oxochroman-3-ylcarbamate dissolved in 100 ml dry THF were slowly added. The mixture was stirred at 0° C. for 1 h. The cooling bath was removed and saturated ammonium chloride solution was added. Water was added until a clear solution was obtained. The phases were separated and the organic phase was washed with saturated ammonium chloride solution, dried over MgSO₄, and concentrated in vacuo to give 6.87 g (9.1 mmol, quant.) of crude material.

ESI-MS [M+Na⁺]=380 Calculated for $C_{20}H_{23}NO_5$=357.

1.6 Ethyl 4-benzylidene-6-methoxychroman-3-ylcarbamate

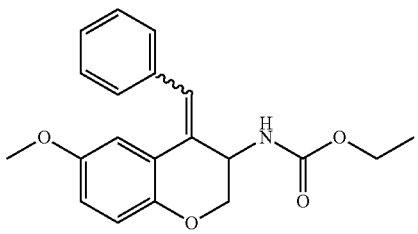 [SMILES: CCOC(=O)NC1COc2ccc(OC)cc2C1=Cc1ccccc1]

6.87 g (12.5 mmol) of ethyl 4-benzyl-4-hydroxy-6-methoxychroman-3-ylcarbamate were added to 80 ml of half concentrated aqueous hydrochloric acid and stirred at 100° C. for 2.5 h. The mixture was cooled to 0° C. and diluted with water. Sodium hydroxide (50% aqueous solution) was carefully added until pH>10. The aqueous phase was extracted with EtOAc (2×). The combined organic phases were washed with water and brine, dried over MgSO₄ and the solvent was evaporated to give 5.7 g of crude material. The crude material was purified by flash chromatography to yield 3.1 g (9.1 mmol, 73%) of the desired product.

ESI-MS [M+H⁺]=339 Calculated for $C_{20}H_{21}NO_4$=340.

1.7 Ethyl 4-benzyl-6-methoxychroman-3-ylcarbamate

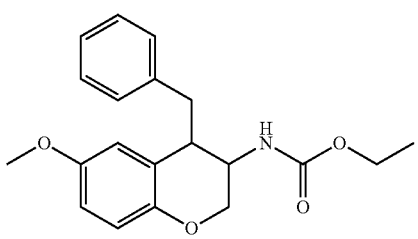 [SMILES: CCOC(=O)NC1COc2ccc(OC)cc2C1Cc1ccccc1]

3.1 g (9.1 mmol) of ethyl 4-benzylidene-6-methoxychroman-3-ylcarbamate were dissolved in 80 ml of EtOH and 910 mg (0.9 mmol) of Pd/C were added. Then, 5.8 g (91 mmol) of ammonium formiate dissolved in 20 ml of water were added and the mixture was warmed to 70° C. and stirred for 1.5 h. The mixture was cooled to room temperature. The catalyst was filtered off and washed with EtOH/water. The filtrate was concentrated in vacuo to remove EtOH. The aqueous concentrate was extracted with ethyl acetate (2×). The combined organic phases were dried over MgSO₄ and the solvent was evaporated to yield 3.2 g (9.3 mmol, quant.) of the crude product (cis:trans ~7:1). The cis-isomer can be enriched (~26:1) by crystallization from hot heptane.

ESI-MS [M+H⁺]=342 Calculated for $C_{20}H_{23}NO_4$=341.

1.8 Ethyl 4-benzyl-6-hydroxychroman-3-ylcarbamate

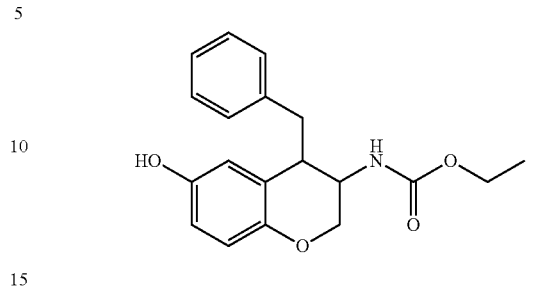

3.19 g (9.3 mmol) of ethyl 4-benzyl-6-methoxychroman-3-ylcarbamate under nitrogen atmosphere were dissolved in 90 ml of methylene dichloride. At 0° C. 28.0 ml (28.0 mmol, 1 M in methylene dichloride) of boron tribromide were added. The reaction mixture was stirred at 0° C. for 2 hours. At 0° C. saturated sodium hydrogencarbonate solution was added to the reaction mixture. The phases were separated and the aqueous phase was extracted with methylene dichloride. The combined organic layers were washed with brine, dried over MgSO₄ and the solvent was evaporated to yield 3.0 g (9.2 mmol, 99%) of the crude product.

ESI-MS [M+H⁺]=328 Calculated for $C_{19}H_{21}NO_4$=327.

1.9 Cis-3-Amino-4-benzylchroman-6-ol and trans-3-Amino-4-benzylchroman-6-ol

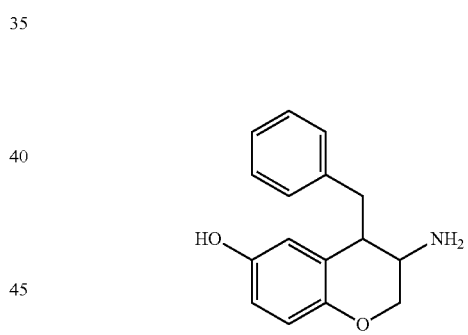

2.3 g (7.0 mmol) of ethyl 4-benzyl-6-hydroxychroman-3-ylcarbamate were dissolved in ethanolic KOH 20% and stirred at 70° C. over night. The solvent was evaporated, the residue partitioned between ethylacetate and water. The organic layer was washed twice with water and the combined water layer extracted another 2 times with ethyl acetate. The combined ethyl acetate extract was dried over MgSO₄, filtrated and evaporated. The crude material was purified by flash chromatography to yield 1.11 g (4.34 mmol, 62%) of cis-Isomer and 0.25 g (0.97 mmol, 14%) of the trans-Isomer.

Cis-Isomer: ESI-MS [M+H⁺]=256 Calculated for $C_{16}H_{17}NO_2$=255.

Trans-Isomer: ESI-MS [M+H⁺]=256 Calculated for $C_{16}H_{17}NO_2$=255.

1.10 Cis-3-(Azetidin-1-yl)-4-benzylchroman-6-ol

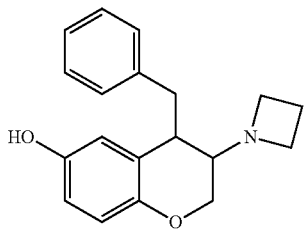 [SMILES: Oc1ccc2c(c1)C(Cc1ccccc1)C(N1CCC1)CO2]

0.9 g (3.57 mmol) of cis-3-amino-4-benzylchroman-6-ol, 0.36 mL (3.55 mmol) 1,3-dibromopropane and 1.9 mL (10.88 mmol) N-ethyl-N-isopropylpropan-2-amine were combined with 18 mL acetonitrile and stirred at 130° C. in the microwave (CEM) for 3 hours. Additional 75 µL 1,3-dibromopropane and 0.5 mL N-ethyl-N-isopropylpropan-2-amine were added to the reaction mixture (brown solution) and stirred at 130° C. in the microwave (CEM) for an additional 1 hour. The reaction mixture was evaporated and the obtained residue partitioned between water and ethyl acetate. The organic phase was washed with water and brine and the combined aqueous phases extracted twice with ethyl acetate. Combined organic extracts were dried over MgSO$_4$, filtrated and evaporated to dryness to yield 1 g of crude material. The material was purified by flash chromatography to yield 0.6 g (2.01 mmol, 56%) of desired product. ESI-MS [M+H$^+$]=296 Calculated for C$_{19}$H$_{2i}$NO$_2$=295.

1.11 Cis-3-(Azetidin-1-yl)-4-benzylchroman-6-yl trifluoromethanesulfonate

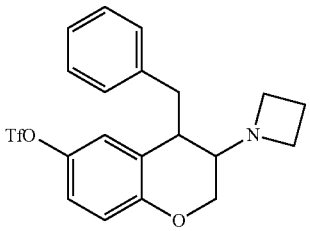 [SMILES: O=S(=O)(Oc1ccc2c(c1)C(Cc1ccccc1)C(N1CCC1)CO2)C(F)(F)F]

0.6 g (2.00 mmol) of cis-3-(Azetidin-1-yl)-4-benzylchroman-6-ol were dissolved in methylene chloride under nitrogen, 0.5 mL (6.18 mmol) pyridine were added and cooled with an ice bath to 0° C. 2.2 mL (2.20 mmol) trifluoromethanesulfonic anhydride were added and the reaction mixture stirred under cooling for 1 hour. The reaction mixture was quenched with aqueous bicarbonate solution, and the aqueous phase separated and extracted with methylene chloride once. The combined organic layers were washed with water (2x) and brine (1x), dried over MgSO$_4$, filtrated and evaporated to dryness to yield 0.8 g of crude material.

ESI-MS [M+H$^+$]=427 Calculated for C$_{20}$H$_{20}$F$_3$NO$_4$S=428.

1.12 Cis-tert-Butyl(1-(3-(azetidin-1-yl)-4-benzylchroman-6-yl)azetidin-3-yl)carbamate

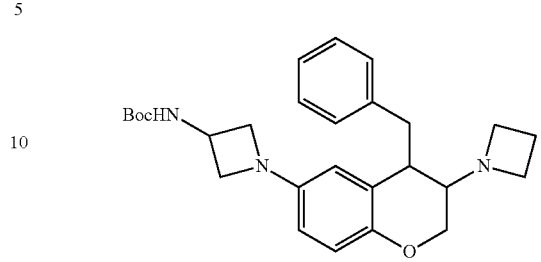

0.2 g (0.36 mmol) of cis-3-(azetidin-1-yl)-4-benzylchroman-6-yl trifluoromethanesulfonate were dissolved in toluene under nitrogen, 0.01 g (0.05 mmol) Pd(II) acetate, 0.05 g (0.11 mmol) dicyclohexyl(2',4',6'-triisopropyl-[1,1'-biphenyl]-2-yl)phosphine (x-Phos) and 0.35 g (1.07 mmol) cesium carbonate were added to this solution and the resulting mixture stirred at 115° C. for 15 min. Then, 0.09 g (0.43 mmol) of 3-((tert-butoxycarbonyl)amino)azetidin-1-ium chloride was added and the reaction mixture stirred for 30 min. at 115° C. The reaction mixture was allowed to cool at room temperature, the solvent evaporated, and the residue extracted between water and ethyl acetate. The organic phase was washed with brine, dried over MgSO$_4$, filtered and evaporated. The crude material was purified by flash chromatography to yield 0.15 g (0.33 mmol, 93%).

ESI-MS [M+H$^+$]=450 Calculated for C$_{27}$H$_{35}$N$_3$O$_3$=449.

1.13 Cis-1-(3-(azetidin-1-yl)-4-benzylchroman-6-yl)azetidin-3-amine

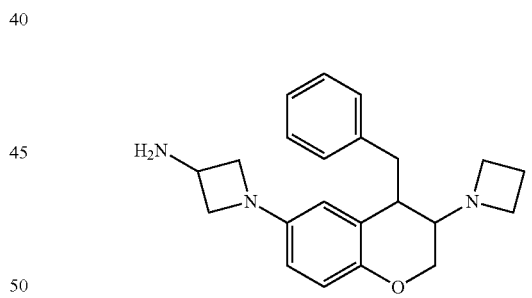

0.15 g (0.33 mmol) of cis-tert-butyl (1-(3-(azetidin-1-yl)-4-benzylchroman-6-yl)azetidin-3-yl)carbamate were dissolved in methylene chloride, 0.25 mL (3.24 mmol) trifluoroacetic acid were added and the reaction mixture stirred at room temperature overnight. The solvents were evaporated. The residue was dissolved in water and washed twice with methyl-tert-butyl ether. The water layer was separated, aqueous sodium bicarbonate solution was added until pH 8 was reached, and extracted with methylene chloride (3x). The combined organic extracts were dried over MgSO$_4$ and concentrated to yield 0.10 g (0.29 mmol) of crude material.

ESI-MS [M+H$^+$]=350 Calculated for C$_{22}$H$_{27}$N$_3$O=349.

1.14 Cis-N-(1-(3-(azetidin-1-yl)-4-benzylchroman-6-yl)azetidin-3-yl)-1-methyl-1H-imidazole-4-sulfonamide

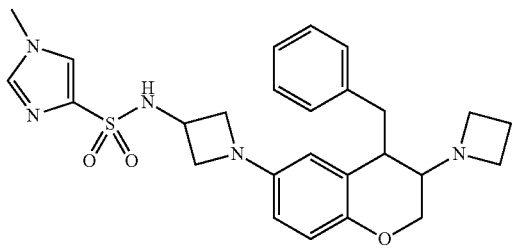 [SMILES: Cn1cnc(S(=O)(=O)NC2CN(c3ccc4c(c3)C(Cc3ccccc3)C(N3CCC3)CO4)C2)c1]

0.05 g (0.14 mmol) of 1-(3-(azetidin-1-yl)-4-benzylchroman-6-yl)azetidin-3-amine were dissolved in methylene chloride, 0.05 g (0.37 mmol) N,N-dimethylpyridin-4-amine and 0.03 g (0.19 mmol) 1-methyl-1H-imidazole-4-sulfonyl chloride were added. The reaction mixture was stirred at room temperature for 30 min. The solvent was evaporated and the residue partitioned between ethyl acetate and water. The organic layer was washed twice with water, dried over MgSO$_4$, filtrated and evaporated. The crude material was purified by flash chromatography to yield 0.06 g (0.11 mmol, 81%) of desired product.

ESI-MS [M+H$^+$]=494 Calculated for $C_{26}H_{31}N_5O_3S$=349.

Example 2

Cis-N-(1-(3-(azetidin-1-yl)-4-benzylchroman-6-yl)azetidin-3-yl)ethanesulfonamide

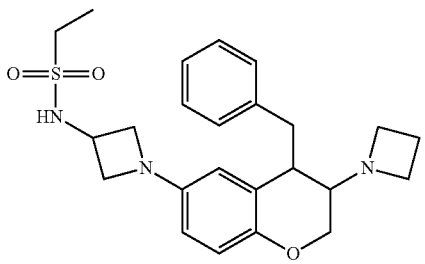 [SMILES: CCS(=O)(=O)NC1CN(c2ccc3c(c2)C(Cc2ccccc2)C(N2CCC2)CO3)C1]

Cis-N-(1-(3-(azetidin-1-yl)-4-benzylchroman-6-yl)azetidin-3-yl)ethanesulfonamide was prepared in analogy to example 1.

ESI-MS [M+H$^+$]=442 Calculated for $C_{24}H_{31}N_3O_3S$=441.

Example 3

Cis-N-(1-(3-(azetidin-1-yl)-4-benzylchroman-6-yl)azetidin-3-yl)propane-1-sulfonamide

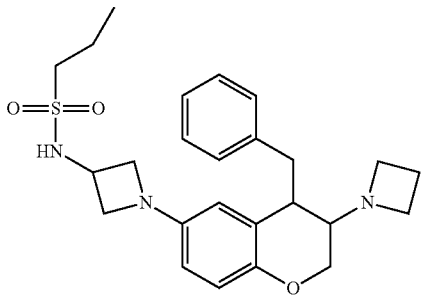 [SMILES: CCCS(=O)(=O)NC1CN(c2ccc3c(c2)C(Cc2ccccc2)C(N2CCC2)CO3)C1]

Cis-N-(1-(3-(azetidin-1-yl)-4-benzylchroman-6-yl)azetidin-3-yl)propane-1-sulfonamide was prepared in analogy to example 1.

ESI-MS [M+H$^+$]=456 Calculated for $C_{25}H_{33}N_3O_3S$=455.

Example 4

Cis-N-(1-(3-(azetidin-1-yl)-4-benzylchroman-6-yl)azetidin-3-yl)-1-cyclopropylmethanesulfonamide

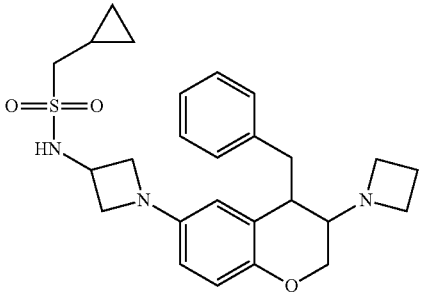 [SMILES: O=S(=O)(CC1CC1)NC1CN(c2ccc3c(c2)C(Cc2ccccc2)C(N2CCC2)CO3)C1]

Cis-N-(1-(3-(azetidin-1-yl)-4-benzylchroman-6-yl)azetidin-3-yl)-1-cyclopropylmethanesulfonamide was prepared in analogy to example 1.

ESI-MS [M+H$^+$]=468 Calculated for $C_{26}H_{33}N_3O_3S$=467.

Example 5

Cis-N-(1-(3-(azetidin-1-yl)-4-benzylchroman-6-yl)azetidin-3-yl)-1-methyl-1H-pyrazole-4-sulfonamide

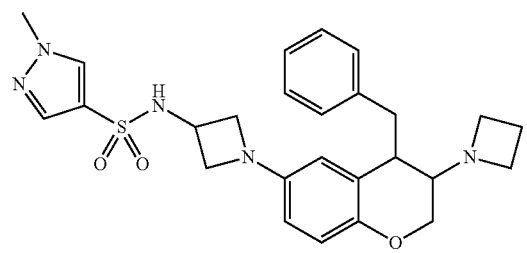 [SMILES: Cn1cc(S(=O)(=O)NC2CN(c3ccc4c(c3)C(Cc3ccccc3)C(N3CCC3)CO4)C2)cn1]

Cis-N-(1-(3-(azetidin-1-yl)-4-benzylchroman-6-yl)azetidin-3-yl)-1-methyl-1H-pyrazole-4-sulfonamide was prepared in analogy to example 1.

ESI-MS [M+H$^+$]=494 Calculated for $C_{26}H_{31}N_5O_3S$=493.

Example 6

Cis-N-(1-(3-(azetidin-1-yl)-4-benzylchroman-6-yl)azetidin-3-yl)-1-methyl-1H-1,2,3-triazole-4-sulfonamide

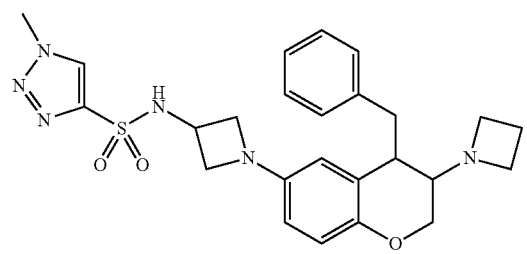 [SMILES: Cn1cc(S(=O)(=O)NC2CN(c3ccc4c(c3)C(Cc3ccccc3)C(N3CCC3)CO4)C2)nn1]

Cis-N-(1-(3-(azetidin-1-yl)-4-benzylchroman-6-yl)azetidin-3-yl)-1-methyl-1H-1,2,3-triazole-4-sulfonamide was prepared in analogy to example 1.

ESI-MS [M+H$^+$]=495 Calculated for $C_{25}H_{30}N_6O_3S$=494.

Example 7

Cis-N-(1-(3-(azetidin-1-yl)-4-benzyl-7-fluorochroman-6-yl)azetidin-3-yl)-1-ethyl-1H-1,2,3-triazole-4-sulfonamide

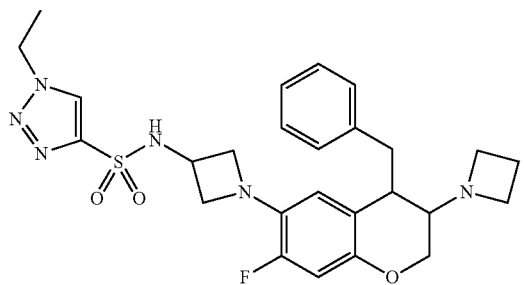 [SMILES: CCn1cc(S(=O)(=O)NC2CN(c3cc4c(cc3F)OCC(N3CCC3)C4Cc3ccccc3)C2)nn1]

Cis-N-(1-(3-(azetidin-1-yl)-4-benzyl-7-fluorochroman-6-yl)azetidin-3-yl)-1-ethyl-1H-1,2,3-triazole-4-sulfonamide was prepared in analogy to example 1.
ESI-MS [M+H$^+$]=527 Calculated for C$_{26}$H$_{31}$FN$_6$O$_3$S=526.

Example 8

Cis-N-(1-(3-(azetidin-1-yl)-4-benzyl-7-fluorochroman-6-yl)azetidin-3-yl)-2-fluoropyridine-3-sulfonamide

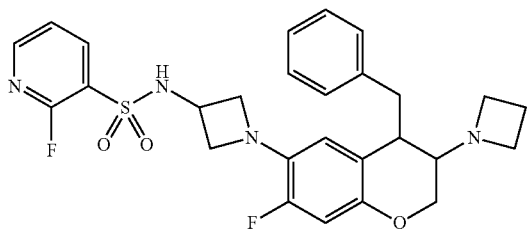 [SMILES: O=S(=O)(NC1CN(c2cc3c(cc2F)OCC(N2CCC2)C3Cc2ccccc2)C1)c1cccnc1F]

Cis-N-(1-(3-(azetidin-1-yl)-4-benzyl-7-fluorochroman-6-yl)azetidin-3-yl)-2-fluoropyridine-3-sulfonamide was prepared in analogy to example 1.
ESI-MS [M+H$^+$]=527 Calculated for C$_{27}$H$_{28}$F$_2$N$_4$O$_3$S=526.

Example 9

Cis-N-(1-(3-(azetidin-1-yl)-4-benzyl-7-fluorochroman-6-yl)azetidin-3-yl)pyridazine-3-sulfonamide

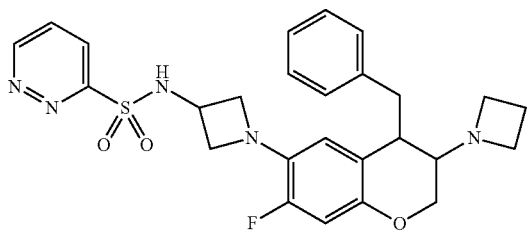 [SMILES: O=S(=O)(NC1CN(c2cc3c(cc2F)OCC(N2CCC2)C3Cc2ccccc2)C1)c1cccnn1]

Cis-N-(1-(3-(azetidin-1-yl)-4-benzyl-7-fluorochroman-6-yl)azetidin-3-yl)pyridazine-3-sulfonamide was prepared in analogy to example 1.
ESI-MS [M+H$^+$]=510 Calculated for C$_{26}$H$_{28}$FN$_5$O$_3$S=509.

Example 10

Cis-N-(1-(3-(azetidin-1-yl)-4-benzylchroman-6-yl)azetidin-3-yl)-2-fluoropyridine-3-sulfonamide

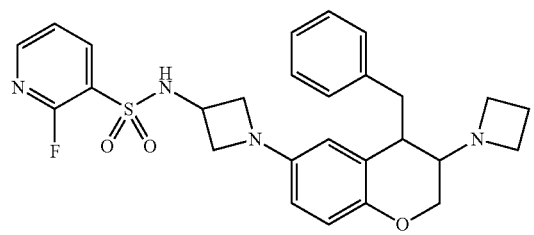 [SMILES: O=S(=O)(NC1CN(c2ccc3c(c2)C(Cc2ccccc2)C(N2CCC2)CO3)C1)c1cccnc1F]

Cis-N-(1-(3-(azetidin-1-yl)-4-benzylchroman-6-yl)azetidin-3-yl)-2-fluoropyridine-3-sulfonamide was prepared in analogy to example 1.
ESI-MS [M+H$^+$]=509 Calculated for C$_{27}$H$_{29}$FN$_4$O$_3$S=508.

Example 11

Cis-N-(1-(4-benzyl-3-(methylamino)chroman-6-yl)azetidin-3-yl)propane-1-sulfonamide

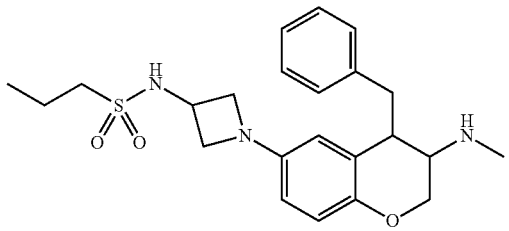 [SMILES: CCCS(=O)(=O)NC1CN(c2ccc3c(c2)C(Cc2ccccc2)C(NC)CO3)C1]

11.1
Cis-4-benzyl-3-((ethoxycarbonyl)amino)chroman-6-yl trifluoromethanesulfonate

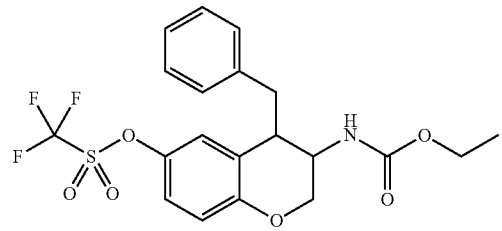 [SMILES: CCOC(=O)NC1COc2ccc(OS(=O)(=O)C(F)(F)F)cc2C1Cc1ccccc1]

Cis-4-benzyl-3-((ethoxycarbonyl)amino)chroman-6-yl trifluoromethanesulfonate was prepared starting from cis-ethyl 4-benzyl-6-hydroxychroman-3-ylcarbamate (Example 1, 1.8). 4.9 g (14.97 mmol) of 4-benzyl-3-((ethoxycarbonyl)

amino)chroman-6-yl trifluoromethanesulfonate were dissolved in methylene chloride under nitrogen atmosphere, 3.0 mL (37.4 mmol) pyridine were added and cooled to 0° C. with an ice bath. Then, 16.5 mL (16.5 mmol) trifluoromethanesulfonic anhydride (1 M in methylene chloride) were added and the reaction mixture stirred under cooling for 0.5 hour. The reaction mixture was quenched with aqueous ammonium chloride solution, the phases were separated, and the aqueous phase was extracted with methylene chloride once. The combined organic layers were washed with aqueous ammonium chloride solution and brine, dried over MgSO$_4$, filtrated, and evaporated to dryness to yield 6.6 g (14.37 mmol, 96%) of crude product.

ESI-MS [M+H$^+$]=460 Calculated for $C_{20}H_{20}F_3NO_6S$=459.

11.2 Cis-tert-Butyl(1-(3-(azetidin-1-yl)-4-benzyl-3-((ethoxycarbonyl)amino)chroman-6-yl carbamate

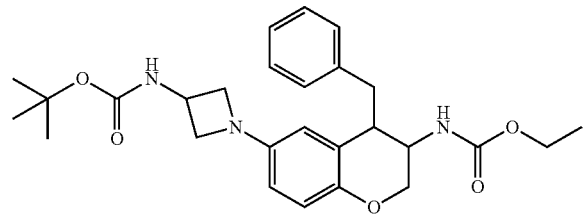 [SMILES: CCOC(=O)NC1COc2ccc(N3CC(NC(=O)OC(C)(C)C)C3)cc2C1Cc1ccccc1]

6.0 g (13.06 mmol) of cis-4-benzyl-3-((ethoxycarbonyl) amino)chroman-6-yl trifluoromethanesulfonate were dissolved in toluene under nitrogen atmosphere, 0.44 g (1.96 mmol) Pd(II) acetate, 1.87 g (3.92 mmol) dicyclohexyl(2', 4',6'-triisopropyl-[1,1'-biphenyl]-2-yl)phosphine, and 10.64 g (32.6 mmol) cesium carbonate were added to this solution and the resulting mixture stirred at 115° C. for 15 min. Then, 3-((tert-butoxycarbonyl)amino)azetidin-1-ium chloride was added and the reaction mixture stirred for 1.5 h at 115° C. The mixture was cooled to room temperature, the solvent was evaporated, and the residue extracted between water and ethyl acetate. The organic phase was washed with water and brine, dried over MgSO$_4$, filtered, and evaporated. The crude material was purified by flash chromatography to yield 7.8 g (12.15 mmol, 93%) of the desired product.

ESI-MS [M+H$^+$]=482 Calculated for $C_{27}H_{35}N_3O_5$=481.

11.3 Cis-ethyl(-6-(3-aminoazetidin-1-yl)-4-benzyl-chroman-3-yl)carbamate

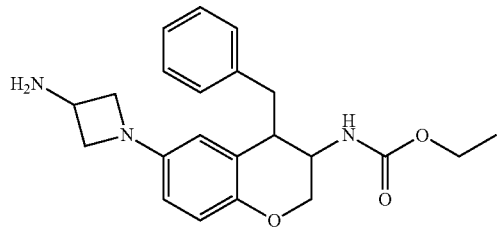 [SMILES: CCOC(=O)NC1COc2ccc(N3CC(N)C3)cc2C1Cc1ccccc1]

7.8 g (12.15 mmol) of cis-tert-butyl(1-(3-(azetidin-1-yl)-4-benzyl-3-((ethoxycarbonyl)amino)chroman-6-yl carbamate were dissolved in methylene chloride, 9.0 mL (117 mmol) trifluoroacetic acid were added, and the reaction mixture stirred at room temperature over night. The solvent was evaporated, the residue dissolved in water and washed with methyl-tert-butylether. The organic layer was washed with water additional 3×. To the combined water layers aqueous sodium bicarbonate solution was added until pH 8 was reached and extracted with methylene chloride (3×). The combined methylene dichloride extracts were dried over MgSO4 and concentrated to yield 4.33 g (11.35 mmol, 93%).

ESI-MS [M+H$^+$]=382 Calculated for $C_{22}H_{27}N_3O_5$=381.

11.4 Cis-ethyl(-4-benzyl-6-(3-(propylsulfonamido) azetidin-1-yl)chroman-3-yl)carbamate

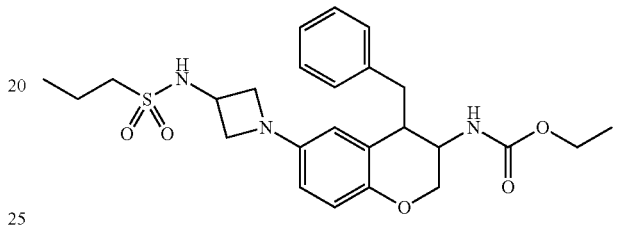

1.5 g (3.93 mmol) of cis-ethyl(-6-(3-aminoazetidin-1-yl)-4-benzylchroman-3-yl)carbamate were dissolved in methylene dichloride, 1.2 g (9.83 mmol) N,N-dimethylpyridin-4-amine, and 0.60 mL (5.39 mmol) propane-1-sulfonyl chloride were added. The reaction mixture was stirred for 1 h at room temperature. The solvent was evaporated and the residue partitioned between ethyl acetate and water. The organic layer was washed twice with water and once with brine, dried over MgSO$_4$, filtrated, and concentrated. The crude material was purified by flash chromatography to yield 1.74 g (3.57 mmol, 91%) of the desired product.

ESI-MS [M+H$^+$]=382 Calculated for $C_{22}H_{27}N_3O_5S$=381.

11.5 Cis-ethyl(-4-benzyl-6-(3-(propylsulfonamido) azetidin-1-yl)chroman-3-yl)carbamate

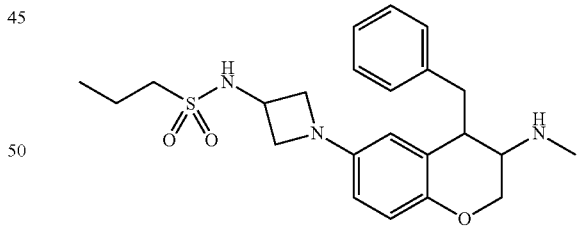

1.74 g (3.57 mmol) of cis-ethyl(-4-benzyl-6-(3-(propylsulfonamido)azetidin-1-yl)chroman-3-yl)carbamate were dissolved in tetrahydrofuran under nitrogen atmosphere, 18 mL (18 mmol) lithium aluminium hydride solution (1 M in tetrahydrofuran) were added, and the reaction mixture stirred at reflux for 1 h. The reaction mixture was cooled to room temperature, the excess of lithium aluminium hydride quenched with methanol, and the solvent was evaporated. The residue was partitioned between ethyl acetate and water. The resulting mixture was filtered through celite. Filtrate: aqueous layer was separated and extracted with ethyl acetate. The combined organic layers were dried over MgSO$_4$, filtered, and concentrated. The crude material was purified by flash chromatography to yield 1.42 g (3.32 mmol, 93%) of the desired product.

ESI-MS [M+H$^+$]=430 Calculated for C$_{23}$H$_{31}$N$_3$O$_3$S=429.

Example 12

Cis-N-(1-(-4-benzyl-3-(methylamino)chroman-6-yl)azetidin-3-yl)ethanesulfonamide

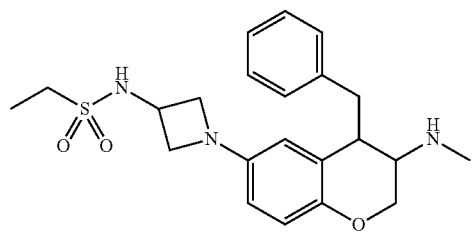 [SMILES: CCS(=O)(=O)NC1CN(c2ccc3c(c2)C(Cc2ccccc2)C(NC)CO3)C1]

Cis-N-(1-(-4-benzyl-3-(methylamino)chroman-6-yl)azetidin-3-yl)ethanesulfonamide was prepared in analogy to example 11.

ESI-MS [M+H$^+$]=416 Calculated for C$_{22}$H$_{29}$N$_3$O$_3$S=415.

Example 13

Cis-N-(1-(4-benzyl-3-(methylamino)chroman-6-yl)azetidin-3-yl)-1-cyclopropylmethanesulfonamide

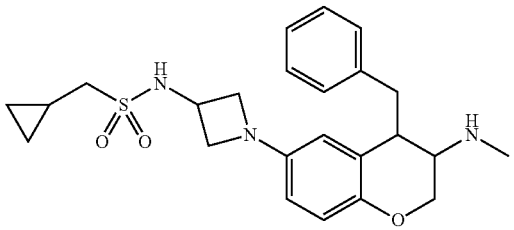 [SMILES: CNC1COc2ccc(N3CC(NS(=O)(=O)CC4CC4)C3)cc2C1Cc1ccccc1]

Cis-N-(1-(4-benzyl-3-(methylamino) chroman-6-yl)azetidin-3-yl)-1-cyclopropylmethanesulfonamide was prepared in analogy to example 11.

ESI-MS [M+H$^+$]=442 Calculated for C$_{24}$H$_{31}$N$_3$O$_3$S=441.

Example 14

Cis-N-(1-(4-benzyl-7-fluoro-3-(methylamino)chroman-6-yl)azetidin-3-yl)ethanesulfonamide and trans-N-(1-(4-benzyl-7-fluoro-3-(methylamino)chroman-6-yl)azetidin-3-yl)ethanesulfonamide

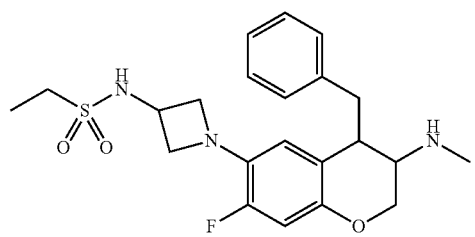 [SMILES: CCS(=O)(=O)NC1CN(c2cc3c(cc2F)OCC(NC)C3Cc2ccccc2)C1]

Cis-N-(1-(4-benzyl-7-fluoro-3-(methylamino)chroman-6-yl)azetidin-3-yl)ethanesulfonamide and trans-N-(1-(4-benzyl-7-fluoro-3-(methylamino)chroman-6-yl)azetidin-3-yl)ethanesulfonamide were prepared in analogy to example 11.

14a. Cis-isomer: ESI-MS [M+H$^+$]=434 Calculated for C$_{22}$H$_{28}$FN$_3$O$_3$S=433.

14b. Trans-isomer: ESI-MS [M+H$^+$]=434 Calculated for C$_{22}$H$_{28}$FN$_3$O$_3$S=433.

Example 15

Cis-N-(1-(4-benzyl-7-fluoro-3-(methylamino)chroman-6-yl)azetidin-3-yl)-1-methyl-1H-imidazole-4-sulfonamide and trans-N-(1-(4-benzyl-7-fluoro-3-(methylamino)chroman-6-yl)azetidin-3-yl)-1-methyl-1H-imidazole-4-sulfonamide

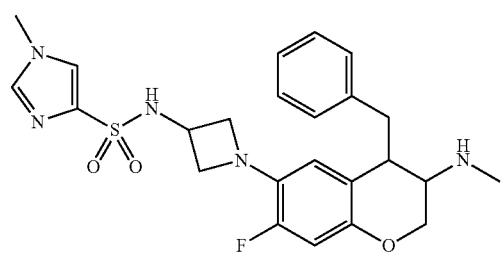 [SMILES: CNC1COc2cc(F)c(N3CC(NS(=O)(=O)c4cn(C)cn4)C3)cc2C1Cc1ccccc1]

Cis-N-(1-(4-benzyl-7-fluoro-3-(methylamino)chroman-6-yl)azetidin-3-yl)-1-methyl-1H-imidazole-4-sulfonamide and trans-N-(1-(4-benzyl-7-fluoro-3-(methylamino)chroman-6-yl)azetidin-3-yl)-1-methyl-1H-imidazole-4-sulfonamide were prepared in analogy to example 11.

15a. Cis-isomer: ESI-MS [M+H$^+$]=486 Calculated for C$_{24}$H$_{28}$FN$_5$O$_3$S=485.

15b. Trans-isomer: ESI-MS [M+H$^+$]=486 Calculated for C$_{24}$H$_{28}$FN$_5$O$_3$S=485.

Example 16

Cis-N-(1-(4-benzyl-7-fluoro-3-(methylamino)chroman-6-yl)azetidin-3-yl)propane-1-sulfonamide and trans-N-(1-(4-benzyl-7-fluoro-3-(methylamino)chroman-6-yl)azetidin-3-yl)propane-1-sulfonamide

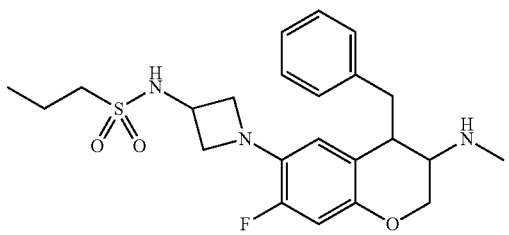 [SMILES: CCCS(=O)(=O)NC1CN(c2cc3c(cc2F)OCC(NC)C3Cc2ccccc2)C1]

Cis-N-(1-(4-benzyl-7-fluoro-3-(methylamino)chroman-6-yl)azetidin-3-yl)propane-1-sulfonamide and trans-N-(1-(4-benzyl-7-fluoro-3-(methylamino)chroman-6-yl)azetidin-3-yl)propane-1-sulfonamide were prepared in analogy to example 11.

16a. Cis-isomer: ESI-MS [M+H$^+$]=448 Calculated for C$_{23}$H$_{30}$FN$_3$O$_3$S=447.

16b. Trans-isomer: ESI-MS [M+H$^+$]=448 Calculated for C$_{23}$H$_{30}$FN$_3$O$_3$S=447.

Example 17

Cis-N-(1-(4-benzyl-7-fluoro-3-(methylamino)chroman-6-yl)azetidin-3-yl)-1-methyl-1H-pyrazole-4-sulfonamide and trans-N-(1-(4-benzyl-7-fluoro-3-(methylamino)chroman-6-yl)azetidin-3-yl)-1-methyl-1H-pyrazole-4-sulfonamide

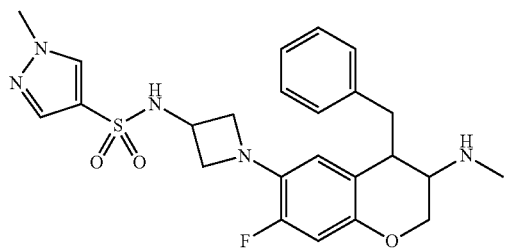 [SMILES: CNC1COc2cc(F)c(N3CC(NS(=O)(=O)c4cnn(C)c4)C3)cc2C1Cc1ccccc1]

Cis-N-(1-(4-benzyl-7-fluoro-3-(methylamino)chroman-6-yl)azetidin-3-yl)-1-methyl-1H-pyrazole-4-sulfonamide and trans-N-(1-(4-benzyl-7-fluoro-3-(methylamino)chroman-6-yl)azetidin-3-yl)-1-methyl-1H-pyrazole-4-sulfonamide were prepared in analogy to example 11.

17a. Cis-isomer: ESI-MS [M+H$^+$]=486 Calculated for $C_{24}H_{28}FN_5O_3S$=485.

17b. Trans-isomer: ESI-MS [M+H$^+$]=486 Calculated for $C_{24}H_{28}FN_5O_3S$=485.

Example 18

Cis-N-(1-(4-benzyl-7-fluoro-3-(methylamino)chroman-6-yl)azetidin-3-yl)-1-methyl-1H-1,2,3-triazole-4-sulfonamide and trans-N-(1-(4-benzyl-7-fluoro-3-(methylamino)chroman-6-yl)azetidin-3-yl)-1-methyl-1H-1,2,3-triazole-4-sulfonamide

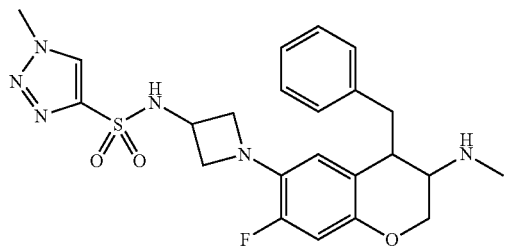 [SMILES: CNC1COc2cc(F)c(N3CC(NS(=O)(=O)c4cn(C)nn4)C3)cc2C1Cc1ccccc1]

Cis-N-(1-(4-benzyl-7-fluoro-3-(methylamino)chroman-6-yl)azetidin-3-yl)-1-methyl-1H-1,2,3-triazole-4-sulfonamide and trans-N-(1-(4-benzyl-7-fluoro-3-(methylamino)chroman-6-yl)azetidin-3-yl)-1-methyl-1H-1,2,3-triazole-4-sulfonamide were prepared in analogy to example 11.

18a. Cis-isomer: ESI-MS [M+H$^+$]=487 Calculated for $C_{23}H_{27}FN_6O_3S$=486.

18b. Trans-isomer: ESI-MS [M+H$^+$]=487 Calculated for $C_{23}H_{27}FN_6O_3S$=486.

Example 19

Cis-N-(1-(4-benzyl-7-fluoro-3-(methylamino)chroman-6-yl)azetidin-3-yl)-1-cyclopropylmethanesulfonamide and trans-N-(1-(4-benzyl-7-fluoro-3-(methylamino)chroman-6-yl)azetidin-3-yl)-1-cyclopropylmethanesulfonamide

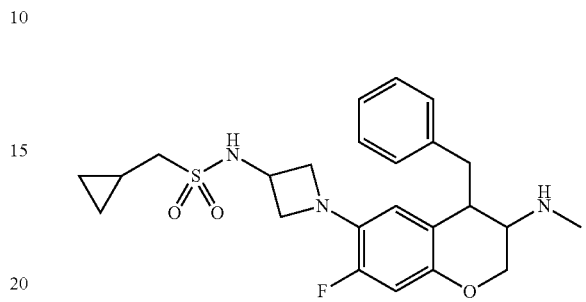

Cis-N-(1-(4-benzyl-7-fluoro-3-(methylamino)chroman-6-yl)azetidin-3-yl)-1-cyclopropylmethanesulfonamide and trans-N-(1-(4-benzyl-7-fluoro-3-(methylamino)chroman-6-yl)azetidin-3-yl)-1-cyclopropylmethanesulfonamide were prepared in analogy to example 11.

19a. Cis-isomer: ESI-MS [M+H$^+$]=460 Calculated for $C_{24}H_{30}FN_3O_3S$=459.

19b. Trans-isomer: ESI-MS [M+H$^+$]=460 Calculated for $C_{24}H_{30}FN_3O_3S$=459.

Example 20

Cis-N-(1-(3-amino-4-benzylchroman-6-yl)azetidin-3-yl)propane-1-sulfonamide

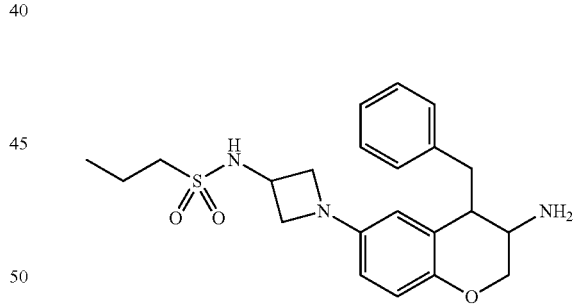

0.04 g (0.08 mmol) of cis-ethyl(-4-benzyl-6-(3-(propylsulfonamido)azetidin-1-yl)chroman-3-yl)carbamate (Example 11, 11.4) were dissolved in ethanolic potassium hydroxide solution (20%) and stirred at 90° C. in the microwave for 15 min. The solvent was evaporated and the residue partitioned between ethyl acetate and water. The organic layer was washed twice with water and the combined water layers were extracted another 2× with ethyl acetate. The combined ethyl acetate extracts were dried over MgSO$_4$, filtrated, and concentrated. The crude material was purified by flash chromatography to yield 0.03 g (0.06 mmol, 82%) of the desired product.

ESI-MS [M+H$^+$]=416 Calculated for $C_{22}H_{29}N_3O_3S$=415.

Example 21

Cis-N-(1-(3-amino-4-benzylchroman-6-yl)azetidin-3-yl)-1-cyclopropylmethanesulfonamide

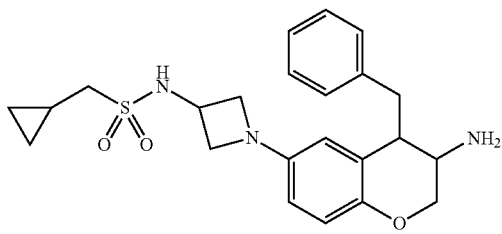 [SMILES: NC1COc2ccc(N3CC(NS(=O)(=O)CC4CC4)C3)cc2C1Cc1ccccc1]

Cis-N-(1-(3-amino-4-benzylchroman-6-yl)azetidin-3-yl)-1-cyclopropylmethanesulfonamide was prepared in analogy to example 20.

ESI-MS [M+H$^+$]=428 Calculated for $C_{23}H_{29}N_3O_3S$=427.

Example 22

Cis-N-(1-(4-benzyl-3-(methylamino)chroman-6-yl)azetidin-3-yl)propane-1-sulfonamide—Isomer 1

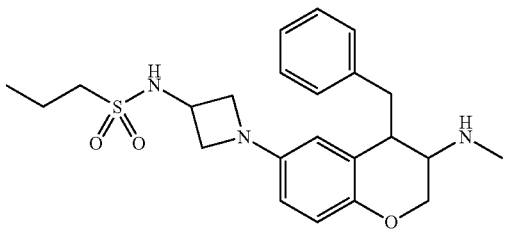 [SMILES: CCCS(=O)(=O)NC1CN(c2ccc3c(c2)C(Cc2ccccc2)C(NC)CO3)C1]

Cis-N-(1-(4-benzyl-3-(methylamino)chroman-6-yl)azetidin-3-yl)propane-1-sulfonamide was prepared by separation of the racemic mixture obtained in example 11 through chiral chromatography on Daicel Chiralpak (n-heptane ethanol 65:35+0.1% triethylamine) and isolation of the isomer as the first eluting peak.

ESI-MS [M+H$^+$]=430 Calculated for $C_{23}H_{31}N_3O_3S$=429.

Example 23

Cis-N-(1-(4-benzyl-3-(methylamino)chroman-6-yl)azetidin-3-yl)propane-1-sulfonamide—Isomer 2

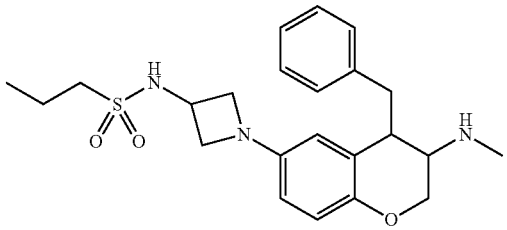 [SMILES: CCCS(=O)(=O)NC1CN(c2ccc3c(c2)C(Cc2ccccc2)C(NC)CO3)C1]

Cis-N-(1-(4-benzyl-3-(methylamino)chroman-6-yl)azetidin-3-yl)propane-1-sulfonamide was prepared by separation of the racemic mixture obtained in example 11 through chiral chromatography on Daicel Chiralpak (n-heptane ethanol 65:35+0.1% triethylamine) and isolation of the isomer as the second eluting peak.

ESI-MS [M+H$^+$]=430 Calculated for $C_{23}H_{31}N_3O_3S$=429.

Example 24

Cis-N-(1-(4-benzyl-3-(methylamino)chroman-6-yl)azetidin-3-yl)-1-cyclopropylmethanesulfonamide—Isomer 1

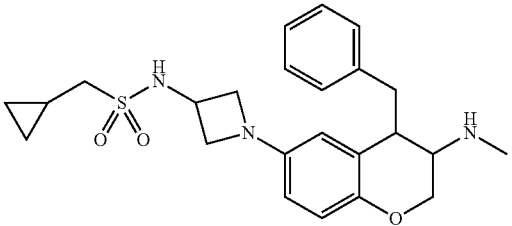 [SMILES: CNC1COc2ccc(N3CC(NS(=O)(=O)CC4CC4)C3)cc2C1Cc1ccccc1]

Cis-N-(1-(4-benzyl-3-(methylamino)chroman-6-yl)azetidin-3-yl)-1-cyclopropylmethanesulfonamide was prepared by separation of the racemic mixture obtained in example 13 through chiral chromatography on Daicel Chiralpak (n-heptane ethanol 65:35+0.1% triethylamine) and isolation of the isomer as the first eluting peak.

ESI-MS [M+H$^+$]=442 Calculated for $C_{24}H_{31}N_3O_3S$=441.

Example 25

Cis-N-(1-(4-benzyl-3-(methylamino)chroman-6-yl)azetidin-3-yl)-1-cyclopropylmethanesulfonamide—Isomer 2

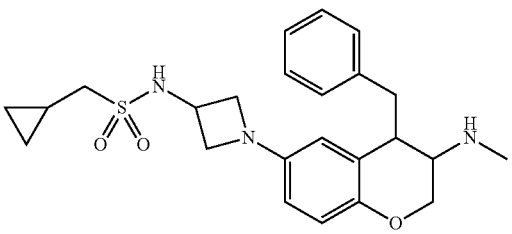 [SMILES: CNC1COc2ccc(N3CC(NS(=O)(=O)CC4CC4)C3)cc2C1Cc1ccccc1]

Cis-N-(1-(4-benzyl-3-(methylamino)chroman-6-yl)azetidin-3-yl)-1-cyclopropylmethanesulfonamide was prepared by separation of the racemic mixture obtained in example 13 through chiral chromatography on Daicel Chiralpak (n-heptane ethanol 65:35+0.1% triethylamine) and isolation of the isomer as the second eluting peak.

ESI-MS [M+H$^+$]=442 Calculated for $C_{24}H_{31}N_3O_3S$=441.

Example 26

Cis-1-(4-benzyl-7-fluoro-6-(3-(5-fluoropyridine-3-sulfonamido)azetidin-1-yl)chroman-3-yl)azetidin-1-ium (E)-3-carboxyacrylate

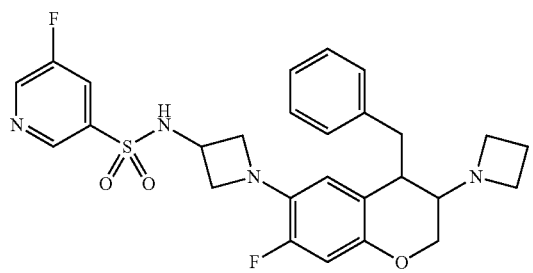 [SMILES: O=S(=O)(NC1CN(c2cc3c(cc2F)OCC(N2CCC2)C3Cc2ccccc2)C1)c1cncc(F)c1]

Cis-1-(4-benzyl-7-fluoro-6-(3-(5-fluoropyridine-3-sulfonamido)azetidin-1-yl)chroman-3-yl)azetidin-1-ium (E)-3-carboxyacrylate was prepared in analogy to example 1.

ESI-MS [M+H$^+$]=527 Calculated for C$_{27}$H$_{28}$F$_2$N$_4$O$_3$S=526.

Example 27

Cis-N-(1-(4-benzyl-7-fluoro-3-(methylamino)chroman-6-yl)azetidin-3-yl)propane-1-sulfonamide—Isomer 1

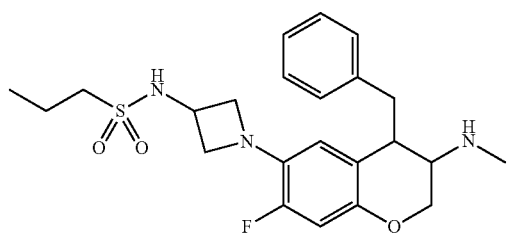 [SMILES: CCCS(=O)(=O)NC1CN(c2cc3c(cc2F)OCC(NC)C3Cc2ccccc2)C1]

Cis-N-(1-(4-benzyl-7-fluoro-3-(methylamino)chroman-6-yl)azetidin-3-yl)propane-1-sulfonamide was prepared by separation of the racemic mixture obtained in example 16 through chiral chromatography on Daicel Chiralpak (n-heptane ethanol 70:30+0.1% triethylamine) and isolation of the isomer as the first eluting peak.

ESI-MS [M+H$^+$]=448 Calculated for C$_{23}$H$_{30}$FN$_3$O$_3$S=429.

Example 28

Cis-N-(1-(4-benzyl-7-fluoro-3-(methylamino)chroman-6-yl)azetidin-3-yl)propane-1-sulfonamide—Isomer 2

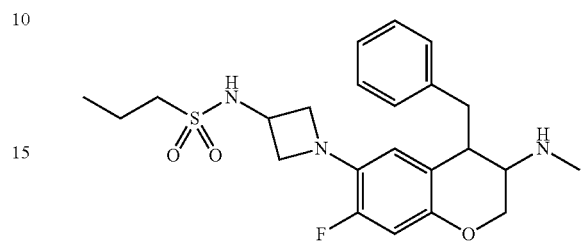

Cis-N-(1-(4-benzyl-7-fluoro-3-(methylamino)chroman-6-yl)azetidin-3-yl)propane-1-sulfonamide was prepared by separation of the racemic mixture obtained in example 11 through chiral chromatography on Daicel Chiralpak (n-heptane ethanol 65:35+0.1% triethylamine) and isolation of the isomer as the second eluting peak.

ESI-MS [M+H$^+$]=448 Calculated for C$_{23}$H$_{30}$FN$_3$O$_3$S=429.

Example 29

Cis-N-(1-(4-benzyl-3-(propylamino)chroman-6-yl)azetidin-3-yl)propane-1-sulfonamide

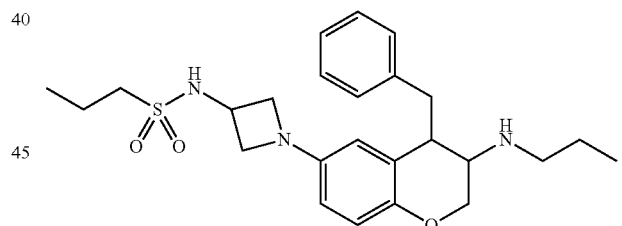

0.17 g (0.41 mmol) of cis-N-(1-(3-amino-4-benzylchroman-6-yl)azetidin-3-yl)propane-1-sulfonamide was reacted with 0.03 mL (0.41 mmol) propionaldehyde in the presence of 0.02 mL (0.41 mol) glacial acetic acid in 20 mL dichloro ethylene. 0.03 g (0.51 mmol) sodiumcyanoborohydride were dissolved in 5 mL methanol, added, and the mixture was stirred at room temperature for 30 min. The reaction mixture was added to aqueous sodium bicarbonate solution and stirred for 15 min., then it was extracted three times with dichloro methylene. The combined organic phases were dried with MgSO$_4$ and evaporated to dryness. The residue was purified by flash chromatography to yield 0.09 g (0.19 mmol, 47%) of the desired product.

ESI-MS [M+H$^+$]=458 Calculated for C$_{25}$H$_{35}$N$_3$O$_3$S=457.

Example 30

Cis-N-(1-(4-benzyl-3-(diethylamino)chroman-6-yl)azetidin-3-yl)propane-1-sulfonamide

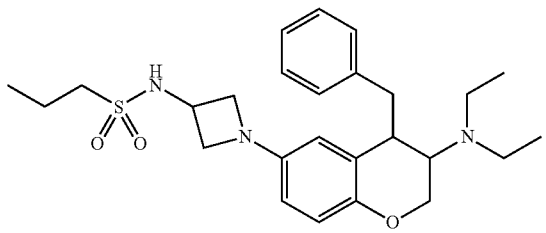 [SMILES: CCCS(=O)(=O)NC1CN(c2ccc3c(c2)C(Cc2ccccc2)C(N(CC)CC)CO3)C1]

Cis-N-(1-(4-benzyl-3-(diethylamino)chroman-6-yl)azetidin-3-yl)propane-1-sulfonamide was prepared in analogy to example 29.

ESI-MS [M+H$^+$]=472 Calculated for $C_{26}H_{37}N_3O_3S$=471.

Example 31

Cis-N-(1-(4-benzyl-3-((cyclopropylmethyl)amino)chroman-6-yl)azetidin-3-yl)propane-1-sulfonamide

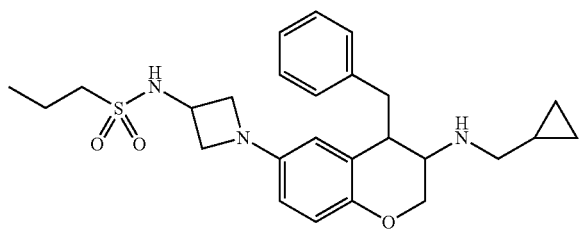 [SMILES: CCCS(=O)(=O)NC1CN(c2ccc3c(c2)C(Cc2ccccc2)C(NCC2CC2)CO3)C1]

Cis-N-(1-(4-benzyl-3-((cyclopropylmethyl)amino)chroman-6-yl)azetidin-3-yl)propane-1-sulfonamide was prepared in analogy to example 29.

ESI-MS [M+H$^+$]=470 Calculated for $C_{26}H_{35}N_3O_3S$=469.

Example 32

Cis-N-(1-(4-benzyl-3-(cyclobutylamino)chroman-6-yl)azetidin-3-yl)propane-1-sulfonamide

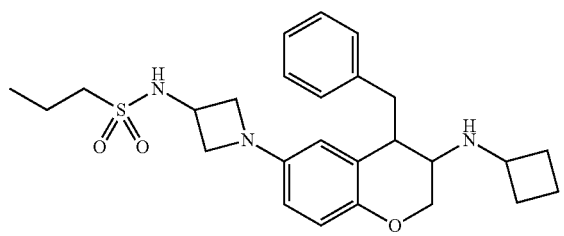 [SMILES: CCCS(=O)(=O)NC1CN(c2ccc3c(c2)C(Cc2ccccc2)C(NC2CCC2)CO3)C1]

Cis-N-(1-(4-benzyl-3-(cyclobutylamino)chroman-6-yl)azetidin-3-yl)propane-1-sulfonamide was prepared in analogy to example 29.

ESI-MS [M+H$^+$]=470 Calculated for $C_{26}H_{35}N_3O_3S$=469.

BIOLOGICAL TESTING

1. [$^3$H]-Glycine uptake into recombinant CHO cells expressing human GlyT1: Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 μl HBSS (Gibco BRL, #14025-050) with 5 mM L-Alanine (Merck #1007). 80 μl HBSS buffer were added, followed by 10 μl inhibitor or vehicle (10% DMSO) and 10 μl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 μM Org24598. IC$_{50}$ calculations were made by four-parametric logistic nonlinear regression analysis (GraphPad Prism) using determinations within the range of linear increase of [$^3$H]-glycine incorporation between 60 and 120 min.

2. Radioligand binding assays using recombinant CHO cell membranes expressing human GlyT1:

Radioligand binding to human GlyT1c transporter-expressing membranes was determined as described in Mezler et al., Molecular Pharmacology 74:1705-1715, 2008.

The following results were obtained with the compounds disclosed in the examples:

TABLE 1

| Example | radioligand binding $K_{iapp}$ [μM] |
|---------|-------------------------------------|
| 1       | ≤0.01                               |
| 2*      | ≤1.0                                |
| 3       | ≤0.1                                |
| 4       | ≤0.1                                |
| 5       | ≤0.1                                |
| 6       | ≤0.01                               |
| 7*      | ≤0.1                                |
| 8*      | ≤1.0                                |
| 9       | ≤1.0                                |
| 10      | ≤0.1                                |
| 11      | ≤0.01                               |
| 12      | ≤0.1                                |
| 13      | ≤0.01                               |
| 14a     | ≤0.1                                |
| 14b     | ≤0.1                                |
| 15a     | ≤0.01                               |
| 15b     | ≤0.01                               |
| 16a     | ≤0.01                               |
| 16b     | ≤0.01                               |
| 17a     | ≤0.01                               |
| 17b     | ≤0.01                               |
| 18a     | ≤0.01                               |
| 18b     | ≤0.01                               |
| 19a     | ≤0.01                               |
| 19b     | ≤0.01                               |
| 20*     | ≤0.1                                |
| 21*     | ≤0.01                               |
| 22*     | ≤0.01                               |
| 23*     | ≤1.0                                |
| 24      | ≤0.01                               |
| 25*     | ≤1.0                                |
| 26*     | ≤0.1                                |
| 27      | ≤0.01                               |
| 28      | ≤0.1                                |
| 29      | ≤0.1                                |
| 30      | ≤0.1                                |
| 31      | ≤1.0                                |
| 32      | ≤1.0                                |

*these compounds were tested in the form of the corresponding fumarate salts

3. Metabolic stability

Metabolic stability was determined as follows:

0.5 µM test substance was preincubated together with human liver microsomes (0.25 mg of microsomal protein/ ml) in 0.05 M potassium phosphate buffer of pH 7.4 in microtiter plates at 37° C. for 5 min. The reaction was started by adding NADPH (1.0 mM). After 0, 5, 10, 15, 20 and 30 min the reaction was stopped and cooled with twice the amount of quench solution consisting of acetonitrile/methanol 1:1, and containing 0.2 µM carbutamide. The samples were frozen until analyzed. The remaining concentration of undegraded test substance was determined by LC MSMS. The half-life (T1/2) was determined from the gradient of the signal of test substance/unit time plot, al-lowing to calculate the half-life of the test substance, assuming first order kinetics, from the de-crease in the concentration of the compound with time. The microsomal clearance (mClint) was calculated as follows: mClint=((ln(2)/t1/2)/Microsomal Protein Concentration (mg/ml))*1000, leading to the unit of uL/min/mg. The scaled clearance (mClin_scaled) was calculated as mCLint_scaled=m CLint*(Microsomal Yield (mg/kg BW))/1000000*60, leading to the units L/hr/kg. The Microsomal Yield is defined by the specifics of the used microsomes. Calculations were modified from references: Di, The Society for Biomolecular Screening, 2003, 453-462; Obach, DMD, 1999 vol 27. N 11, 1350-1359.

The following results were obtained with the compounds disclosed in the examples:

TABLE 2

| Example | human mCl [L/h/Kg] |
|---|---|
| 1 | ≤5 |
| 2* | ≤5 |
| 3 | ≤5 |
| 4 | ≤5 |
| 5 | ≤5 |
| 6 | ≤5 |
| 7* | ND |
| 8* | ≤50 |
| 9 | ≤50 |
| 10 | ≤5 |
| 11 | ≤5 |
| 12 | ≤5 |
| 13 | ≤5 |
| 14a | ≤5 |
| 14b | ≤5 |
| 15a | ≤5 |
| 15b | ≤5 |
| 16a | ≤5 |
| 16b | ≤5 |
| 17a | ≤5 |
| 17b | ≤5 |
| 18a | ≤50 |
| 18b | ≤5 |
| 19a | ≤50 |
| 19b | ≤50 |
| 20* | ND |
| 21* | ≤5 |
| 22* | ≤5 |
| 23* | ≤50 |
| 24 | ≤50 |
| 25* | ≤5 |
| 26* | ≤50 |
| 27 | ≤50 |
| 28 | ≤5 |
| 29 | ≤5 |
| 30 | ≤50 |
| 31 | ≤5 |
| 32 | ≤5 |

*these compounds were tested in the form of the corresponding fumarate salts

4. Determination of efflux ratio using Madin-Darby Canine Kidney Type II cells

Bidirectional transport experiments were performed on Madin-Darby Canine Kidney Type II cells over-expressing multidrug resistance protein 1 (MDR1-MDCK) to evaluate the compounds as potential P-gp substrates.

Compounds were added at 1 µM in HBSS-pH 7.4 (hanks balanced salt solution) to either the apical or basolateral side of MDR1-MDCK cell monolayers grown on Millicell 96-Cell polycarbonate filters. Samples were collected from both apical and basolateral sides at time 0 and after 1 h incubation at 37 C, compounds concentrations were measured by HPLC/MS/MS and permeability coefficients were then determined in both transport directions. The efflux ratio was subsequently calculated from the permeability coefficient.

For reasons of completeness, various aspects of the present disclosure are set out in the following numbered clauses:

Clause 1. Compounds of the formula (I)

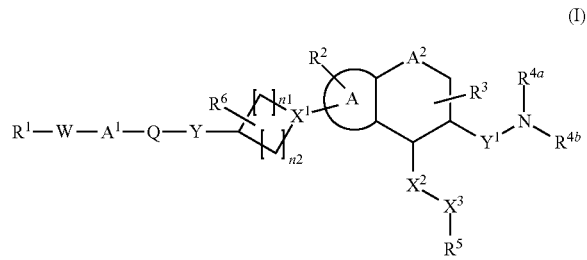

wherein

A is a 5- or 6-membered ring;

$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $M_3$-$M_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $M_3$-$M_{12}$-heterocyclylsulfonylamino-$C_1$-$C_4$-alkoxy, $M_3$-$M_{12}$-heterocyclyl-$C_1$-$C_4$-alkoxy, $C_6$-$C_{12}$-aryloxy, $M_3$-$M_{12}$-heterocyclyloxy, $C_1$-$C_6$-alkylthio, halogenated $C_1$-$C_6$- alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $M_3$-$M_{12}$-heterocyclyl;

W is —$NR^7$— or a bond;
$A^1$ is optionally substituted $C_1$-$C_4$-alkylene or a bond;
Q is —$S(O)_2$— or —$C(O)$—;
Y is —$NR^8$— or a bond;
n1 is 0, 1, 2, or 3;
n2 is 0, 1, 2, or 3;
$X^1$ is >N— or >CH—;
$R^6$ is hydrogen, halogen, $C_1$-$C_4$-alkyl, halogenated $C_1$-$C_4$-alkyl, —CN, OH $C_1$-$C_6$-alkoxy or halogenated $C_1$-$C_6$-alkoxy, or two radicals $R^6$ together with the carbon atom to which they are attached form a carbonyl group;
$R^2$ is hydrogen, halogen, $C_1$-$C_6$-alkyl, halogenated $C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $M_3$-$M_{12}$-heterocyclyl, or two radicals $R^2$ together with the ring atoms of A to which they are bound form a 5- or 6 membered ring;
$A^2$ is —O—, —S— or —$NR^9$—;
$R^3$ is hydrogen, halogen, $C_1$-$C_6$-alkyl or $C_1$-$C_6$-alkoxy, or two radicals $R^3$ together with the carbon atom to which they are attached form a carbonyl group;
$Y^1$ is a bond or optionally substituted $C_1$-$C_4$-alkylene;
$R^{4a}$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, —$CH_2CN$, $C_6$-$C_{12}$-aryl-$C_1$-$C_4$-alkyl, optionally substituted $C_3$-$C_{12}$-cycloalkyl, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino, —NO or optionally substituted $M_3$-$M_{12}$-heterocyclyl; or
$R^{4a}$ is optionally substituted $C_1$-$C_4$-alkylene that is bound to a carbon atom in $Y^1$;
$R^{4b}$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, —$CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino, —NO or $M_3$-$M_{12}$-heterocyclyl; or
$R^{4a}$, $R^{4b}$
together are optionally substituted $C_2$-$C_6$-alkylene, wherein one —$CH_2$— of $C_2$-$C_6$-alkylene may be replaced by an oxygen atom or —$NR^{10}$;
$X^2$ is —O—, —$NR^{11a}$—, >$CR^{12a}R^{12b}$ or a bond;
$X^3$ is —O—, —$NR^{11b}$—, —S—, >$CR^{13a}R^{13b}$ or a bond;
$R^5$ is optionally substituted $C_6$-$C_{12}$-aryl, optionally substituted $C_3$-$C_{12}$-cycloalkyl or optionally substituted $M_3$-$M_{12}$-heterocyclyl;
$R^7$ is hydrogen or $C_1$-$C_6$-alkyl;

$R^8$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl or $M_3$-$M_{12}$-heterocyclyl; or
$R^8$, $R^1$
together are $C_1$-$C_4$-alkylene;
$R^9$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, $C_6$-$C_{12}$-aryl-$C_1$-$C_4$-alkyl, $C_3$-$C_{12}$-cycloalkyl, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)$NH_2$, —C(=NH)NHCN, $C_1$-$C_6$-alkylsulfonyl, $C_6$-$C_{12}$-arylsulfonyl, amino, —NO or $M_3$-$M_{12}$-heterocyclyl;
$R^{10}$ is hydrogen or $C_1$-$C_6$-alkyl;
$R^{11a}$ is hydrogen or $C_1$-$C_6$-alkyl;
$R^{11b}$ is hydrogen or $C_1$-$C_6$-alkyl;
$R^{12a}$ is hydrogen, optionally substituted $C_1$-$C_6$-alkyl, $C_1$-$C_6$-alkylamino-$C_1$-$C_4$-alkyl, di-$C_1$-$C_6$ alkylamino $C_1$-$C_4$ alkyl, $M_3$-$M_{12}$-heterocyclyl-$C_1$-$C_6$-alkyl, optionally substituted $C_6$-$C_{12}$-aryl or hydroxy;
$R^{12b}$ is hydrogen or $C_1$-$C_6$-alkyl, or
$R^{12a}$, $R^{12b}$
together with the carbon atom to which they are attached form a carbonyl or are optionally substituted $C_2$-$C_4$-alkylene, wherein one —$CH_2$— of $C_2$-$C_4$-alkylene may be replaced by an oxygen atom or —$NR^{14}$—;
$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $M_3$-$M_{12}$-heterocyclyl-$C_1$-$C_6$-alkyl, optionally substituted $C_6$-$C_{12}$-aryl or hydroxy;
$R^{13b}$ is hydrogen or $C_1$-$C_6$-alkyl, or
$R^{13a}$, $R^{13b}$
together with the carbon atom to which they are attached form a carbonyl or are optionally substituted $C_2$-$C_4$-alkylene, wherein one —$CH_2$— of $C_2$-$C_4$-alkylene may be replaced by an oxygen atom or —$NR^{15}$—;
$R^{14}$ is hydrogen or $C_1$-$C_6$-alkyl; and
$R^{15}$ is hydrogen or $C_1$-$C_6$-alkyl,
or a physiologically tolerated salt thereof Clause 2. Compound as claimed in clause 1, wherein A is a benzene ring or a ring selected from the group consisting of the following 5- or 6-membered heterocyclic rings:

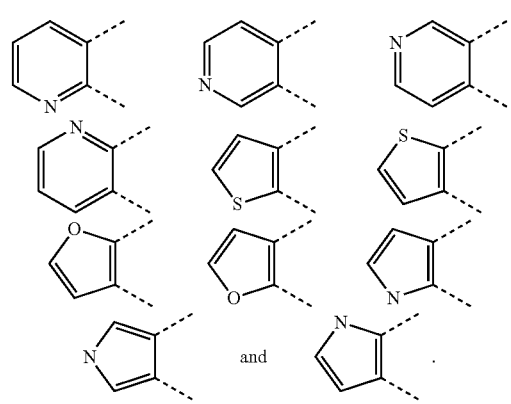

Clause 3. Compound as claimed in clause 1 or 2, wherein $R^1$ is $C_1$-$C_6$-alkyl, $C_3$-$C_{12}$-cycloalkyl-$C_1$-$C_4$-alkyl, or $C_3$-$C_{12}$-cycloalkyl.

Clause 4. Compound as claimed in any one of clauses 1 to 3, wherein W is a bond and $A^1$ is a bond.

Clause 5. Compound as claimed in any one of clauses 1 to 4, wherein Q is —S(O)$_2$—.

Clause 6. Compound as claimed in any one of clauses 1 to 5, wherein Y is —NR$^8$—.

Clause 7. Compound as claimed in any one of clauses 1 to 6, wherein at least one of n1 and n2 is 1, 2, or 3.

Clause 8. Compound as claimed in any one of clauses 1 to 7, wherein the sum of n1+n2 is 2, 3, or 4.

Clause 9. Compound as claimed in any one of clauses 1 to 6, wherein $X^1$ is >N—, n1 is 1, and n2 is 1; or $X^1$ is >CH—, n1 is 1, and n2 is 1.

Clause 10. Compound as claimed in any one of clauses 1 to 9, wherein $R^6$ is hydrogen or $C_1$-$C_4$-alkyl, or two radicals $R^6$ together with the carbon atom to which they are attached form a carbonyl group.

Clause 11. Compound as claimed in any one of clauses 1 to 10, having the formula

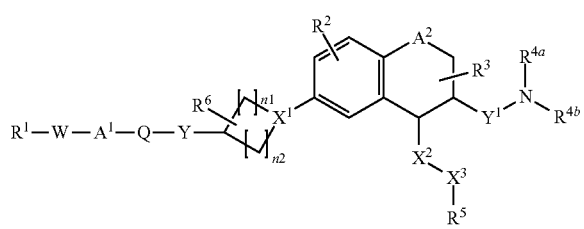

wherein $R^1$, W, $A^1$, Q, Y, n1, n2, $X^1$, $R^6$, $R^2$, $A^2$, $R^3$, $Y^1$, $R^{4a}$, $R^{4b}$, $X^2$, $X^3$, $R^5$ are as defined in any one of clauses 1 to 10.

Clause 12. Compound as claimed in any one of clauses 1 to 11, wherein $R^2$ is hydrogen or halogen.

Clause 13. Compound as claimed in clause 11 or 12, having one of the formulae

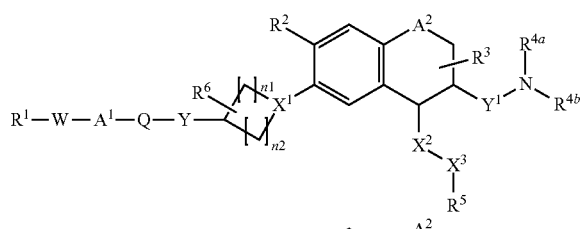

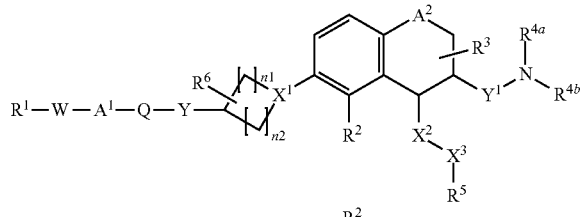

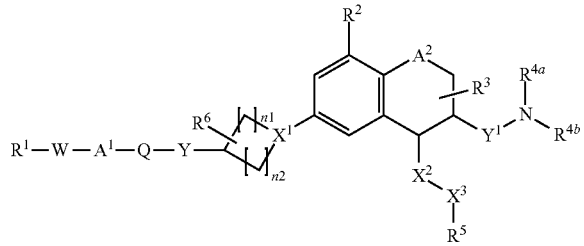

wherein $R^1$, W, $A^1$, Q, Y, n1, n2, $X^1$, $R^6$, $R^2$, $A^2$, $R^3$, $Y^1$, $R^{4a}$, $R^{4b}$, $X^2$, $X^3$, $R^5$ are as defined in any one of clauses 1 to 12.

Clause 14. Compound as claimed in any one of clauses 1 to 13, wherein $A^2$ is —O—.

Clause 15. Compound as claimed in any one of clauses 1 to 14, wherein $R^3$ is hydrogen or $C_1$-$C_6$-alkyl.

Clause 16. Compound as claimed in any one of clauses 1 to 15, having the formula

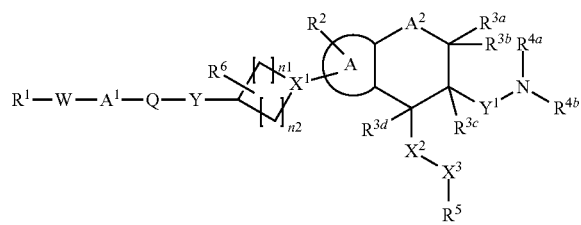

wherein $R^{3a}$, $R^{3b}$, $R^{4c}$, $R^{3d}$ independently have the meaning of $R^3$, and A, $R^1$, W, $A^1$, Q, Y, n1, n2, $X^1$, $R^6$, $R^2$, $A^2$, $R^3$, $Y^1$, $R^{4a}$, $R^{4b}$, $X^2$, $X^3$, $R^5$ are as defined in any one of clauses 1 to 15.

Clause 17. Compound as claimed in clauses 1 to 16, wherein $Y^1$ is a bond.

Clause 18. Compound as claimed in clauses 1 to 17, wherein $R^{4a}$ is hydrogen, $C_1$-$C_6$-alkyl, optionally substituted $C_3$-$C_{12}$-cycloalkyl, $C_3$-$C_{12}$-cycloalkyl-$C_1$-$C_4$-alkyl, or $M_3$-$M_{12}$-heterocyclyl.

Clause 19. Compound as claimed in any one of clauses 1 to 18, wherein $R^{4b}$ is hydrogen or $C_1$-$C_6$-alkyl.

Clause 20. Compound as claimed in any one of clauses 1 to 17, wherein $R^{4a}$, $R^{4b}$ together are optionally substituted $C_2$-$C_6$-alkylene, wherein one —CH$_2$— of $C_2$-$C_6$-alkylene may be replaced by an oxygen atom.

Clause 21. Compound as claimed in any one of clauses 1 to 20, wherein $X^2$ is >CR$^{12a}$R$^{12b}$.

Clause 22. Compound as claimed in any one of clause 1 to 21, wherein $X^3$ is a bond.

Clause 23. Compound as claimed in any one of clauses 1 to 22, wherein $R^{12a}$ is hydrogen or $C_1$-$C_6$-alkyl and $R^{12b}$ is hydrogen or $C_1$-$C_6$-alkyl.

Clause 24. Compound as claimed in any one of clauses 1 to 23, wherein $R^5$ is optionally substituted aryl.

Clause 25. Compound as claimed in clause 24, having the formula

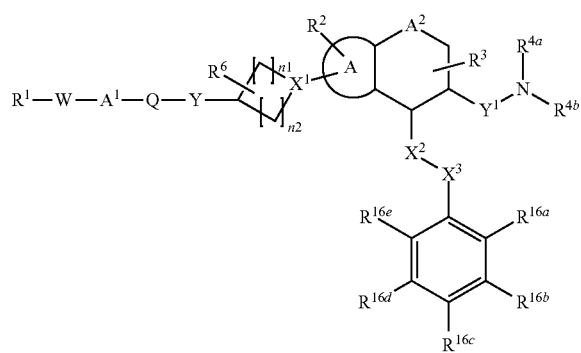

wherein A, $R^1$, W, $A^1$, Q, Y, n1, n2, $X^1$, $R^6$, $R^2$, $R^3$, $A^2$, $Y^1$, $R^{4a}$, $R^{4b}$, $X^2$, $X^3$ are as defined in any one of clauses 1 to 23; and $R^{16a}$, $R^{16b}$, $R^{16c}$, $R^{16d}$, $R^{16e}$ independently are hydrogen, halogen, or halogenated $C_1$-$C_6$-alkyl.

Clause 26. Compound as claimed in any one of clauses 1 to 25, wherein $R^8$ is hydrogen.

Clause 27. Compound as claimed in clause 1, wherein
A is a benzene ring;
$R^1$ is $C_1$-$C_6$-alkyl, $C_3$-$C_{12}$-cycloalkyl-$C_1$-$C_4$-alkyl, or an optionally substituted $M_3$-$M_{12}$-heterocyclyl;
W is a bond;
$A^1$ is a bond;
Q is —S(O)$_2$—;
Y is —NR$^8$—;
n1 is 1;
n2 is 1;
$R^6$ is hydrogen;
$X^1$ is ->N— or >CH—;
$R^2$ is hydrogen or halogen;
$A^2$ is —O—;
$R^3$ is hydrogen;
$Y^1$ is a bond;
$R^{4a}$ is hydrogen, $C_1$-$C_6$-alkyl, $C_3$-$C_{12}$-cycloalkyl-$C_1$-$C_4$-alkyl, or $C_3$-$C_{12}$-cycloalkyl;
$R^{4b}$ is hydrogen or $C_1$-$C_6$-alkyl; or
$R^{4a}$, $R^{4b}$
 together are $C_2$-$C_6$-alkylene;
$X^2$ is >CR$^{12a}$R$^{12b}$;
$X^3$ is a bond;
$R^5$ is optionally substituted phenyl;
$R^8$ is hydrogen;
$R^{12a}$ is hydrogen; and
$R^{12b}$ is hydrogen.

Clause 28. The compound as claimed in clause 1 which is:
N-[1-[3-(azetidin-1-yl)-4-benzyl-chroman-6-yl]azetidin-3-yl]-1-methyl-imidazole-4-sulfonamide;
Cis-N-(1-(3-(azetidin-1-yl)-4-benzylchroman-6-yl)azetidin-3-yl)ethanesulfonamide;
Cis-N-(1-(3-(azetidin-1-yl)-4-benzylchroman-6-yl)azetidin-3-yl)propane-1-sulfonamide;
Cis-N-(1-(3-(azetidin-1-yl)-4-benzylchroman-6-yl)azetidin-3-yl)-1-cyclopropylmethane sulfonamide;
Cis-N-(1-(3-(azetidin-1-yl)-4-benzylchroman-6-yl)azetidin-3-yl)-1-methyl-1H-pyrazole-4-sulfonamide;
Cis-N-(1-(3-(azetidin-1-yl)-4-benzylchroman-6-yl)azetidin-3-yl)-1-methyl-1H-1,2,3-triazole-4-sulfonamide;
Cis-N-(1-(3-(azetidin-1-yl)-4-benzyl-7-fluorochroman-6-yl)azetidin-3-yl)-1-ethyl-1H-1,2,3-triazole-4-sulfonamide;
Cis-N-(1-(3-(azetidin-1-yl)-4-benzyl-7-fluorochroman-6-yl)azetidin-3-yl)-2-fluoropyridine-3-sulfonamide;
Cis-N-(1-(3-(azetidin-1-yl)-4-benzyl-7-fluorochroman-6-yl)azetidin-3-yl)pyridazine-3-sulfonamide;
Cis-N-(1-(3-(azetidin-1-yl)-4-benzylchroman-6-yl)azetidin-3-yl)-2-fluoropyridine-3-sulfonamide;
Cis-N-(1-(4-benzyl-3-(methylamino)chroman-6-yl)azetidin-3-yl)propane-1-sulfonamide;
Cis-N-(1-(-4-benzyl-3-(methylamino)chroman-6-yl)azetidin-3-yl)ethanesulfonamide;
Cis-N-(1-(4-benzyl-3-(methylamino)chroman-6-yl)azetidin-3-yl)-1-cyclopropylmethane sulfonamide;
Cis-N-(1-(4-benzyl-7-fluoro-3-(methylamino)chroman-6-yl)azetidin-3-yl)ethanesulfonamide;
Trans-N-(1-(4-benzyl-7-fluoro-3-(methylamino)chroman-6-yl)azetidin-3-yl)ethanesulfonamide;
Cis-N-(1-(4-benzyl-7-fluoro-3-(methylamino)chroman-6-yl)azetidin-3-yl)-1-methyl-1H-imidazole-4-sulfonamide;
Trans-N-(1-(4-benzyl-7-fluoro-3-(methylamino)chroman-6-yl)azetidin-3-yl)-1-methyl-1H-imidazole-4-sulfonamide;
Cis-N-(1-(4-benzyl-7-fluoro-3-(methylamino)chroman-6-yl)azetidin-3-yl)propane-1-sulfonamide;
Trans-N-(1-(4-benzyl-7-fluoro-3-(methylamino)chroman-6-yl)azetidin-3-yl)propane-1-sulfonamide;
Cis-N-(1-(4-benzyl-7-fluoro-3-(methylamino)chroman-6-yl)azetidin-3-yl)-1-methyl-1H-pyrazole-4-sulfonamide;
Trans-N-(1-(4-benzyl-7-fluoro-3-(methylamino)chroman-6-yl)azetidin-3-yl)-1-methyl-1H-pyrazole-4-sulfonamide;
Cis-N-(1-(4-benzyl-7-fluoro-3-(methylamino)chroman-6-yl)azetidin-3-yl)-1-methyl-1H-1,2,3-triazole-4-sulfonamide;
Trans-N-(1-(4-benzyl-7-fluoro-3-(methylamino)chroman-6-yl)azetidin-3-yl)-1-methyl-1H-1,2,3-triazole-4-sulfonamide;
Cis-N-(1-(4-benzyl-7-fluoro-3-(methylamino)chroman-6-yl)azetidin-3-yl)-1-cyclopropylmethanesulfonamide;
Trans-N-(1-(4-benzyl-7-fluoro-3-(methylamino)chroman-6-yl)azetidin-3-yl)-1-cyclopropylmethanesulfonamide;
Cis-N-(1-(3-amino-4-benzylchroman-6-yl)azetidin-3-yl)propane-1-sulfonamide;
Cis-N-(1-(3-amino-4-benzylchroman-6-yl)azetidin-3-yl)-1-cyclopropylmethanesulfonamide;
Cis-1-(4-benzyl-7-fluoro-6-(3-(5-fluoropyridine-3-sulfonamido)azetidin-1-yl)chroman-3-yl)azetidin-1-ium (E)-3-carboxyacrylate;
Cis-N-(1-(4-benzyl-3-(propylamino)chroman-6-yl)azetidin-3-yl)propane-1-sulfonamide;
Cis-N-(1-(4-benzyl-3-(diethylamino)chroman-6-yl)azetidin-3-yl)propane-1-sulfonamide;
Cis-N-(1-(4-benzyl-3-((cyclopropylmethyl)amino)chroman-6-yl)azetidin-3-yl)propane-1-sulfonamide; and
Cis-N-(1-(4-benzyl-3-(cyclobutylamino)chroman-6-yl)azetidin-3-yl)propane-1-sulfonamide, or a physiologically tolerated salt thereof Clause 29. The compound as claimed in any one of clauses 1 to 28 for use in therapy.

Clause 30. Pharmaceutical composition which comprises a carrier and a compound of any one of clauses 1 to 28.

Clause 31. A method for inhibiting the glycine transporter GlyT1 in a mammal in need thereof which comprises the administration of an effective amount of a compound of any one of clauses 1 to 28.

Clause 32. The use of a compound of any one of clauses 1 to 28 in the manufacture of a medicament for inhibiting the glycine transporter GlyT1.

Clause 33. A method for treating a neurologic or psychiatric disorder or pain in a mammalian patient in need thereof which comprises administering to the patient a therapeutically effective amount of a compound of any one of clauses 1 to 28.

Clause 34. The use of a compound of any one of clauses 1 to 28 in the manufacture of a medicament for treating a neurologic or psychiatric disorder or pain.

Clause 35. The compound of any one of clauses 1 to 28 for use in a method of treating a neurologic or psychiatric disorder or pain.

Clause 36. The method, use or compound as claimed in any one of clauses 30 to 35, wherein the disorder is associated with glycinergic or glutamatergic neurotransmission dysfunction.

Clause 37. The method, use or compound as claimed in any one of clauses 30 to 36, wherein the neurologic disorder is a cognitive disorder such as dementia, cognitive impairment, or attention deficit disorder.

Clause 38. The method, use or compound as claimed in clause 37, wherein the attention deficit disorder is an attention deficit disorder with hyperactivity.

Clause 39. The method, use or compound as claimed in any one of any one of clauses 30 to 35, wherein the psychiatric disorder is an anxiety disorder, a mood disorder such as depression, a bipolar disorder, schizophrenia, or a psychotic disorder.

We claim:
1. A compound of the formula (I)

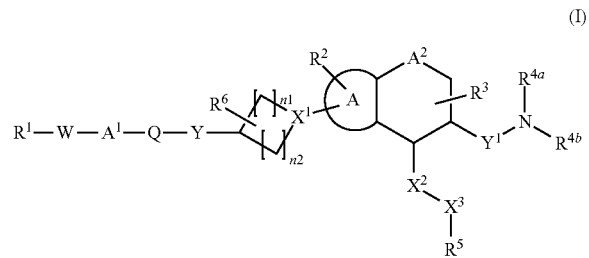

wherein
A is selected from the group consisting of:

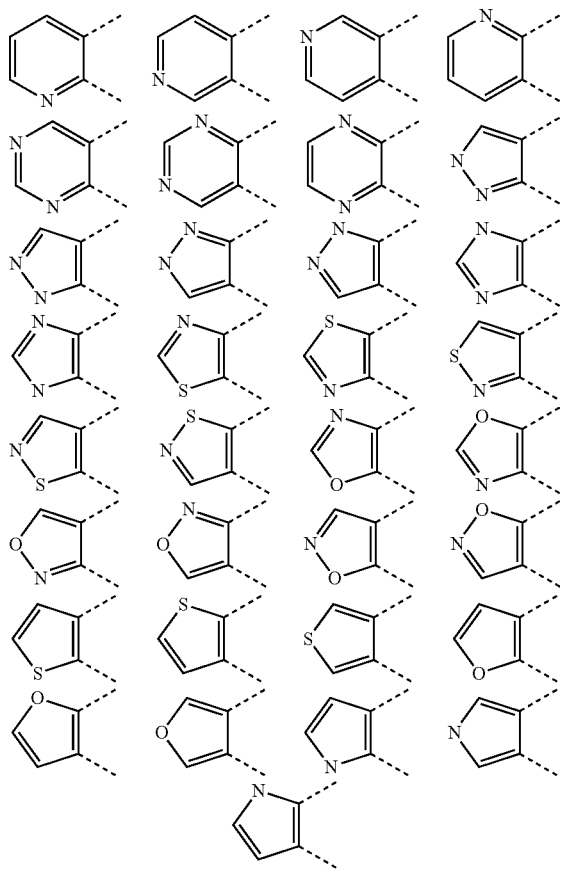

and a benzene ring;
$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $M_3$-$M_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $M_3$-$M_{12}$-heterocyclylsulfonylamino-$C_1$-$C_4$-alkoxy, $M_3$-$M_{12}$-heterocyclyl-$C_1$-$C_4$-alkoxy, $C_6$-$C_{12}$-aryloxy, $M_3$-$M_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $M_3$-$M_{12}$-heterocyclyl;
W is —$NR^7$— or a bond;
$A^1$ is optionally substituted $C_1$-$C_4$-alkylene or a bond;
Q is —$S(O)_2$— or —$C(O)$—;
Y is —$NR^8$— or a bond;
n1 is 0, 1, 2, or 3;
n2 is 0, 1, 2, or 3;
$X^1$ is >N— or >CH—;
$R^6$ is hydrogen, halogen, $C_1$-$C_4$-alkyl, halogenated $C_1$-$C_4$-alkyl, —CN, OH $C_1$-$C_6$-alkoxy or halogenated $C_1$-$C_6$-alkoxy, or two radicals $R^6$ together with the carbon atom to which they are attached form a carbonyl group;
$R^2$ is hydrogen, halogen, $C_1$-$C_6$-alkyl, halogenated $C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $M_3$-$M_{12}$-heterocyclyl, or two radicals $R^2$ together with the ring atoms of A to which they are bound form a 5- or 6 membered ring;
$A^2$ is —O—;
$R^3$ is hydrogen, halogen, $C_1$-$C_6$-alkyl or $C_1$-$C_6$-alkoxy, or two radicals $R^3$ together with the carbon atom to which they are attached form a carbonyl group;
$Y^1$ is a bond or optionally substituted $C_1$-$C_4$-alkylene;
$R^{4a}$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, —$CH_2CN$, $C_6$-$C_{12}$-aryl-$C_1$-$C_4$-alkyl, optionally substituted C$_3$-C$_{12}$-cycloalkyl, —CHO, C$_1$-C$_4$-alkylcarbonyl, (halogenated C$_1$-C$_4$-alkyl)carbonyl, C$_6$-C$_{12}$-arylcarbonyl, C$_1$-C$_4$-alkoxycarbonyl, C$_6$-C$_{12}$-aryloxycarbonyl, C$_1$-C$_6$-alkylaminocarbonyl, C$_2$-C$_6$-alkenyl, —C(=NH)NH$_2$, —C(=NH)NHCN, C$_1$-C$_6$-alkylsulfonyl, C$_6$-C$_{12}$-arylsulfonyl, amino, —NO or optionally substituted M$_3$-M$_{12}$-heterocyclyl; or R$^{4b}$ is hydrogen, C$_1$-C$_6$-alkyl, halogenated C$_1$-C$_4$-alkyl, hydroxy-C$_1$-C$_4$-alkyl, C$_1$-C$_6$-alkoxy-C$_1$-C$_4$-alkyl, amino-C$_1$-C$_4$-alkyl, —CH$_2$CN, —CHO, C$_1$-C$_4$-alkylcarbonyl, (halogenated C$_1$-C$_4$-alkyl)carbonyl, C$_6$-C$_{12}$-arylcarbonyl, C$_1$-C$_4$-alkoxycarbonyl, C$_6$-C$_{12}$-aryloxycarbonyl, C$_1$-C$_6$-alkylaminocarbonyl, C$_2$-C$_6$-alkenyl, —C(=NH)NH$_2$, —C(=NH)NHCN, C$_1$-C$_6$-alkylsulfonyl, C$_6$-C$_{12}$-arylsulfonyl, amino, —NO or M$_3$-M$_{12}$-heterocyclyl; or R$^{4a}$, R$^{4b}$
together are optionally substituted C$_2$-C$_6$-alkylene, wherein one —CH$_2$— of C$_2$-C$_6$-alkylene may be replaced by an oxygen atom or —NR$^{10}$;

X$^2$ is —O—, —NR$^{11a}$—, —S—, >CR$^{12a}$R$^{12b}$ or a bond;
X$^3$ is —O—, —NR$^{11b}$—, —S—, >CR$^{13a}$R$^{13b}$ or a bond;
R$^5$ is optionally substituted C$_6$-C$_{12}$-aryl, optionally substituted C$_3$-C$_{12}$-cycloalkyl or optionally substituted M$_3$-M$_{12}$-heterocyclyl;
R$^7$ is hydrogen or C$_1$-C$_6$-alkyl;
R$^8$ is hydrogen, C$_1$-C$_6$-alkyl, C$_3$-C$_{12}$-cycloalkyl, amino-C$_1$-C$_6$-alkyl, optionally substituted C$_6$-C$_{12}$-aryl-C$_1$-C$_4$-alkyl or M$_3$-M$_{12}$-heterocyclyl; or
R$^8$, R$^1$
together are C$_1$-C$_4$-alkylene;
R$^{10}$ is hydrogen or C$_1$-C$_6$-alkyl;
R$^{11a}$ is hydrogen or C$_1$-C$_6$-alkyl;
R$^{11b}$ is hydrogen or C$_1$-C$_6$-alkyl;
R$^{12a}$ is hydrogen, optionally substituted C$_1$-C$_6$-alkyl, C$_1$-C$_6$-alkylamino-C$_1$-C$_4$-alkyl, di-C$_1$-C$_6$-alkylamino-C$_1$-C$_4$-alkyl, M$_3$-M$_{12}$-heterocyclyl-C$_1$-C$_6$-alkyl, optionally substituted C$_6$-C$_{12}$-aryl or hydroxy;
R$^{12b}$ is hydrogen or C$_1$-C$_6$-alkyl, or
R$^{12a}$, R$^{12b}$
together with the carbon atom to which they are attached form a carbonyl or are optionally substituted C$_2$-C$_4$-alkylene, wherein one —CH$_2$— of C$_2$-C$_4$-alkylene may be replaced by an oxygen atom or —NR$^{14}$—;
R$^{13a}$ is hydrogen, optionally substituted C$_1$-C$_6$-alkyl, C$_1$-C$_6$-alkylamino-C$_1$-C$_4$-alkyl, di-C$_1$-C$_6$-alkylamino-C$_1$-C$_4$-alkyl, M$_3$-M$_{12}$-heterocyclyl-C$_1$-C$_6$-alkyl, optionally substituted C$_6$-C$_{12}$-aryl or hydroxy;
R$^{13b}$ is hydrogen or C$_1$-C$_6$-alkyl, or
R$^{13a}$, R$^{13b}$
together with the carbon atom to which they are attached form a carbonyl or are optionally substituted C$_2$-C$_4$-alkylene, wherein one —CH$_2$— of C$_2$-C$_4$-alkylene may be replaced by an oxygen atom or —NR$^{15}$—;
R$^{14}$ is hydrogen or C$_1$-C$_6$-alkyl; and
R$^{15}$ is hydrogen or C$_1$-C$_6$-alkyl,
or a physiologically tolerated salt thereof wherein at least one of n1 and n2 is 1, 2 or 3.

2. The compound of claim 1, wherein A is a benzene ring or a ring selected from the group consisting of:

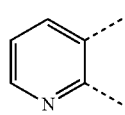 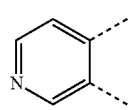 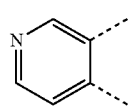

-continued

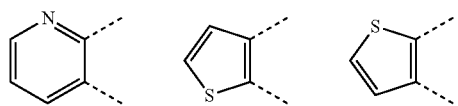

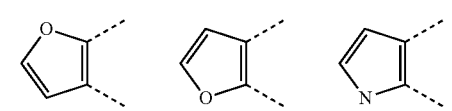

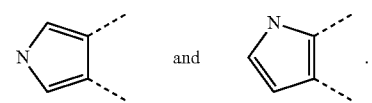

3. The compound of claim 1, wherein R$^1$ is C$_1$-C$_6$-alkyl, C$_3$-C$_{12}$-cycloalkyl-C$_1$-C$_4$-alkyl, or C$_3$-C$_{12}$-cycloalkyl.

4. The compound of claim 1, wherein W is a bond and A$^1$ is a bond.

5. The compound of claim 1, wherein Q is —S(O)$_2$—.

6. The compound of claim 1, wherein the sum of n1+n2 is 2, 3, or 4.

7. The compound of claim 1, wherein X$^1$ is >N—, n1 is 1, and n2 is 1; or X$^1$ is >CH—, n1 is 1, and n2 is 1.

8. The compound of claim 1, wherein R$^6$ is hydrogen or C$_1$-C$_4$-alkyl, or two radicals R$^6$ together with the carbon atom to which they are attached form a carbonyl group.

9. The compound of claim 1, having the formula

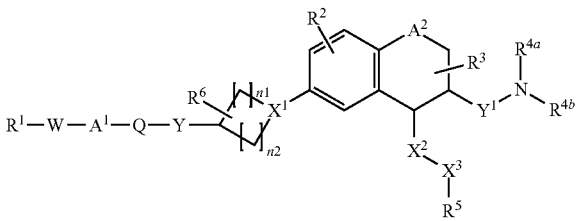

wherein R$^1$, W, A$^1$, Q, Y, n1, n2, X$^1$, R$^6$, R$^2$, A$^2$, R$^3$, Y$^1$, R$^{4a}$, R$^{4b}$, X$^2$, X$^3$, R$^5$ are as defined in claim 1.

10. The compound of claim 1, wherein R$^2$ is hydrogen or halogen.

11. The compound of claim 1, wherein R$^3$ is hydrogen or C$_1$-C$_6$-alkyl.

12. The compound of claim 1, wherein Y$^1$ is a bond.

13. The compound of claim 1, wherein R$^{4a}$ is hydrogen, C$_1$-C$_6$-alkyl, optionally substituted C$_3$-C$_{12}$-cycloalkyl, C$_3$-C$_{12}$-cycloalkyl-C$_1$-C$_4$-alkyl, or M$_3$-M$_{12}$-heterocyclyl and R$^{4b}$ is hydrogen or C$_1$-C$_6$-alkyl; or wherein R$^{4a}$, R$^{4b}$ together are optionally substituted C$_2$-C$_6$-alkylene, wherein one —CH$_2$— of C$_2$-C$_6$-alkylene may be replaced by an oxygen atom.

14. The compound of claim 1 wherein X$^2$ is >CR$^{12a}$R$^{12b}$, X$^3$ is a bond, and R$^{12a}$ is hydrogen or C$_1$-C$_6$-alkyl and R$^{12b}$ is hydrogen or C$_1$-C$_6$-alkyl.

15. The compound of claim 1, having the formula

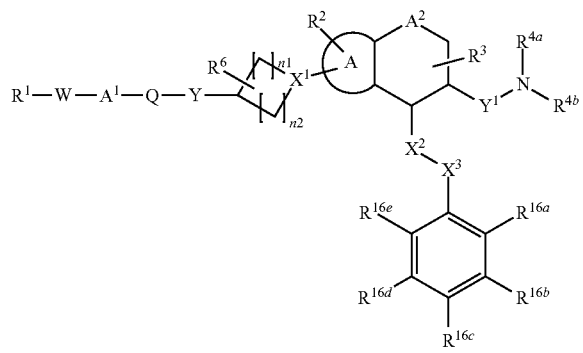

wherein A, $R^1$, W, $A^1$, Q, Y, n1, n2, $X^1$, $R^6$, $R^2$, $R^3$, $A^2$, $Y^1$, $R^{4a}$, $R^{4b}$, $X^2$, $X^3$ are as defined in claim 1; and $R^{16a}$, $R^{16b}$, $R^{16c}$, $R^{16d}$, $R^{16e}$ independently are hydrogen, halogen, or halogenated $C_1$-$C_6$-alkyl.

16. The compound of claim 1, wherein
A is a benzene ring;
$R^1$ is $C_1$-$C_6$-alkyl, $C_3$-$C_{12}$-cycloalkyl-$C_1$-$C_4$-alkyl, or an optionally substituted $M_3$-$M_{12}$-heterocyclyl;
W is a bond;
$A^1$ is a bond;
Q is —$S(O)_2$—;
Y is —$NR^8$—;
n1 is 1;
n2 is 1;
$R^6$ is hydrogen;
$X^1$ is ->N— or >CH—;
$R^2$ is hydrogen or halogen;
$R^3$ is hydrogen;
$Y^1$ is a bond;
$R^{4a}$ is hydrogen, $C_1$-$C_6$-alkyl, $C_3$-$C_{12}$-cycloalkyl-$C_1$-$C_4$-alkyl, or $C_3$-$C_{12}$-cycloalkyl;
$R^{4b}$ is hydrogen or $C_1$-$C_6$-alkyl; or
$R^{4a}$, $R^{4b}$
together are $C_2$-$C_6$-alkylene;
$X^2$ is >$CR^{12a}R^{12b}$;
$X^3$ is a bond;
$R^5$ is optionally substituted phenyl;
$R^8$ is hydrogen;
$R^{12a}$ is hydrogen; and
$R^{12b}$ is hydrogen.

17. The compound of claim 1 which is:
N-[1-[3-(azetidin-1-yl)-4-benzyl-chroman-6-yl]azetidin-3-yl]-1-methyl-imidazole-4-sulfonamide;
Cis-N-(1-(3-(azetidin-1-yl)-4-benzylchroman-6-yl)azetidin-3-yl)ethanesulfonamide;
Cis-N-(1-(3-(azetidin-1-yl)-4-benzylchroman-6-yl)azetidin-3-yl)propane-1-sulfonamide;
Cis-N-(1-(3-(azetidin-1-yl)-4-benzylchroman-6-yl)azetidin-3-yl)-1-cyclopropylmethanesulfonamide;
Cis-N-(1-(3-(azetidin-1-yl)-4-benzylchroman-6-yl)azetidin-3-yl)-1-methyl-1H-pyrazole-4-sulfonamide;
Cis-N-(1-(3-(azetidin-1-yl)-4-benzylchroman-6-yl)azetidin-3-yl)-1-methyl-1H-1,2,3-triazole-4-sulfonamide;
Cis-N-(1-(3-(azetidin-1-yl)-4-benzyl-7-fluorochroman-6-yl)azetidin-3-yl)-1-ethyl-1H-1,2,3-triazole-4-sulfonamide;
Cis-N-(1-(3-(azetidin-1-yl)-4-benzyl-7-fluorochroman-6-yl)azetidin-3-yl)-2-fluoropyridine-3-sulfonamide;
Cis-N-(1-(3-(azetidin-1-yl)-4-benzyl-7-fluorochroman-6-yl)azetidin-3-yl)pyridazine-3-sulfonamide;
Cis-N-(1-(3-(azetidin-1-yl)-4-benzylchroman-6-yl)azetidin-3-yl)-2-fluoropyridine-3-sulfonamide;
Cis-N-(1-(4-benzyl-3-(methylamino)chroman-6-yl)azetidin-3-yl)propane-1-sulfonamide;
Cis-N-(1-(-4-benzyl-3-(methylamino)chroman-6-yl)azetidin-3-yl)ethanesulfonamide;
Cis-N-(1-(4-benzyl-3-(methylamino)chroman-6-yl)azetidin-3-yl)-1-cyclopropylmethanesulfonamide;
Cis-N-(1-(4-benzyl-7-fluoro-3-(methylamino)chroman-6-yl)azetidin-3-yl)ethanesulfonamide;
Trans-N-(1-(4-benzyl-7-fluoro-3-(methylamino)chroman-6-yl)azetidin-3-yl)ethanesulfonamide;
Cis-N-(1-(4-benzyl-7-fluoro-3-(methylamino)chroman-6-yl)azetidin-3-yl)-1-methyl-1H-imidazole-4-sulfonamide;
Trans-N-(1-(4-benzyl-7-fluoro-3-(methylamino)chroman-6-yl)azetidin-3-yl)-1-methyl-1H-imidazole-4-sulfonamide;
Cis-N-(1-(4-benzyl-7-fluoro-3-(methylamino)chroman-6-yl)azetidin-3-yl)propane-1-sulfonamide;
Trans-N-(1-(4-benzyl-7-fluoro-3-(methylamino)chroman-6-yl)azetidin-3-yl)propane-1-sulfonamide;
Cis-N-(1-(4-benzyl-7-fluoro-3-(methylamino)chroman-6-yl)azetidin-3-yl)-1-methyl-1H-pyrazole-4-sulfonamide;
Trans-N-(1-(4-benzyl-7-fluoro-3-(methylamino)chroman-6-yl)azetidin-3-yl)-1-methyl-1H-pyrazole-4-sulfonamide;
Cis-N-(1-(4-benzyl-7-fluoro-3-(methylamino)chroman-6-yl)azetidin-3-yl)-1-methyl-1H-1,2,3-triazole-4-sulfonamide;
Trans-N-(1-(4-benzyl-7-fluoro-3-(methylamino)chroman-6-yl)azetidin-3-yl)-1-methyl-1H-1,2,3-triazole-4-sulfonamide;
Cis-N-(1-(4-benzyl-7-fluoro-3-(methylamino)chroman-6-yl)azetidin-3-yl)-1-cyclopropylmethanesulfonamide;
Trans-N-(1-(4-benzyl-7-fluoro-3-(methylamino)chroman-6-yl)azetidin-3-yl)-1-cyclopropylmethanesulfonamide;
Cis-N-(1-(3-amino-4-benzylchroman-6-yl)azetidin-3-yl)propane-1-sulfonamide;
Cis-N-(1-(3-amino-4-benzylchroman-6-yl)azetidin-3-yl)-1-cyclopropylmethane-sulfonamide;
Cis-1-(4-benzyl-7-fluoro-6-(3-(5-fluoropyridine-3-sulfonamido)azetidin-1-yl)chroman-3-yl)azetidin-1-ium (E)-3-carboxyacrylate;
Cis-N-(1-(4-benzyl-3-(propylamino)chroman-6-yl)azetidin-3-yl)propane-1-sulfonamide;
Cis-N-(1-(4-benzyl-3-(diethylamino)chroman-6-yl)azetidin-3-yl)propane-1-sulfonamide;
Cis-N-(1-(4-benzyl-3-((cyclopropylmethyl)amino)chroman-6-yl)azetidin-3-yl)propane-1-sulfonamide; or
Cis-N-(1-(4-benzyl-3-(cyclobutylamino)chroman-6-yl)azetidin-3-yl)propane-1-sulfonamide,
or a physiologically tolerated salt thereof.

18. A pharmaceutical composition which comprises a carrier and a compound of claim 1.

19. The compound of claim 1 which is Cis-N-(1-(3-(azetindin-1-y)4-benzylchrornan-6-yl)azetidin-3-yl)-1-cyclopropylmethanesulfonamide, or a physiologically tolerated salt thereof.

20. The compound of claim 1 which is Cis-N-(1-(4-benzyl-3-(methylamino) chroman-6-yl)azetidin-3-yl)propane-1-sulfonamide, or a physiologically tolerated salt thereof.

21. The compound of claim 1 which is Cis-N-(1(4-benzyl-3-(methylamino) chroman-6-yl)azetidin-3-yl)-1-cyclopropylmethanesulfonamide, or a physiologically tolerated salt thereof.

* * * * *